US007102000B2

(12) United States Patent
Pfahl et al.

(10) Patent No.: US 7,102,000 B2
(45) Date of Patent: Sep. 5, 2006

(54) HETEROCYCLIC AMIDE DERIVATIVES FOR THE TREATMENT OF DIABETES AND OTHER DISEASES

(75) Inventors: Magnus Pfahl, Solana Beach, CA (US); Catherine Tachdjian, San Diego, CA (US); Hussien A. Al-Shamma, Encinitas, CA (US); Andrea Fanjul Giachino, San Diego, CA (US); Karine Jakubowicz-Jaillardon, Villebon sur Yvette (FR); Jianhua Guo, San Diego, CA (US); Mohamed Boudjelal, San Diego, CA (US); James W. Zapf, San Diego, CA (US)

(73) Assignees: Incyte San Diego Inc., Wilmington, DE (US); Ortho McNeil Pharmaceutical Inc., Rariton, NJ (US)

( * ) Notice: Subject to any disclaimer, the term of this patent is extended or adjusted under 35 U.S.C. 154(b) by 181 days.

(21) Appl. No.: 10/384,352

(22) Filed: Mar. 6, 2003

(65) Prior Publication Data
US 2003/0216432 A1 Nov. 20, 2003

Related U.S. Application Data

(60) Provisional application No. 60/362,702, filed on Mar. 8, 2002.

(51) Int. Cl.
*C07D 413/12* (2006.01)
*C07D 215/16* (2006.01)
*C07D 277/04* (2006.01)

(52) U.S. Cl. .................. 544/137; 544/235.2; 548/183; 546/158; 514/314; 514/326; 514/369; 514/389

(58) Field of Classification Search ............. 544/137, 544/235.2; 548/183; 514/314, 326, 369, 514/389; 546/158
See application file for complete search history.

(56) References Cited

U.S. PATENT DOCUMENTS

| 4,051,842 A | 10/1977 | Hazel et al. |
| 4,140,122 A | 2/1979 | Kühl et al. |
| 4,383,529 A | 5/1983 | Webster |
| 4,668,506 A | 5/1987 | Bawa |
| 4,713,244 A | 12/1987 | Bawa et al. |
| 4,788,063 A | 11/1988 | Fisher et al. |
| 4,824,833 A * | 4/1989 | Iijima et al. ............. 514/230.5 |
| 4,897,393 A * | 1/1990 | Iijima et al. ............. 514/233.8 |
| 4,931,279 A | 6/1990 | Bawa et al. |
| 4,948,900 A * | 8/1990 | Iijima et al. ............... 548/183 |
| 4,971,996 A | 11/1990 | Shiraishi et al. |
| 5,223,522 A | 6/1993 | Clark et al. |
| 5,330,998 A | 7/1994 | Clark et al. |
| 5,512,689 A | 4/1996 | Quallich |
| 5,523,314 A | 6/1996 | Bue-Valleskey et al. |
| 5,599,826 A | 2/1997 | Mertens et al. |
| 5,650,444 A | 7/1997 | Cagiano et al. |
| 5,691,376 A | 11/1997 | Cagiano et al. |
| 5,780,676 A | 7/1998 | Boehm et al. |
| 5,811,439 A | 9/1998 | Ogawa et al. |
| 6,127,415 A | 10/2000 | Pfahl et al. |
| 6,262,044 B1 | 7/2001 | Møller et al. |
| 6,515,003 B1 * | 2/2003 | Pfahl et al. ................. 514/369 |
| 6,765,013 B1 * | 7/2004 | Pfahl et al. ................. 514/369 |
| 6,927,228 B1 | 8/2005 | Bernardon et al. |
| 2002/0143182 A1 | 10/2002 | Pfahl et al. |
| 2003/0083357 A1 | 5/2003 | Pfahl et al. |
| 2003/0105333 A1 | 6/2003 | Pfahl et al. |
| 2003/0144329 A1 | 7/2003 | Pfahl et al. |
| 2003/0153606 A1 | 8/2003 | Pfahl et al. |
| 2003/0216432 A1 | 11/2003 | Pfahl et al. |
| 2004/0034004 A1 | 2/2004 | Pfahl et al. |
| 2004/0097566 A1 | 5/2004 | Pfahl et al. |
| 2005/0014767 A1 | 1/2005 | Pfahl et al. |
| 2005/0038098 A1 | 2/2005 | Tachdijan et al. |
| 2005/0070581 A1 | 3/2005 | Pfahl et al. |

FOREIGN PATENT DOCUMENTS

| EP | 0 212 617 | 3/1987 |
| EP | 0 304 493 | 3/1989 |

(Continued)

OTHER PUBLICATIONS

Bozdag, CA 133:309865, abstract of Arzneimittel-Forschung, 2000, vol. 50(7), pp. 626-630.*

(Continued)

*Primary Examiner*—D. Margaret Seaman
(74) *Attorney, Agent, or Firm*—Needle & Rosenberg, P.C.

(57) ABSTRACT

The present invention relates to certain substituted heterocycles of Formula (200),

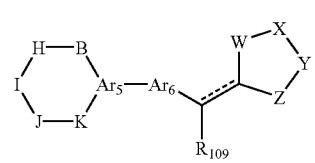

(200)

wherein B, H, I, J and K together with the $Ar_5$ form a ring containing at least one amide residue, and W, X, Y and Z together form a 2,4-thiazolidinedione, 2-thioxo-thiazolidine-4-one, 2,4-imidazolidinedione or 2-thioxo-imidazolidine-4-one residue; or a pharmaceutically acceptable salt thereof. The compounds are useful in the treatment of diseases such as type 2 diabetes, and related disorders of lipid and carbohydrate metabolism, including atherosclerosis. The compounds are also useful for treating diseases of uncontrolled proliferation, such as cancers in general, including breast cancer.

77 Claims, 14 Drawing Sheets

FOREIGN PATENT DOCUMENTS

| | | |
|---|---|---|
| EP | 0 343 643 | 11/1989 |
| EP | 1 048 659 | 11/2000 |
| EP | 1 142 885 | 10/2001 |
| JP | 55 038359 | 3/1980 |
| WO | WO 93/21146 | 10/1993 |
| WO | WO 94/12880 | 6/1994 |
| WO | WO 97/00249 | 1/1997 |
| WO | WO 97/03682 | 2/1997 |
| WO | WO 97/27191 | 7/1997 |
| WO | WO 99/09965 | 3/1999 |
| WO | WO 99/24415 | 5/1999 |
| WO | WO 99/58127 | 11/1999 |
| WO | WO 00/10573 | 3/2000 |
| WO | WO 00/18748 | 4/2000 |
| WO | WO 00/32598 | 6/2000 |
| WO | WO 00/63196 | 10/2000 |
| WO | WO 00/066167 | 11/2000 |
| WO | WO 01/16122 | 3/2001 |
| WO | WO 01/16123 | 3/2001 |
| WO | WO 01/36402 | 5/2001 |
| WO | WO 02/12210 | 2/2002 |
| WO | WO 02/071827 | 9/2002 |
| WO | WO 02/072009 | 9/2002 |
| WO | WO 02/072543 | 9/2002 |
| WO | WO 02/080935 A1 | 10/2002 |

OTHER PUBLICATIONS

Bozdag, CA 133:237715, Arzneimittel-Forschung, 2000, vol. 50(6), pp. 539-543.□□.*

Ertan, CA 126:293290, Acta pharmaceutica Turcica, 19997, vol. 39(1), pp. 33-37.*

Alley et al., "Feasibility of Drug Screening with Panels of Human Tumor Cell Lines Using a Microculture Tetrazolium Assay," *Cancer Re.*, 48:589-601 (1988).

Amin et al., "Nitric Oxide Synthase and Cyclooxygenases: Distribution, Regulation, and Intervention in Arthritis," *Nitric pin. Rheumatol*, 11(3):202-209 (1999).

Aranyos et al., "Novel Electron-Rich Bulky Phospine Ligands Facilitate the Palladium-Catalyzed Preparation of Diaryl Ethers," *J. Am. Chem. Soc.*, 121:4369-4378 (1999).

Baraldi et al., "Exhaled Nitric Oxide Concentrations During Treatment of Wheezing Exacerbation in Infants and Young Children," *Am. J. Respir. Crit. Care Med.*, 159 (4 Pt. 1):1284-1288 (1999).

Beilstein Registry No. 29-30, 1975, Compound Registry No. 1120438.

Beilstein Registry No. 52, 1978, Compound Registry No. 4939128.

Black, "Simple Synthesis of 1-Azaadamantan-4-one," *Synthesis*, 829-830 (1981).

Blondet et al., "Convenient Synthesis of 6-Methyl, 8-Methyl and 6,8-Dimethyl Derivatives of 5-Hydroxy-1,2,3,4-Tetrahydro-2-Quinolinone," *Organic Preparation and Procedures Int.*, 25(2):223-228 (1993).

Bradisher et al., "Aromatic Cyclodehydration XXIV. Cyclization of Derivatives of (2-biphenylly)pyruvic Acid," *J. Org. Chem.*, 15(2) 374-376 (1950).

Bredt et al., "Isolation of Nitric Oxide Synthetase, a Calmodulin-Requiring Enzyme," *Proc. Natl. Acad. Sci.*, 87:682-685 (1990).

Brennan et al., "Inhibitory Effect of TNF Antibodies on Synovial Cell Interleukin-1 Production in Rheumatoid Arthritis," *Lancet*, 2:244-247 (1989).

Cantello et al., "A Versatile Route to 2-Arylmethyl-1,2-oxadiazolidine-3,5-diones via Regiospecific Alkyl-ation of 1,2,4-Oxadiazolidine-3,5-dione," *Synlett*, 263-264 (1997).

Cantello et al., "The Synthesis of BRL 49653—A Novel and Potent Antihyperglycaemic Agent," *Bioorganic & MedicinalChemistry Letters*, 4:1181-1184 (1994).

Chan et al., "New N- and O-Arylations with Phenyloboronic Acids and Curpric Acetate," *Tetrahedron Letters*, 39:2933-2936 (1998).

Chang et al., "The Upjohn Colony of Kka$^y$ Mice: A Model for Obese Type II Diabetes," *Elsevier Science Publishers B.V., Biomedical Division, Diabetes*pp. 466-470 (1986).

Charpentier et al., "Synthesis, Structure—Affinity Relationships, and Biological Activities of Ligands Binding Retinoic Acid Receptor Subtypes," *J. Med. Chem.*, 38:4993-5006 (1995).

Choi et al., "Similarity of Colorectal Cancer in Crohn's Disease and Ulcerative Colitis: Implications for Carcinogenesis and Prevention," *Gut*, 35:950-954 (1994).

Cobb et al., "N-(2-Benzoylphenyl)-L-tyrosine PPARγ Agonists. 3. Structure-Activity Relationship and Optimization of the N-Aryl Substituent," *J. Med. Chem.*, 41:5055-5069 (1998).

Coleman "Diabetes-Obesity Syndromes in Mice," *Diabetes*, 31(1):1-6 (Apr. 1982).

Darses et al., "Palladium-Catalyzed Cross-Coupling Reactions of Arenediazonium Tetrafluoroborates with Aryl- and Alkenylboronic Acids," *Bull. Soc. Chem. Fr.*, 133:1095-1102 (1996).

Dawson et al., "Conformational Effects on Retinoid Receptor Selectivity. 2. Effects of Retinoid Bridging Group on Retinoid X Receptor Activity and Selectivity," *J. Med. Chemistry*, 38:3368-3383 (1995).

Dawson et al., "The Synthetic Chemistry of Retinoids," *Biology, Chemistry, and Medicine*, 2$^{nd}$ Edition, Raven Press, Ltd., New York (1994).

Ebisawa et al., "Novel Thiazolidinedione Derivatives with Retinoid Synergistic Activity," *Biol. Pharma. Bull.*, 21(5):547-549 (1998).

Evans et al., "Synthesis of Diaryl Ethers through the Copper-Promoted Arylation of Phenols with Arylboronic Acids. An Expedient Synthesis of Thyroxine," *Tetrahedron Letters*, 39:2937-2940 (1998).

Farahat et al., "Cytokine Epression in Synovial Membranes of Patients with Rheumatoid Arthritis and Osteoarthritis," *Ann. Rheum. Dis.*, 52: 870-875 (1993).

Ferrell, "Tripping the Switch Fantastic: How A Protein Kinase Cascade Can Convert Graded Inputs into Switch-Like Outputs," *TIBS*, 21:460-466 (1966).

Firooznia et al., "Enantioselective Synthesis of 4-Substituted Phenylalanines By Cross-Coupling Reactions," *Tetrahedron Letters*, 40:213-216 (1999).

Förstermann et al., "Induced RAW 264.7 Macrophages Express Soluble and Particulate Nitric Oxide Synthase: Inhibition By Transforming Growth Factor-," *Eur. J. Pharm.*, 225:161-165 (1992).

Fukuto et al., "Inhibition of Constitutive and Inducible Nitric Oxide Synthase: Potential Selective Inhibition," *Annu. Rev. Pharmacol. Toxicol.* 35:165-194 (1995).

Gahtan et al., "Inflammatory Pathogenesis in Alzheimer's Disease: Biological Mechanisms and Cognitive Sequeli," *Neurosci: Biobehav*, 23:615-633 (1999).

Glauser et al., "Pathogenesis and Potential Strategies for Prevention and Treatment of Septic Shock: An Update," *Clin. Infect Dis*. 18 (Suppl. 2):S205-216 (1994).

Gown, et al., "Human Atherosclerosis—II. Immunocytochemical Analysis of the Cellular Composition of Human Atherosclerotic Lesions," *Am. J. Pathol.*, 125(1):191-207 (1986).

Gray et al., "Practical Methylation of Aryl Halides by Suzuki-Miyaura Coupling," *Tetrahedron Letters*, 41:6237-6240 (2000).

Haddach et al., "A New Method for the Synthesis of Ketones: The Palladium-Catalyzed Cross-Coupling of Acid Chlorides with Arylboronic Acids," *Tetrahedron Letters*, 40:3109-3112 (1999).

Harris et al., "Localization of a Pioglitazone Response Element in the Adipocyte Fatty Acid-Binding Protein Gene," *Mol. Pharmacol.*, 45:439-445 (1994).

Hudlicky, "Oxidations in Organic Chemistry," *ACM Monograph*, 186:114-127 (1990).

Hudlicky, "Oxidations in Organic Chemistry," *ACS Monograph*, 186:133-149 (1990).

Indolese, "Suzuki-Type Coupling of Chloroarenes with Arylboronic Acids Catalysed by Nickel Complexes," *Tetrahedron Letters*, 38:3513-3516 (1997).

Ishiyama et al., "Palladium(0)-Catalyzed Cross-Coupling Reaction of Alkoxydiboron with Haloarenes: A Direct Procedure for Arylboronic Esters," *J. Org. Chem.*, 60:7508-7510 (1995).

Ishiyama et al., "Palladium-Catalyzed Carbonylative Cross-Coupling Reaction of Arylboronic Acids with Aryl Electrophiles: Synthesis of Biaryl Ketones," *J. Org. Chem.*, 63:4726-4731 (1998).

Ishiyama et al. "Synthesis of Arylboronates via the Palladium(0)-Catalyzed Cross-Coupling Reaction of Tetra(alkoxo)diborons with Aryl Triflates," *Tetrahedron Letters*, 38:3447-3450 (1997).

Ishiyama et al. "Synthesis of Unsymmetrical Biaryl Ketones via Palladium-Catalyzed Carbonylative Cross-Coupling Reaction of Arylboronic Acids with Iodoarenes," *Tetrahedron Letters*, 34:7595-7598 (1993).

Jung et al., "New Efficient Method for the Total Synthesis of (S,S)-Isodityrosine from Natural Amino Acids," *J. Org. Chem.*, 64:2976-2977 (1999).

Kamidawa et al., "Palladium-Catalyzed Amination of Aryl Bromides Utilizing Arene-Chromium Complexes as Ligands," *J. Org. Chem.*, 63:8407-8410 (1998).

Kawai et al., "Enhancement of Rat Urinary Bladder Tumorigenesis by Lipopolysaccharide-induced inflammation," *Cancer Res.*, 53:5172-5175 (1993).

Kriegler et al., "A Novel Form of TNF/Cachectin is a Cell Surface Cytotoxic Transmembrane Protein: Ramifications for the Complex Physiology of TNF," *Cell*, 53:45-53 (1988).

Kyriakis et al., "Sounding the Alarm: Protein Kinase Cascades Activated by Stress and Inflammation," *J. Biol Chem.*, 271:24313-24316 (1996).

Littke et al., "A Convenient and General Method for Pd-Catalyzed Suzuki Cross-Couplings of Aryl Chlorides and Arylboronic Acids," *Angew. Chem. Int. Ed.*, 37:3387-3388 (1998).

Louie et al., "Palladium-Catalyzed Amination of Aryl Triflates and Importance of Triflate Addition Rate," *J. Org. Chem.*, 62:1268-1273 (1997).

Manickam et al., "New Parts for a Construction Set of Bifunctional Oligo(het)arylene Building Blocks for Modular Chemistry," *Synthesis*, 3:442-446 (2000).

McCann et al., "The Nitric Oxide Hypothesis of Aging," *Exp. Gerontol*, 33(7-8):813-826 (1998).

McCann, "The Nitric Oxide Hypothesis of Brain Aging," *Exp. Gerontol*, 32:431-440 (1997).

Miyaura et al., "Palladium-Catalyzed Cross-Coupling Reactions of Organoboron Compounds," *Chem. Rev.*, 95:2457-2483 (1995).

Molina et al., "The Role of Nitric Oxide in Neurodegeneration—Potential for Pharmacological Intervention," *Drugs & Aging*, 12(4):251-259 (1998).

Moroz et al., "The Ullmann Ether Condensation," *Russ. Chem. Rev.*, 43:679-689 (1974).

Oliff, "The Role of Tumor Necrosis Factor (Cachectin) in Cachexia," *Cell*, 54:141-142 (1988).

Oram, "Molecular Basic of Cholesterol Homeostasis: Lessons from Tangier Disease and ABCA1," *Trends in Molecular Medicines*, 8(4):168-173 (2002).

Paradisi, "Arene Substitution via Nucleophilic Addition to Electron Deficient Arenes," *Comprehensive Organic Synthesis*, 4:423-450 (1991).

Petrov et al., "The Arbuzov Rearrangement with Participation of Halogenoacetylenes as a Method of Synthesis of Ethynylphosphonates and other Organo-phosphorus Compounds," *Russ. Chem. Rev.*, 52:1030-1035 (1983).

Pohlman et al., "An Endothelial Cell Surface Factor(s) Induced in Vitro By Lipopolysaccharide, Interleukin 1, and Tumor Necrosis Factor- Increases Neutrophil Adherence By A CDw18-Dependent Mechanism," *J. Immunol*, 136:4548-4553 (1986).

Pollock et al., "Purification and Characterization of Particulate Endothelium-derived Relaxing Factor Synthase from Cultured and Native Bovine Aortic Endothelial Cells," *Proc. Nat. Acad. Sci.*, 88:10480-10484 (1991).

Pujol-Borrell et al., "HLA Class II Induction In Human Islet Cells By Interferon- Plus Tumour Necrosis Factor or Lymphotoxin," *Nature*, 326:304-306 (1987).

Rosin et al., "Inflammation, Chromosomal Instability, and Cancer: The Schistosomiasis Model" *Cancer Res.*, 54 (7 Suppl):1929s-1933s (1994).

Ross "Atherosclerosis—An Inflammatory Disease," *New England Journal of Medicine*, 340(2):115-126 (Jan. 1999).

Rust et al., "Tangier disease is caused by mutations in the gene encoding ATP-binding cassette transporter 1," *Nature Genetics*, 22:352-355 (Aug. 1999).

Sanders, "Asthma, Viruses, and Nitric Oxide," *Proc. Soc. Exp. Biol. Med.*, 220(3):123-132 (1999).

Schandendorf et al., "Retinoic Acid Receptor-γ Selective Retinoids Exert Antiproliferative Effects on Human Melanoma Cell Growth *In Vitro*," *International Journal of Oncology*, 5:1325-1331 (1994).

Serfaty-Lacrosniere et al., "Homozygous Tangier disease and cardiovascular disease," *Atherosclerosis*, 107:85-98 (1994).

Shao et al., "p53 Independent $G_0/G_1$ Arrest and Apoptosis Induced by a Novel Retinoid in Human Breast Cancer Cells," *Oncogene*, 11:493-504 (1995).

Smith et al., "The Active Form of Tumor Necrosis Factor Is A Trimer," *J. Biol. Chem.*, 262:6951-6954 (1987).

Sparrow et al., "A Potent Synthetic LXR Agonist is More Effective than Cholesterol Loading at Inducing ABCA1 mRNA and Stimulating Cholesterol Efflux," *Journal of Biological Chemistry*, 277(12):10021-10027 (2002).

Spruce et al., "Heteroarotinoids. Synthesis, Characterization, and Biological Activity in Terms of an Assessment of these Systems to Inhibit the Induction of Ornithine Decarboxylase Activity and to Induce Terminal Differentiation of HL-60 Cells," *J. Med. Chem.*, 30:1474-1482 (1987).

Stanforth, "Catalytic Cross-Coupling Reactions in Biaryl Synthesis," *Tetrahedron*, 54:263-303 (1998).

Stirling et al., "Increase In Exhaled Nitric Oxide Levels in patients With Difficult Asthma and Correlation With Symptoms and Disease Severity Despite Treatment With Oral and Inhaled Corticosteroids," *Thorax*, 53(12):1030-1034 (1998).

Strieter et al., "Endothelial Cell Gene Expression of a Neutrophil Chemotactic Factor by TNF-, LPS, and IL-1," *Science*, 243:1467-1469 (1989).

Suzuki, "New Synthetic Transformations Via Organoboron Compounds," *Pure & Applied Chem.*, 66:213-222 (1994).

Teboul et al., "Thiazolidinediones and Fatty Acids Convert Moygenic Cells Into Adipose-like Cells," *J. Biol. Chem.*, 270:28183-28187 (1995).

Thompson et al., "Effect of carcinogen dose and age at administration on induction of mammary carcinogenesis by 1-methyl-1-nitrosourea," *Carginogenesis*, 13(9):1535-1539 (1992).

Thorns et al., "nNOS Expressing Neurons in the Entorhinal Cortex and Hippocampus Are Affected in Patients With Alzheimer's Disease," *Exp. Neurol*, 150:14-20 (1998).

Tietze et al., "The Knoevenagel Reaction," *Comprehensive Organic Synthesis*, 2:341-394 (1991).

Tracey et al., "Anti-Cachetin/TNF Monoclonal Antibodies Prevent Septic Shock During Lethal Bacteraemia," *Nature*, 330:662-664 (1987).

Tracey et al., "Tumor Necrosis Factor: A Pleiotropic Cytokine and Therapuetic Target," *Ann. Rev. Med.*, 45:491-503 (1994).

Uysal et al. "Protection From Obesity-induced Insulin Resistance in Mice Lacking TNF- Function," *Nature*, 389:610-614 (1997).

Wadsworth, "Synthetic Applications of Phosphoryl-Stabilized Anions," *Organic Reactions*, 25:73-253 (1977).

Walter et al., "The High Density Lipoprotein—and Apolipoprotein A-1-Induced Mobilization of Cellular Cholesterol is Impaired in Fibroblasts from Tangier Disease Subjects," *Biochemical and Biophysical Research Communications*, 205(1):850-856 (1994).

Watanabe et al., "Synthesis of Sterically Hindered Biaryls via the Palladium-Catalyzed Cross-Coupling Reaction of Arylboronic Acids or Their Esters With Haloarenes," *Synlett.*, 207-210 (1992).

Weiberth et al., "Copper(I)-Activated Addition of Grignard Reagents to Nitriles. Synthesis of Ketimines, Ketones, and Amines," *J. Org. Chem.*, 52:3901-3904 (1987).

Wilson et al., "The Structure-Activity Relationshop Between Peroxisome Proliferator-Activated Receptor Agonism and the Antihyperglycemic Activity of Thiazolidinediones," *J. Med. Chem.*, 39:665-668 (1996).

Wolfe et al., "Scope and Limitations of the Pd/BINAP-Catalyzed Amination of Aryl Bromides," *J. Org. Chem.*, 65:1144-1157 (2000).

Wolfe et al., "Simple, Efficient Catalyst System for the Palladium-Catalyzed Amination of Aryl Chlorides, Bromides and Triflates," *J. Org. Chem.*, 65:1158-1174 (2000).

Yun et al., "Neurobiology of Nitric Oxide," *Crit. Rev. Neurobiol.*, 10:291-316 (1996).

Zask et al., "Synthesis of 3-Mercapto-2(*5H*)-Furanones via Reaction of Dilithio-2,4-thiazolidinedione With -Halo Ketones," *Tetrahedron Letters*, 34 (17):2719-2722 (1993).

Zask et al., "Synthesis and Antihyperglycemic Activity of Novel 5-(naphthalenylsufonyl)-2,4-thiazolodinediones," *J.Med.Chem.*, 33:1418-1423 (1990).

Barclay et al., "ortho-Diquaternary aromatic compounds. III. Synthesis and reactions of polyalkyltetralones and derivatives," *Canadian Journal of Chemistry*, 48(17):2763-2775 (1970).

Cacchi et al., "Palladium-Catalyzed Triethylammonium Formate Reduction of Aryl Triflates. A Selective Method for the deoxygenation of phenols," *Tetrahedron Letters*, 27(45):5541-5544 (1986).

Faul et al., "Synthesis of Novel Retinoid X Receptor-Selective Retinoids," *J. Org. Chem.*, 66:5772-5782 (2001).

Iwatsuka et al., "General Survey of Diabetic Features of Yellow KK Mice," *Endocrinol. Japon.* 17:23-35 (1970).

Xiong et al., "Human D-Type Cyclin," *Cell*, 65:691-699 (1991).

U.S. Appl. No. 11/210,403, filed Aug. 24, 2005, Pfahl et al.
U.S. Appl. No. 09/655,460, filed Sep. 5, 2000, Pfahl et al.
U.S. Appl. No. 10/334,932, filed Dec. 31, 2002, Pfahl et al.
U.S. Appl. No. 10/094,142, filed Mar. 7, 2002, Pfahl et al.
U.S. Appl. No. 10/098,184, filed Mar. 8, 2002, Pfahl et al.
U.S. Appl. No. 10/224,288, filed Aug. 19, 2002, Pfahl et al.
U.S. Appl. No. 10/298,024, filed Nov. 15, 2002, Pfahl et al.
U.S. Appl. No. 10/313,341, filed Dec. 6, 2002, Pfahl et al.
U.S. Appl. No. 10/384,391, filed Mar. 6, 2003, Pfahl et al.
U.S. Appl. No. 60/443,426, filed Jan. 29, 2003, Pfahl et al.
U.S. Appl. No. 60/464,388, filed Apr. 18, 2003, Tachdjian et al.

* cited by examiner

Serum Cholesterol Level in Diet-Induced Hypercholesteromia in Sprague Dawley Rats Figure 8. Synthesis of Precursors of Ar$_5$

HETEROCYCLIC AMIDE DERIVATIVES FOR THE TREATMENT OF DIABETES AND OTHER DISEASES

RELATED APPLICATIONS

This application claims priority to the U.S. Provisional Application Ser. No. 60/362,702, filed Mar. 8, 2002, the disclosure of which application is hereby incorporated in its entirety by this reference.

BACKGROUND OF THE INVENTION

Type 2 diabetes, also referred to as non-insulin dependent diabetes mellitus (NIDDM), afflicts between 80 and 90% of all diabetic patients in developed countries. In the United States alone, approximately 15 million people, and more than 100 million worldwide, are affected. Because this disorder is a late onset disease and occurs often in overweight persons, it can be expected that the number of patients suffering from this disease will increase further. Patients suffering from type 2 diabetes usually still produce insulin but become increasingly resistant to their own insulin and to insulin therapy.

A new class of drugs has been recently introduced that resensitizes patients to their own insulin (insulin sensitizers), thereby reducing blood glucose and triglyceride levels, and thus abolishing, or at least reducing, the requirement for exogenous insulin. Troglitazone (Resulin™) and rosiglitazone (Avandia™) were among the first representatives of this class of drugs approved for the treatment of type 2 diabetes in the United States and several other countries. The currently approved compounds can however have side effects including rare but severe liver toxicities and they can increase body weight in humans. Such side effects are of major concern for diabetes patients who can require treatment for a decade or longer. Therefore, new and better drugs for the treatment of type 2 diabetes and related disorders are needed. In particular, drugs that can control blood sugar levels and simultaneously control hyperlipidemia and hypercholesterolemia are desirable. Elevated levels of cholesterol lead to atherosclerosis and heart disease which in many type 2 diabetes patients is the cause of death.

There is also a need for the more effective drugs to treat diseases of uncontrolled cellular proliferation, such as cancers. Certain molecules that have strong cellular differentiation activity can inhibit the uncontrolled cellular proliferation of cancer cells, in particular breast cancer.

Small molecules that can be effective for the treatment of diabetes and/or disorders of carbohydrate metabolism were disclosed in U.S. Pat. No. 6,515,003, issued Feb. 4, 2003, based on U.S. patent application Ser. No. 09/652,810, filed Aug. 31, 2000, which claimed priority to U.S. Provisional Patent Application 60/151,670, filed Aug. 31, 1999. Related small molecules that can be useful in the treatment of certain cancers were disclosed in PCT Patent Application WO 01/16122, published Mar. 8, 2001, which claimed priority to the same U.S. Provisional Patent Application 60/151,670 cited above. The disclosures of all the above-described patent documents are hereby incorporated herein by this reference, for both their chemical structural disclosures, their teachings of the biological activities of those compounds, and methods for their use as pharmaceutical compositions.

There is however a continuing need for effective drugs for the treatment of cancers, and for the treatment of type 2 diabetes and associated disorders of carbohydrate and/or lipid metabolism, including hyperlipidemia and hypercholesterolemia. In particular, there is a continuing need new drugs that can control the blood sugar levels of diabetics, and simultaneously control hyperlipidemia and hypercholesterolemia so as to lessen or prevent atherosclerosis.

SUMMARY OF THE INVENTION

Some embodiments of the invention relate to heterocyclic compounds having the structure

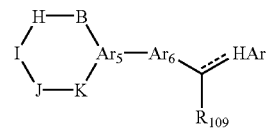

wherein
a) $Ar_5$ is an aryl, substituted aryl, heteroaryl, or substituted heteroaryl;
b) B, H, I, J and K are independently selected from —C(O)—, —C(S)—, —O—, —S—, —N($R_{101}$)—, —N($R_{102}$)—, —C($R_{103}$)($R_{104}$)—, —C($R_{105}$)($R_{106}$)—, or —C($R_{107}$)($R_{108}$)—, wherein one, or two of B, H, I, J or K can optionally be absent; and
  i) $R_{101}$, $R_{102}$, $R_{103}$, $R_{104}$, $R_{105}$, $R_{106}$, $R_{107}$ and $R_{108}$ are independently selected from hydrogen, hydroxyl, a halogen, amino, or an organic radical;
  ii) two of B, H, I, J and K form at least one radical having the structure

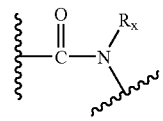

wherein $R_x$ is a $R_{101}$, or $R_{102}$ radical;
  iii) $Ar_5$ together with B, H, I, J and K comprise from 2 to 24 carbon atoms;
c) $Ar_6$ is an aryl, substituted aryl, heteroaryl, or substituted heteroaryl;
d) $R_{109}$ is hydrogen, hydroxy, or an organic radical;
e) ----- is either present or absent;
f) HAr is a heterocycle having the structure

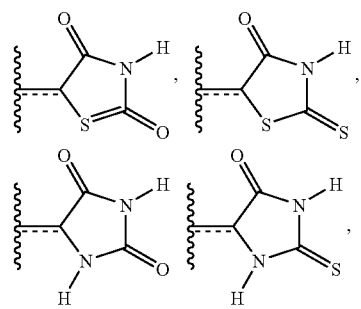

or a pharmaceutically acceptable salt thereof.
As can be seen from the above description, the compounds of the invention have a heterocyclic ring comprising B, H, I, J and K residues, wherein the heterocyclic ring comprises an amide residue having the structure;

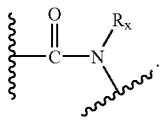

The heterocyclic amide compounds comprising an amide residue have been found to be unexpectedly active for advantageously regulating carbohydrate metabolism, including serum glucose levels. The heterocyclic amide compounds have also been found to be unexpectedly effective modulators of lipid metabolism, and are therefore useful for the treatment of hyperlipidemia and/or hypercholesterdemia. Therefore, the heterocyclic amide compounds of the invention can simultaneously and beneficially regulate carbohydrate and lipid metabolism so as to simultaneously decrease levels of serum glucose, serum triglycerides, and serum cholesterol. As a result, it has been found that the heterocyclic amide compounds are unexpectedly useful for the treatment of type 2 diabetes and the simultaneous treatment of the hyperlipidemia, hypercholesterdemia, and/or atherosclerosis which is often associated with diabetes. The heterocyclic amide compounds of the invention have also been found to have unexpectedly superior pharmaceutical properties, including unexpectedly superior oral bioavailability as compared to prior art compounds.

The heterocyclic compounds of the present invention also show activity for inducing adipocyte differentiation in certain well known cell lines of pre-adipocytes. The ability of a compound to induce differentiation of these cell lines is also known to correlate with anticancer activity. As a result, the heterocyclic compounds of the invention have been tested for utility in the treatment of diseases of uncontrolled proliferation. The heterocyclic compound described herein have shown unexpectedly effective results for the treatment of breast cancer in an in vivo rat model of breast cancer.

Further embodiments of the amide compounds of the invention, and pharmaceutical compositions comprising one or more of the compounds of the invention will be described in more detail in the specification and written description hereinbelow. Other embodiments of the invention relate to methods of synthesizing the amide compounds disclosed herein.

The invention also provides methods for the treatment of diabetes and associated diseases, as well as methods for the treatment of diseases of uncontrolled cellular proliferation comprising administering to a mammal diagnosed as having a disease of uncontrolled cellular proliferation one or more compounds of the invention, or a pharmaceutical composition thereof.

Additional advantages of the invention will be set forth in part in the description which follows, and in part will be obvious from the description, or can be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DETAILED DESCRIPTION

Figure 1:
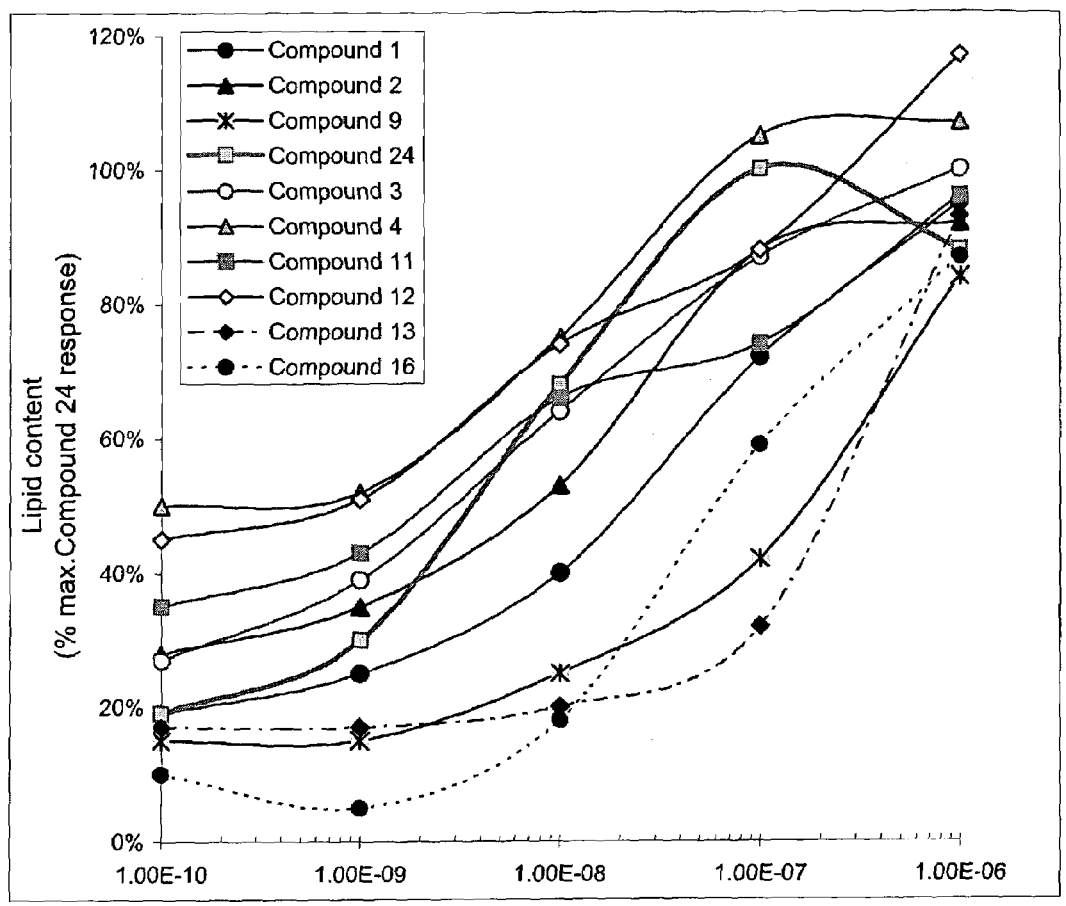
FIG. 1 shows the results of in-vitro screening assays for the ability of some of the compounds of the invention to induce differentiation of 3T3-L1 pre-adipocytes to adipocytes.

The present invention can be understood more readily by reference to the following detailed description of various embodiments of the invention and the Examples included therein and to the Figures and their previous and following description. Before the present compounds, compositions, and/or methods are disclosed and described, it is to be understood that this invention is not limited to specific synthetic methods, specific pharmaceutical carriers or formulations, or to particular modes of administering the compounds of the invention, as such can, of course, vary. It is also to be understood that the terminology used herein is for the purpose of describing particular embodiments only and is not intended to be limiting.

The present invention provides heterocyclic amide compounds that are useful, for example, to modulate lipid and/or carbohydrate metabolism, and especially for the treatment of diabetes, such as type 2 diabetes, and other diseases. In addition, compounds of the invention have demonstrated unexpectedly superior oral bioavailability, as exhibited by their high blood levels after oral dosing in animals. Oral bioavailability allows oral dosing for use in chronic diseases, with the advantage of self-administration and decreased cost over other means of administration. The compounds described herein can be used effectively to prevent, alleviate or otherwise treat type 2 diabetes and/or other disease states in mammals and/or humans, such as atherosclerosis and diseases related to inflammation and/or uncontrolled proliferation, including cancers such as breast cancer.

Definitions

In the specification and Formulae described herein the following terms are hereby defined.

"Optional" or "optionally" means that the subsequently described event or circumstance may or may not occur, and that the description includes instances where said event or circumstance occurs and instances where it does not. For example, the phrase "optionally substituted lower alkyl" means that the lower alkyl group may or may not be substituted and that the description includes both unsubstituted lower alkyl and lower alkyls where there is substitution.

It must be noted that, as used in the specification and the appended claims, the singular forms "a," "an" and "the" include plural referents unless the context clearly dictates otherwise. Thus, for example, reference to "an aromatic compound" includes mixtures of aromatic compounds.

Often, ranges are expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

By "pharmaceutically acceptable" is meant a material that is not biologically or otherwise undesirable, i.e., the material can be administered to an individual along with the relevant active compound without causing clinically unacceptable biological effects or interacting in a deleterious manner with any of the other components of the pharmaceutical composition in which it is contained.

By the term "effective amount" of a compound as provided herein is meant a sufficient amount of the compound to provide the desired regulation of a desired function, such as gene expression, protein function, or a disease condition. As will be pointed out below, the exact amount required will vary from subject to subject, depending on the species, age, and general condition of the subject, the severity of the disease that is being treated, the particular compound used, its mode of administration, and the like. Thus, it is not possible to specify an exact "effective amount." However, an appropriate effective amount can be determined by one of ordinary skill in the art using only routine experimentation.

The term "alkyl" denotes a hydrocarbon group or residue which is structurally similar to a non-cyclic alkane compound modified by the removal of one hydrogen from the non-cyclic alkane and the substitution therefore of a non-hydrogen group or residue. Alkyls comprise a noncyclic, saturated, straight or branched chain hydrocarbon residue having from 1 to 12 carbons, or 1 to 8 carbons, or 1 to 6 carbons. Examples of such alkyl radicals include methyl, ethyl, n-propyl, iso-propyl, n-butyl, sec-butyl, t-butyl, amyl, t-amyl, n-pentyl and the like. Lower alkyls comprise a noncyclic, saturated, straight or branched chain hydrocarbon residue having from 1 to 4 carbon atoms.

The term "substituted alkyl" denotes an alkyl radical analogous to the above definition that is further substituted with one, two, or more additional organic or inorganic substituent groups. Suitable substituent groups include but are not limited to hydroxyl, cycloalkyl, amino, mono-substituted amino, di-substituted amino, acyloxy, nitro, cyano, carboxy, carboalkoxy, alkylcarboxamide, substituted alkylcarboxamide, dialkylcarboxamide, substituted dialkylcarboxamide, alkylsulfonyl, alkylsulfinyl, thioalkyl, thiohaloalkyl, alkoxy, substituted alkoxy, haloalkoxy, heteroaryl, substituted heteroaryl, aryl or substituted aryl. When more than one substituent group is present then they can be the same or different. The organic substituent groups can comprise from 1 to 12 carbon atoms, or from 1 to 6 carbon atoms, or from 1 to 4 carbon atoms.

The term "alkenyl" denotes an alkyl residue as defined above that comprises at least one carbon-carbon double bond. Examples include but are not limited to vinyl, allyl, 2-butenyl, 3-butenyl, 2-pentenyl, 3-pentenyl, 4-pentenyl, 2-hexenyl, 3-hexenyl, 4-hexenyl, 5-hexanyl, 2-heptenyl, 3-heptenyl, 4-heptenyl, 5-heptenyl, 6-heptenyl and the like. The term "alkenyl" includes dienes and trienes of straight and branch chains.

The term "substituted alkenyl" denotes an alkenyl residue as defined above definitions that is substituted with one or more groups, but preferably one, two or three groups, selected from halogen, hydroxyl, cycloalkyl, amino, mono-substituted amino, di-substituted amino, acyloxy, nitro, cyano, carboxy, carboalkoxy, alkylcarboxamide, substituted alkylcarboxamide, dialkylcarboxamide, substituted dialkylcarboxamide, alkylsulfonyl, alkylsulfinyl, thioalkyl, thiohaloalkyl, alkoxy, substituted alkoxy or haloalkoxy. When more than one group is present then they can be the same or different. The organic substituent groups can comprise from 1 to 12 carbon atoms, or from 1 to 6 carbon atoms, or from 1 to 4 carbon atoms.

The term "alkynyl" denotes a residue as defined above that comprises at least one carbon-carbon double bond. Examples include but are not limited ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl and the like. The term "alkynyl" includes di- and tri-ynes.

The term "substituted alkynyl" denotes an alkylnyl residue of the above definition that is substituted with one or more groups, but preferably one or two groups, selected from halogen, hydroxyl, cycloalkyl, amino, mono-substituted amino, di-substituted amino, acyloxy, nitro, cyano, carboxy, carboalkoxy, alkylcarboxamide, substituted alkylcarboxamide, dialkylcarboxamide, substituted dialkylcarboxamide, alkylsulfonyl, alkylsulfinyl, thioalkyl, thiohaloalkyl, alkoxy, substituted alkoxy or haloalkoxy. When more than one group is present then they can be the same or different. The organic substituent groups can comprise from 1 to 12 carbon atoms, or from 1 to 6 carbon atoms, or from 1 to 4 carbon atoms.

The term "cycloalkyl" denotes a hydrocarbon group or residue which is structurally similar to a cyclic alkane compound modified by the removal of one hydrogen from the cyclic alkane and substitution therefore of a non-hydrogen group or residue. Cycloalkyl groups, or residues radical contain 3 to 18 carbons, or preferably 4 to 12 carbons, or 5 to 8 carbons. Examples include as cyclopropyl, cyclobutyl, cyclopentyl, cyclohexyl, cycloheptyl, decahydronapthyl, adamantyl, and like residues.

The term "substituted cycloalkyl" denotes a cycloalkyl residue as defined above that is further substituted with one, two, or more additional organic or inorganic groups that can include but are not limited to halogen, alkyl, substituted alkyl, hydroxyl, alkoxy, substituted alkoxy, carboxy, carboalkoxy, alkylcarboxamide, substituted alkylcarboxamide, dialkylcarboxamide, substituted dialkylcarboxamide, amino, mono-substituted amino or di-substituted amino. When the cycloalkyl is substituted with more than one substituent group, they can be the same or different. The organic substituent groups can comprise from 1 to 12 carbon atoms, or from 1 to 6 carbon atoms, or from 1 to 4 carbon atoms.

The term "cycloalkenyl" denotes a cycloalkyl radical as defined above that comprises at least one carbon-carbon double bond. Examples include but are not limited to cyclopropenyl, 1-cyclobutenyl, 2-cyclobutenyl, 1-cyclopentenyl, 2-cyclopentenyl, 3-cyclopentenyl, 1-cyclohexyl, 2-cyclohexyl, 3-cyclohexyl and the like. The term "substituted cycloalkenyl" denotes a cycloalkyl as defined above further substituted with one or more groups selected from halogen, alkyl, hydroxyl, alkoxy, substituted alkoxy, haloalkoxy, carboxy, carboalkoxy, alkylcarboxamide, substituted alkylcarboxamide, dialkylcarboxamide, substituted dialkylcarboxamide, amino, mono-substituted amino or di-substituted amino. When the cycloalkenyl is substituted with more than one group, they can be the same or different. The organic substituent groups can comprise from 1 to 12 carbon atoms, or from 1 to 6 carbon atoms, or from 1 to 4 carbon atoms.

The term "alkoxy" as used herein denotes an alkyl residue, defined above, attached directly to a oxygen to form an ether residue. Examples include methoxy, ethoxy, n-propoxy, iso-propoxy, n-butoxy, t-butoxy, iso-butoxy and the like.

The term "substituted alkoxy" denotes an alkoxy residue of the above definition that is substituted with one or more substituent groups, but preferably one or two groups, which include but are not limited to hydroxyl, cycloalkyl, amino, mono-substituted amino, di-substituted amino, acyloxy, nitro, cyano, carboxy, carboalkoxy, alkylcarboxamide, substituted alkylcarboxamide, dialkylcarboxamide, substituted dialkylcarboxamide, alkylsulfonyl, alkylsulfinyl, thioalkyl, thiohaloalkyl, alkoxy, substituted alkoxy or haloalkoxy. When more than one group is present then they can be the same or different. The organic substituent groups can comprise from 1 to 12 carbon atoms, or from 1 to 6 carbon atoms, or from 1 to 4 carbon atoms.

The term "mono-substituted amino" denotes an amino substituted with one organic substituent groups, which include but are not limited to alkyl, substituted alkyl or arylalkyl wherein the terms have the same definitions found hereinabove.

The term "di-substituted amino" denotes an amino residue substituted with two radicals that can be same or different selected from aryl, substituted aryl, alkyl, substituted alkyl or arylalkyl wherein the terms have the same definitions found throughout. Some examples include dimethylamino, methylethylamino, diethylamino and the like.

The term "haloalkyl" denotes a alkyl residue as defined above, substituted with one or more halogens, preferably fluorine, such as a trifluoromethyl, pentafluoroethyl and the like.

The term "haloalkoxy" denotes a haloalkyl residue as defined above, that is directly attached to an oxygen to form trifluoromethoxy, pentafluoroethoxy and the like.

The term "acyl" denotes a R—C(O)— residue containing 1 to 8 carbons. Examples include but are not limited to formyl, acetyl, propionyl, butanoyl, iso-butanoyl, pentanoyl, hexanoyl, heptanoyl, benzoyl and the like.

The term "acyloxy" denotes a an acyl radical as defined above directly attached to an oxygen to form an R—C(O) O— residue. Examples include but are not limited to acetyloxy, propionyloxy, butanoyloxy, iso-butanoyloxy, benzoyloxy and the like.

The term "aryl" denotes a ring radical containing 6 to 18 carbons, or preferably 6 to 12 carbons, having at least one six-membered aromatic "benzene" residue therein. Examples of such aryl radicals include phenyl and naphthyl. The term "substituted aryl" denotes an aryl ring radical as defined above that is substituted with one or more, or preferably 1, 2, or 3 organic or inorganic substituent groups, which include but are not limited to a halogen, alkyl, substituted alkyl, hydroxyl, cycloalkyl, amino, mono-substituted amino, di-substituted amino, acyloxy, nitro, cyano, carboxy, carboalkoxy, alkylcarboxamide, substituted alkylcarboxamide, dialkylcarboxamide, substituted dialkylcarboxamide, alkylsulfonyl, alkylsulfinyl, thioalkyl, thiohaloalkyl, alkoxy, substituted alkoxy or haloalkoxy, aryl, substituted aryl, heteroaryl, heterocyclic ring, substituted heterocyclic ring wherein the terms are defined herein. The organic substituent groups can comprise from 1 to 12 carbon atoms, or from 1 to 6 carbon atoms, or from 1 to 4 carbon atoms.

The term "heteroaryl" denotes an aryl ring radical as defined above, wherein at least one of the carbons, or preferably 1, 2, or 3 carbons of the aryl aromatic ring has been replaced with a heteroatom, which include but are not limited to nitrogen, oxygen, and sulfur atoms. Examples of heteroaryl residues include pyridyl, bipyridyl, furanyl, and thiofuranyl residues. Substituted "heteroaryl" residues can have one or more organic or inorganic substituent groups, or preferably 1, 2, or 3 such groups, as referred to herein-above for aryl groups, bound to the carbon atoms of the heteroaromatic rings. The organic substituent groups can comprise from 1 to 12 carbon atoms, or from 1 to 6 carbon atoms, or from 1 to 4 carbon atoms.

The term "halo" or "halogen" refers to a fluoro, chloro, bromo or iodo group.

The term "thioalkyl" denotes a sulfide radical containing 1 to 8 carbons, linear or branched. Examples include methylsulfide, ethyl sulfide, isopropylsulfide and the like.

The term "thiohaloalkyl" denotes a thioalkyl radical substituted with one or more halogens. Examples include trifluoromethylthio, 1,1-difluoroethylthio, 2,2,2-trifluoroethylthio and the like.

The term "carboalkoxy" refers to an alkyl ester of a carboxylic acid, wherein alkyl has the same definition as found above. Examples include carbomethoxy, carboethoxy, carboisopropoxy and the like.

The term "alkylcarboxamide" denotes a single alkyl group attached to the amine of an amide, wherein alkyl has the same definition as found above. Examples include N-methylcarboxamide, N-ethylcarboxamide, N-(iso-propyl) carboxamide and the like. The term "substituted alkylcarboxamide" denotes a single "substituted alkyl" group, as defined above, attached to the amine of an amide.

The term "dialkylcarboxamide" denotes two alkyl or arylalkyl groups that are the same or different attached to the amine of an amide, wherein alkyl has the same definition as found above. Examples of a dialkylcarboxamide include N,N-dimethylcarboxamide, N-methyl-N-ethylcarboxamide and the like. The term "substituted dialkylcarboxamide" denotes two alkyl groups attached to the amine of an amide, where one or both groups is a "substituted alkyl", as defined above. It is understood that these groups can be the same or different. Examples include N,N-dibenzylcarboxamide, N-benzyl-N-methylcarboxamide and the like.

The term "arylalkyl" defines an alkylene, such as —CH$_2$— for example, which is substituted with an aryl group that can be substituted or unsubstituted as defined above. Examples of an "arylalkyl" include benzyl, phenethylene and the like.

A residue of a chemical species, as used in the specification and concluding claims, refers to a structural fragment, or a moiety that is the resulting product of the chemical species in a particular reaction scheme or subsequent formulation or chemical product, regardless of whether the structural fragment or moiety is actually obtained from the chemical species. Thus, an ethylene glycol residue in a polyester refers to one or more —OCH₂CH₂O— repeat units in the polyester, regardless of whether ethylene glycol is used to prepare the polyester. Similarly, a 2,4-thiazolidinedione residue in a chemical compound refers to one or more -2,4-thiazolidinedione moieties of the compound, regardless of whether the residue was obtained by reacting 2,4-thiazolidinedione to obtain the compound.

The term "organic residue" defines a carbon containing residue, i.e. a residue comprising at least one carbon atom, and includes but is not limited to the carbon-containing groups, residues, or radicals defined hereinabove. Organic residues can contain various heteroatoms, or be bonded to another molecule through a heteroatom, including oxygen, nitrogen, sulfur, phosphorus, or the like. Examples of organic residues include but are not limited alkyl or substituted alkyls, alkoxy or substituted alkoxy, mono or di-substituted amino, amide groups, etc. Organic resides can preferably comprise 1 to 18 carbon atoms, 1 to 15, carbon atoms, 1 to 12 carbon atoms, 1 to 8 carbon atoms, or 1 to 4 carbon atoms.

A very close synonym of the term "residue" is the term "radical," which as used in the specification and concluding claims, refers to a fragment, group, or substructure of a molecule described herein, regardless of how the molecule is prepared. For example, a 2,4-thiazolidinedione radical in a particular compound has the structure

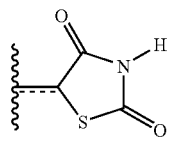

regardless of whether thiazolidinedione is used to prepare the compound. In some embodiments the radical (for example an alkyl) can be further modified (i.e., substituted alkyl) by having bonded thereto one or more "substituent radicals." The number of atoms in a given radical is not critical to the present invention unless it is indicated to the contrary elsewhere herein.

"Inorganic radicals," as the term is defined and used herein contain no carbon atoms and therefore comprise only atoms other than carbon. Inorganic radicals comprise bonded combinations of atoms selected from hydrogen, nitrogen, oxygen, silicon, phosphorus, sulfur, selenium, and halogens such as fluorine, chlorine, bromine, and iodine, which can be present individually or bonded together in their chemically stable combinations. Inorganic radicals have 10 or fewer, or preferably one to six or one to four inorganic atoms as listed above bonded together. Examples of inorganic radicals include, but not limited to, amino, hydroxy, halogens, nitro, thiol, sulfate, phosphate, and like commonly known inorganic radicals. The inorganic radicals do not have bonded therein the metallic elements of the periodic table (such as the alkali metals, alkaline earth metals, transition metals, lanthamide metals, or actinide metals), although such metal ions can sometimes serve as a pharmaceutically acceptable cation for anionic inorganic radicals such as a sulfate, phosphate, or like anionic inorganic radical. Inorganic radicals do not comprise metalloids elements such as boron, aluminum, gallium, germanium, arsenic, tin, lead, or tellurium, or the noble gas elements, unless otherwise specifically indicated elsewhere herein.

"Organic radicals" as the term is defined and used herein contain one or more carbon atoms. An organic radical can have, for example, 1–26 carbon atoms, 1–18 carbon atoms, 1–12 carbon atoms, 1–8 carbon atoms, or 1–4 carbon atoms. Organic radicals often have hydrogen bound to at least some of the carbon atoms of the organic radical. One example, of an organic radical that comprises no inorganic atoms is a 5,6,7,8-tetrahydro-2-naphthyl radical. In some embodiments, an organic radical can contain 1–10 inorganic heteroatoms bound thereto or therein, including halogens, oxygen, sulfur, nitrogen, phosphorus, and the like. Examples of organic radicals include but are not limited to an alkyl, substituted alkyl, cycloalkyl, substituted cycloalkyl, mono-substituted amino, di-substituted amino, acyloxy, cyano, carboxy, carboalkoxy, alkylcarboxamide, substituted alkylcarboxamide, dialkylcarboxamide, substituted dialkylcarboxamide, alkylsulfonyl, alkylsulfinyl, thioalkyl, thiohaloalkyl, alkoxy, substituted alkoxy, haloalkyl, haloalkoxy, aryl, substituted aryl, heteroaryl, heterocyclic, or substituted heterocyclic radicals, wherein the terms are defined elsewhere herein. A few non-limiting examples of organic radicals that include heteroatoms include alkoxy radicals, trifluoromethoxy radicals, acetoxy radicals, dimethylamino radicals and the like.

The term "amide" as defined hereby and used in the instant specification refers to a functional group or residue that contains a carbonyl (CO) group bound to a nitrogen atom, i.e. a residue having the formula:

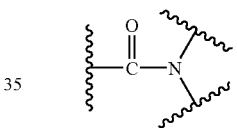

It is to be understood that for the purposes of this disclosure and the accompanying claims, any molecule or compound that comprises the above functional group or reside can be termed an amide, regardless of the identity of the three unspecified substituent groups. For example, if the carbonyl carbon and one of the unspecified nitrogen substituents are bound to carbon atoms, the resulting compound would be described herein as an "amide." Nevertheless, if the substituent of the carbonyl group were a $2^{nd}$ nitrogen atom, as shown below, the resulting compound would still be termed an "amide" herein, even though many of ordinary skill in the art might often use a more specific term, such as "urea." Similarly, if the substituent of the carbonyl group were an oxygen atom, the compound would still be termed an amide herein, even though the more specific term "urethane" might alternatively be employed.

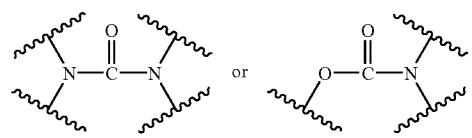

Compounds of the Invention

Some disclosed embodiments of the invention relate to a genus of compounds of Formula (200):

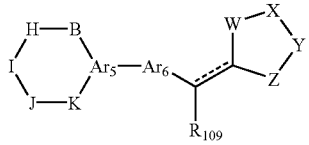
(200)

wherein:
a) the B, H, I, J and K residues are independently selected from —C(O)—, —C(S)—, —O—, —S—, —N(R$_{101}$)—, —N(R$_{102}$)—, —C(R$_{103}$)(R$_{104}$)—, —C(R$_{105}$)(R$_{106}$)—, or —C(R$_{107}$)(R$_{108}$)— residues, and from zero to two of the B, H, I, J or K residues can be absent; wherein:
  i) R$_{101}$, R$_{102}$, R$_{103}$, R$_{104}$, R$_{105}$, R$_{106}$, R$_{107}$ and R$_{108}$ are independently selected from hydrogen, hydroxyl, a halogen, amino, or an organic residue comprising 1 to 12 carbon atoms; or two of the R$_{101}$, R$_{102}$, R$_{103}$, R$_{104}$, R$_{105}$, R$_{106}$, R$_{107}$ and R$_{108}$ residues can be connected together to form an exocyclic substituent residue comprising 1 to 6 ring carbon atoms and from 0 to 3 optional ring heteroatoms selected from O, S, or N; and
  ii) B, H, I, J and K together with the Ar$_5$ form a ring containing at least one amide residue having the formula

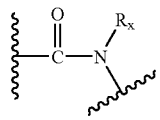

wherein R$_5$ is a R$_{101}$ or R$_{102}$ residue;
b) Ar$_5$ is an aryl, substituted aryl, heteroaryl, or substituted heteroaryl residue comprising from 3 to 6 ring carbon atoms and from 0 to 3 optional ring heteroatoms selected from O, S, or N;
c) Ar$_6$ is an aryl, substituted aryl, heteroaryl, or substituted heteroaryl residue comprising from 2 to 6 ring carbon atoms and from 0 to 3 optional ring heteroatoms selected from O, S, or N;
d) R$_{109}$ is hydrogen, hydroxy, or an organic residue comprising 1 to 10 carbon atoms;
e) ----- is either present or absent;
f) W, X, Y and Z are independently or together —C(O)—, —C(S)—, —S—, —O— or —NH—, to form a 2,4-thiazolidinedione, 2-thioxo-thiazolidine-4-one, 2,4-imidazolidinedione or 2-thioxo-imidazolidine-4-one residue; or a pharmaceutically acceptable salt thereof.

In the embodiments described immediately above, the W, X, Y and Z radicals, together with a carbon atom, form one of four separate five membered heterocycles, selected from a 2,4-thiazolidinedione, 2-thioxo-thiazolidine-4-one, 2,4-imidazolidinedione or 2-thioxo-imidazolidine-4-one residue, as shown in the drawing below:

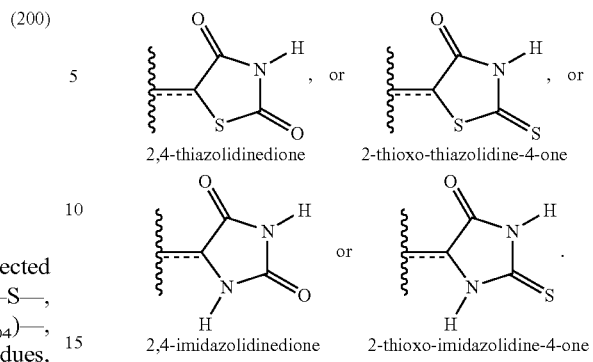

2,4-thiazolidinedione    2-thioxo-thiazolidine-4-one 2,4-imidazolidinedione    2-thioxo-imidazolidine-4-one For purposes of ease of reference and brevity, the 2,4-thiazolidinedione, 2-thioxo-thiazolidine-4-one, 2,4-imidazolidinedione or 2-thioxo-imidazolidine-4-one heterocyclic residues can be generically termed an "HAr" heterocyclic residue or radical. When the "HAr" terminology is employed, an alternative description embodying the invention, which is closely related to the genus of compounds of formula 200 described above can be recited. This alternative description relates to a genus of compounds having the structure

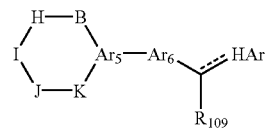

wherein
a) Ar$_5$ is an aryl, substituted aryl, heteroaryl, or substituted heteroaryl;
b) B, H, I, J and K are independently selected from —C(O)—, —C(S)—, —O—, —S—, —N(R$_{101}$)—, —N(R$_{102}$)—, —C(R$_{103}$)(R$_{104}$)—, —C(R$_{105}$)(R$_{106}$)—, or —C(R$_{107}$)(R$_{108}$)—, wherein one, or two of B, H, I, J or K can optionally be absent; and
  i) R$_{101}$, R$_{102}$, R$_{103}$, R$_{104}$, R$_{105}$, R$_{106}$, R$_{107}$ and R$_{108}$ are independently selected from hydrogen, hydroxyl, a halogen, amino, or an organic radical comprising 1 to 12 carbon atoms;
  ii) two of B, H, I, J and K form at least one radical having the structure

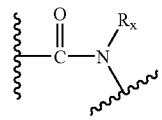

wherein R$_x$ is a R$_{101}$ or R$_{102}$ radical;
  iii) Ar$_5$ together with B, H, I, J and K comprise from 2 to 24 carbon atoms;
c) Ar$_6$ is an aryl, substituted aryl, heteroaryl, or substituted heteroaryl comprising from 2 to 18 carbon atoms;
d) R$_{109}$ is hydrogen, hydroxy, or an organic radical comprising 1 to 10 carbon atoms;
e) ----- is either present or absent;
f) HAr is a heterocycle having the structure

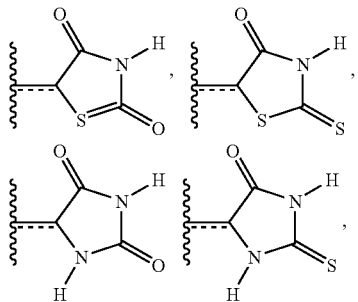

or a pharmaceutically acceptable salt thereof.

The detailed description of the preferred embodiments recited below is intended to be applicable, to the extent reasonably possible, to either of the two alternative descriptions of the compounds of the invention cited immediately above.

$Ar_5$ is an aryl, substituted aryl, heteroaryl, or substituted heteroaryl residue or radical. As noted in the accompanying definitions, aryl radicals have at least one six-membered aromatic "benzene" residue therein, although additional aromatic rings might be attached thereto, so as to form, for example, a naphthalene or biphenyl radical. The aryl ring residues are bonded to the $Ar_6$ radical, and have bonded thereto a non-aromatic ring residue comprising one or more of the B, H, I, J and K residues. In many embodiments, $Ar_5$ is a benzene radical, which can be optionally additionally substituted with one or more additional organic or inorganic radicals or residues.

$Ar_5$ can also comprise a heteroaryl radical or residue, wherein the term is defined elsewhere herein. The heteroaryl ring residue is bonded to the $Ar_6$ radical and a non-aromatic heterocyclic ring residue comprising one or more of the B, H, I, J and K residues. In many embodiments, $Ar_5$ comprises a pyridine, pyrimidine, or pyrazine ring.

The aryl or heteroaryl ring residues can optionally and additionally have one, two, or more additional substituent residues or radicals bonded to the aryl or heteroaryl rings, so as to comprise a "substituted aryl" or "substituted heteroaryl" residue or radical, as the terms are defined elsewhere herein. The additional substituents can be selected from organic residues, inorganic radicals, or organic radicals as those terms are defined elsewhere herein. In some embodiments, the $Ar_5$ aryl or heteroaryl ring is substituted with one or two additional substituents independently selected from a halogen, an amino, or a radical comprising 1 to 4 carbon atoms selected from an alkyl, a monosubstituted amino, a di substituted amino, an alkoxy, or a haloalkoxy.

In some embodiments, $Ar_5$ is a benzene ring, optionally substituted with one additional substituent selected from a halogen, an amino, or a radical comprising 1 to 4 carbon atoms selected from an alkyl, a monosubstituted amino, a disubstituted amino, an alkoxy, or a haloalkoxy. An example of a substituted $Ar_5$ radical comprising a benzene ring and one additional substituent would be a radical having the structure shown below, wherein $R_a$ is the additional substituent residue or radical.

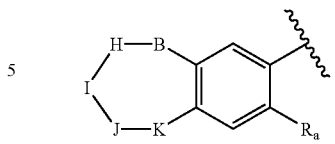

As is also shown in the drawing immediately above, and elsewhere herein, the $Ar_5$ radical is also bonded to a non-aromatic heterocyclic ring residue comprising one or more of the B, H, I, J and K residues, wherein the non-aromatic heterocyclic ring residue is bound to adjacent carbon atoms on the $Ar_5$ aryl or heteroaryl ring. One or two of the B, H, I, J and K residues can optionally be absent. Therefore, the non-aromatic heterocyclic ring residue can form five, six, or seven membered rings, wherein the carbons that are part of the $Ar_5$ aryl or heteroaryl ring are also considered to be part of the non-aromatic heterocyclic ring residue.

The B, H, I, J and K residues are independently selected from —C(O)—, —C(S)—, —O—, —S—, —N($R_{101}$)—, —N($R_{102}$)—, —C($R_{103}$)($R_{104}$)—, —C($R_{105}$)($R_{106}$)—, or —C($R_{107}$)($R_{108}$)— residues, with the proviso that two of B, H, I, J and K must form an amide residue, as will be further discussed below. $R_{101}$, $R_{102}$, $R_{103}$, $R_{104}$, $R_{105}$, $R_{106}$, $R_{107}$ and $R_{108}$ can be independently selected from hydrogen, hydroxyl, a halogen, amino, or an organic radicals. In many embodiments, suitable organic radicals for $R_{101}$, $R_{102}$, $R_{103}$, $R_{104}$, $R_{105}$, $R_{106}$, $R_{107}$ and $R_{108}$ comprise 1 to 12 carbon atoms, 1 to 6 carbon atoms, or 1 to 4 carbon atoms. In some embodiments, lower alkyl radicals such as methyl, ethyl, n-propyl, i-propyl, n-butyl, i-butyl, and t-butyl are particularly suitable $R_{101}$, $R_{102}$, $R_{103}$, $R_{104}$, $R_{105}$, $R_{106}$, $R_{107}$ or $R_{108}$ substituents.

Although not wishing to be bound by theory, the heterocyclic amide compounds of the invention, including the $Ar_5$ radical together with the non-aromatic heterocyclic ring residue and any additional substituent radicals for $Ar_5$ are selected so that the $Ar_5$ radical has a geometry, size, and polarity that is suitable to allow the compounds of the invention to interact with and substantially fill, yet fit within the binding regions of the target biological molecules, so as to contribute to the effective binding of the compounds to the binding sites in the biological target molecules. Therefore, in some embodiments, the $Ar_5$ radical, together with the non-aromatic heterocyclic ring residue and any additional substituent radicals for $Ar_5$ comprises from 2 to 24 carbon atoms, or from 3 to 20 carbon atoms, or from 4 to 18 carbon atoms, or from 5 to 16 carbon atoms.

It must be noted that for all the compounds of the invention, the B, H, I, J and K residues together with the $Ar_5$ form a non-aromatic heterocyclic ring containing at least one amide residue. The amide residues as defined elsewhere herein for the purposes of this disclosure have the structure indicated below, wherein $R_x$ is a $R_{101}$ or $R_{102}$ residue.

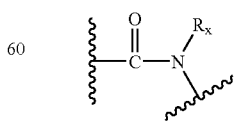

The amide residue is contained within the non-aromatic heterocyclic ring comprising B, H, I, J and K. Therefore, in one embodiment of the invention, ring radical comprising the Ar$_5$ ring and the non-aromatic heterocyclic ring comprising B, H, I, J and K would have the structure shown immediately below:

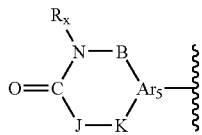

wherein R$_x$ is a R$_{101}$, or R$_{102}$ residue. In such embodiments, the J atom or residue could be one of several alternatives. If the J atom or residue was a —C(R$_{103}$)(R$_{104}$)— residue, the resulting structure would be:

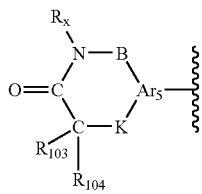

Such cyclic compounds comprising an amide group whose carbonyl carbon is bound to another carbon are often termed "lactams."

Alternatively, if J is an oxygen atom, the resulting compounds are termed "cyclic carbamates", and would have the structure:

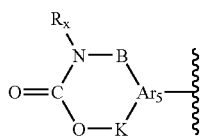

If the J atom or residue is an —N(R$_{102}$)— residue, the resulting compounds are termed a "cyclic urea," and would have the structure:

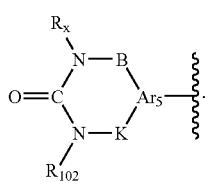

It is to be understood that in the various embodiments described above, 0, 1, or 2, of the B, H, I, J or K residues could be absent. Typically the B and K residues are bound to two adjacent carbon atoms on the Ar$_5$ aryl or heteroaryl ring. Therefore the ring comprising the B, H, I, J and K residues often comprise 5, 6, or 7 ring atoms and the B, H, I, J and K residues form at least one amide residue.

In some embodiments B, H, I, J and K together with Ar$_5$ form a ring containing at least one amide residue having one of the Formulas (205a–k) wherein Ar$_5$ is benzene or a substituted benzene radical. Similar structures can also be formed where Ar$_5$ is a heteroaryl, such as pyridine, pyrimidene, pyrazine, and the like:

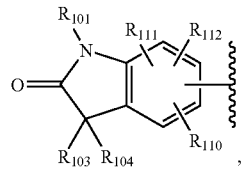
(205a)

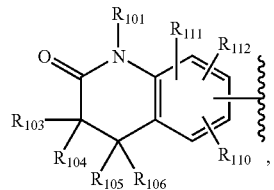
(205b)

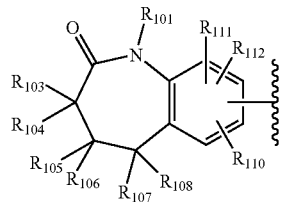
(205c)

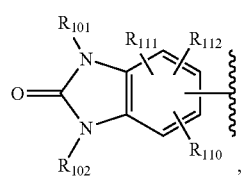
(205d)

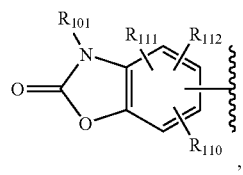
(205e)

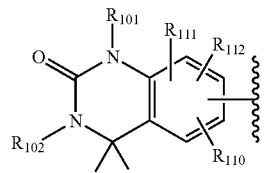
(205f)

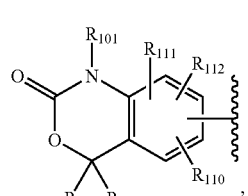
(205g)

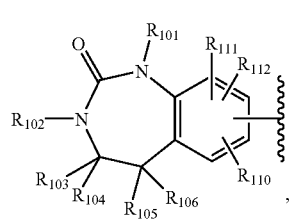
(205h)

-continued

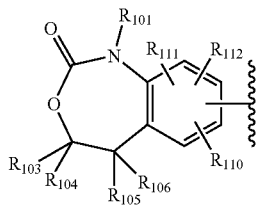
(205i)

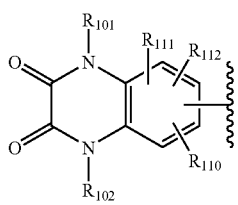
(205j)

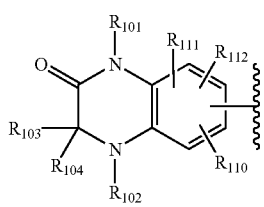
(205k)

In the drawing above, $R_{101}$, $R_{102}$, $R_{103}$, $R_{104}$, $R_{105}$, $R_{106}$, $R_{107}$, $R_{108}$, $R_{110}$, $R_{111}$ or $R_{112}$ can be independently selected from inorganic substituents, which include but are not limited to inorganic substituents such as hydrogen, halogen, cyano, nitro, hydroxyl, or amino. $R_{101}$, $R_{102}$, $R_{103}$, $R_{104}$, $R_{105}$, $R_{106}$, $R_{107}$, $R_{108}$, $R_{110}$, $R_{111}$ or $R_{112}$ can also be independently selected from organic residues or organic radicals, as those terms are defined elsewhere herein. Examples of suitable organic residues or radicals include but are not limited to an alkyl, substituted alkyl, haloalkyl, alkenyl, substituted alkenyl, alkynyl, substituted alkynyl, acyloxy, amino, mono-substituted amino, di-substituted amino, alkylsulfonamide, arylsulfonamide, alkylurea, arylurea, alkylcarbamate, arylcarbamate, aryl, heteroaryl, alkoxy, substituted alkoxy, haloalkoxy, thioalkyl, thiohaloalkyl, carboxy, carboalkoxy, alkylcarboxamide, substituted alkylcarboxamide, dialkylcarboxamide or substituted dialkylcarboxamide residue. In some embodiments, preferred $R_{101}$, $R_{102}$, $R_{103}$, $R_{104}$, $R_{105}$, $R_{106}$, $R_{107}$, $R_{108}$, $R_{110}$, $R_{111}$ or $R_{112}$ groups are an alkyl, substituted alkyl, haloalkyl, alkoxy, substituted alkoxy, or haloalkoxy residues, particularly those comprising from 1 to 12 carbons, 1 to 6 carbons, or 1 to four carbons.

In some embodiments, the residue bonded to the nitrogen atom of the amide groups (i.e. $R_{101}$ or $R_{102}$) can hydrogen or an organic radical comprising 1 to 12 carbon atoms, 1 to 8 carbon atoms, or 1 to 4 carbon atoms. In some embodiments, $R_{101}$ or $R_{102}$ is a lower alkyl group, such as methyl, ethyl, n-propyl, i-propyl, n-butyl, i-butyl, or t-butyl. In some embodiments, methyl, ethyl, or i-propyl radicals are preferred $R_{101}$ or $R_{102}$ residues.

Some embodiments of the invention relate to lactam compounds of Formula (206):

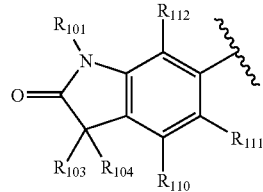
(206)

Some embodiments of the invention relate to lactam compounds of Formula (207):

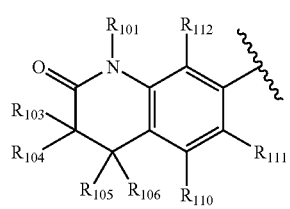
(207)

Some embodiments of the invention relate to compounds of Formula (208):

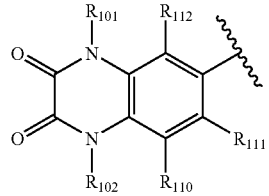
(208)

In some embodiments $R_{101}$ is hydrogen, alkyl or substituted alkyl. Some examples $R_{101}$ is a straight or branched alkyl of $C_1$–$C_{12}$. In other examples $R_{101}$ is a straight or branched alkyl of $C_1$–$C_8$. In still other examples $R_{101}$ is a straight or branched alkyl of $C_1$–$C_6$. In yet other examples $R_{101}$ is a straight or branched alkyl of $C_1$–$C_4$.

Some embodiments of the invention relate to compounds of Formula (200) wherein the two R substituents of —C($R_{103}$)($R_{104}$)—, —C($R_{105}$)($R_{106}$)—, or —C($R_{107}$)($R_{108}$)—, together form an exocyclic cycloalkyl ring, which can optionally contain O, S or N-alkyl atom groups within the ring. In many embodiments, the exocyclic cycloalkyl ring comprises from 3 to 6 ring carbon atoms. Representative examples include cyclopropyl, cyclobutyl, cyclopentyl, and cyclohexyl exocyclic rings. Representative examples of compounds comprising a five membered lactam ring wherein —C($R_{103}$)($R_{104}$)— together form an exocyclic cycloalkyl, include those of Formulae (209a–c).

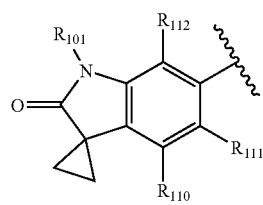
(209a)

-continued

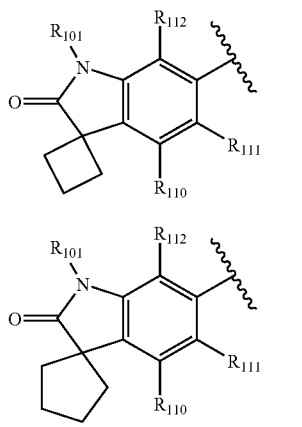

(209b)

(209c)

One or two of the carbons of the exocyclic rings could optionally be replaced with an O, S or N-alkyl residue, to form tetrahydrofuranyl, tetrahydropyrrolidinyl, and tetrahydrothiofuranyl and like exocyclic ring radicals.

Some embodiments of the invention relate to compounds wherein —C($R_{105}$)($R_{106}$)— form an exocyclic cycloalkyl optionally substituted with O, S or N-alkyl. Representative examples of compounds for (205b) wherein —C($R_{103}$)($R_{104}$)— together form a cycloalkyl optionally substituted with O, S or N-alkyl include those of Formulae (209d–f).

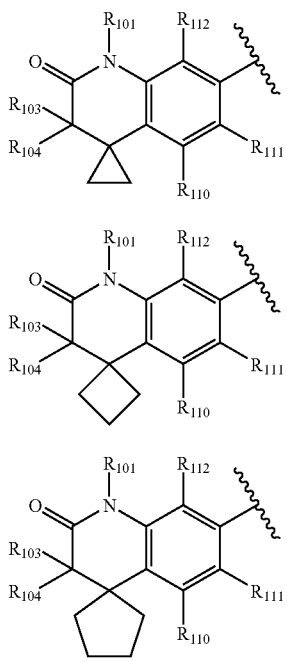

(209d)

(209e)

(209f)

Some embodiments of the invention relate to compounds of Formula (200) wherein —C($R_{107}$)($R_{108}$)— form a cycloalkyl optionally substituted with O, S or N-alkyl.

Some embodiments of the invention relate to compounds of Formula (200) where —C($R_{103}$)($R_{104}$)—, —C($R_{105}$)($R_{106}$)— and —C($R_{107}$)($R_{108}$)— independently form a cycloalkyl optionally substituted with O, S or N-alkyl.

In some embodiments $R_{101}$ is a substituted alkyl that include aryl alkyl, substituted-aryl alkyl and heteroaryl alkyl. Some representative examples are of the Formulae (210a–b):

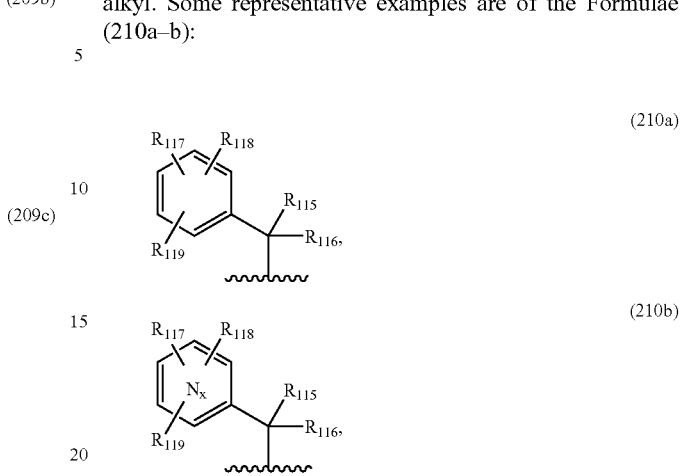

(210a)

(210b)

wherein $R_{115}$, $R_{116}$, $R_{117}$, $R_{118}$ and $R_{119}$ are independently or together hydrogen, alkyl, substituted alkyl, haloalkyl, alkenyl, substituted alkenyl, alkynyl, substituted alkynyl, halogen, cyano, nitro, hydroxyl, acyloxy, amino, mono-substituted amino, di-substituted amino, alkylsulfonamide, arylsulfonamide, alkylurea, arylurea, alkylcarbamate, arylcarbamate, heteroaryl, alkoxy, substituted alkoxy, haloalkoxy, thioalkyl, thiohaloalkyl, carboxy, carboalkoxy, alkylcarboxamide, substituted alkylcarboxamide, dialkylcarboxamide or substituted dialkylcarboxamide; and $N_x$ represent the number of nitrogen in the ring wherein x is 1, 2 or 3 thus forming a substituted or unsubstituted pyridyl, pyrimidinyl or triazinyl respectively.

In some embodiments $R_{101}$ is a substituted alkyl that include heteroaryl alkyl. Some interesting heteroaryl residues are five membered rings, some examples include, but are not limited to those of the Formulae (212a–x):

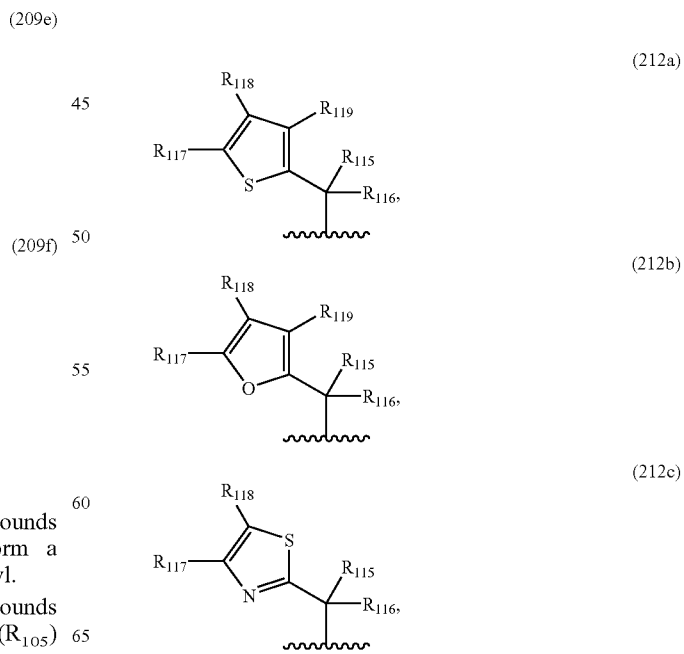

(212a)

(212b)

(212c)

-continued
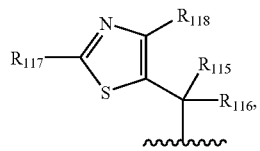
(212d)
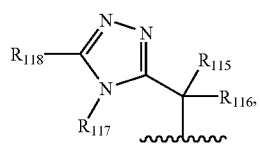
(212e)
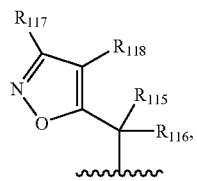
(212f)
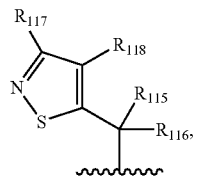
(212g)
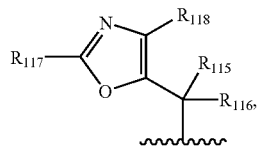
(212h)
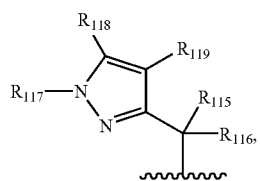
(212i)
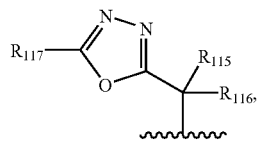
(212j)
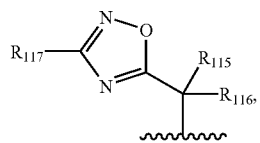
(212k)
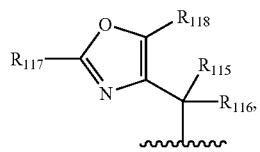
(212l)
-continued
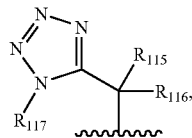
(212m)
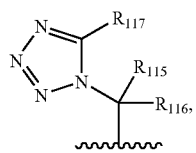
(212n)
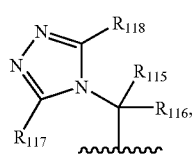
(212o)
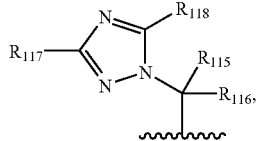
(212p)
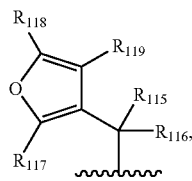
(212q)
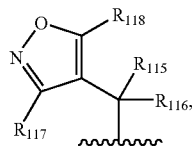
(212r)
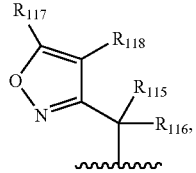
(212s)
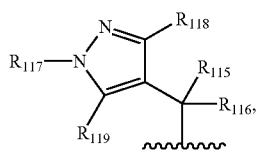
(212t)
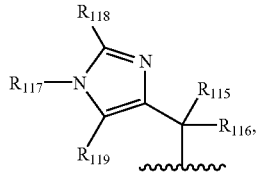
(212u)

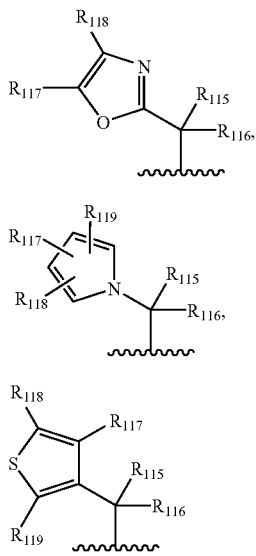

(212v)

(212w)

(212x)

wherein $R_{115}$, $R_{116}$, $R_{117}$, $R_{118}$ and $R_{19}$ are independently or together hydrogen, alkyl, substituted alkyl, haloalkyl, alkenyl, substituted alkenyl, alkynyl, substituted alkynyl, halogen, cyano, nitro, hydroxyl, acyloxy, amino, mono-substituted amino, di-substituted amino, alkylsulfonamide, substituted alkylsulfonamide, arylsulfonamide, heteroarylsulfonamide, alkylurea, alkylthiourea, arylurea, acyl, substituted acyl, alkylcarbamate, arylcarbamate, alkylthiocarbamate, substituted alkylthiocarbamate, arylthiocarbamate, heteroaryl, substituted heteroaryl, alkoxy, substituted alkoxy, haloalkoxy, thioalkyl, alkylsulfoxide, alkylsulfonyl, thiohaloalkyl, carboxy, carboalkoxy, alkylcarboxamide, substituted alkylcarboxamide, dialkylcarboxamide or substituted dialkylcarboxamide.

It is understood that compounds of Formula (200) possessing heteroaryl residues wherein N—$R_{222}$ is a hydrogen, that tautomers are possible and are within the scope of the invention. For example, triazole (212e) can exist in several tautomeric forms when $R_{117}$ is hydrogen. These forms can be represented as shown:

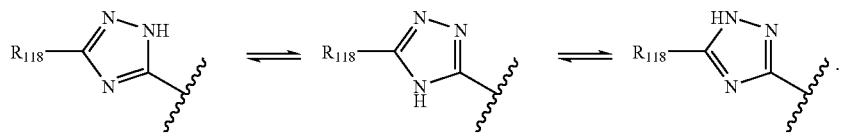

Other represented structures that can exist as various tautomeric forms include, for example, (212i), (212m), (212t) and (212u).

The compounds of the invention comprise an $Ar_6$ ring radical which is an aryl, substituted aryl, heteroaryl, or substituted heteroaryl residue, as those terms are defined elsewhere herein. $Ar_6$ is bonded to the aromatic ring of $Ar_5$, and to a carbon atom that bridges and is bonded to the HAr heterocycle.

The atoms comprising the aromatic ring of $Ar_6$ can optionally be bonded to one, two, three, or four ring substituents, so as to form a substituted aryl or substituted heteroaryl ring, as those terms are defined elsewhere herein.

The optional substituent residues or radicals bonded to $Ar_6$ can be selected from inorganic or organic radicals, as those terms are defined elsewhere herein. Although not wishing to be bound by theory, the heterocyclic amide compounds of the invention, including the $Ar_6$ radical together with any additional substituent radicals are selected so that the $Ar_6$ radical has a geometry, size, and polarity that is suitable to allow the compounds of the invention to interact with and substantially fill, yet fit within, the binding regions of the target biological molecules, so as to contribute to the effective binding of the compounds to the binding sites in the biological target molecules. Therefore, in some embodiments, the $Ar_6$ aryl or heteroaryl radical, together any additional substituent radicals for comprises from 2 to 18 carbon atoms, or from 3 to 12 carbon atoms, or from 4 to 10 carbon atoms, or from 5 to 8 carbon atoms.

In many embodiments, $Ar_6$ is a substituted or unsubstituted six membered aromatic or heteroaromatic radical, such as a benzene, pyridine, pyrimidine, or pyrazine ring radical. In such embodiments, any relative orientation of the bonds to $Ar_5$ and to the carbon atom that bridges to the HAr heterocycles (i.e. ortho, meta, or para) can be employed. Nevertheless, in some embodiments, a "meta" orientation of the bonds to $Ar_5$ and to the carbon atom that bridges to the HAr heterocycles can provide superior biological activity. Such "meta" $Ar_6$ rings can have additional substituents, as discussed above. In some such embodiments $Ar_6$ has the Formula (215a), (215b), (215c) or (215d):

(215a)

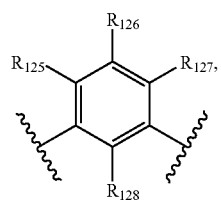

(215b)

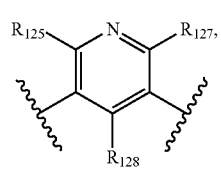

-continued (215c)

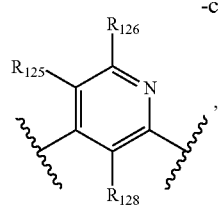

-continued (215d)

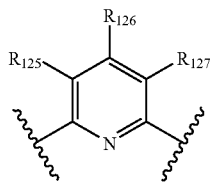

wherein $R_{125}$, $R_{126}$, $R_{127}$ and $R_{128}$ can be independently selected from inorganic substituents which include but are not limited to hydrogen, halogen, nitro, hydroxyl, or amino, or organic residues or radicals, examples of which include but are not limited to an alkyl, substituted alkyl, haloalkyl, alkenyl, substituted alkenyl, alkynyl, substituted alkynyl, cyano, acyloxy, mono-substituted amino, di-substituted amino, alkylsulfonamide, arylsulfonamide, alkylurea, arylurea, alkylcarbamate, arylcarbamate, heteroaryl, alkoxy, haloalkoxy, substituted alkoxy, haloalkoxy, thioalkyl, thiohaloalkyl, carboxy, carboalkoxy, alkylcarboxamide, substituted alkylcarboxamide, dialkylcarboxamide or substituted dialkylcarboxamide residue.

In some compounds of the invention comprising $Ar_6$ rings of formulas (215a–d), $R_{125}$ is not hydrogen. Although the biochemical basis for the effect may not necessarily be well understood, it believed that the presence of a non-hydrogen $R_{125}$ substituent can significantly and unexpectedly improve the activity of the compounds as agents for modulating lipid or carbohydrate metabolism, and/or producing anti-diabetic and/or anti-cholesteric activity. In some embodiments, preferred $R_{125}$, residues are an alkyl, substituted alkyl, haloalkyl, alkoxy, substituted alkoxy, haloalkoxy, halogen, amino, mono-substituted amino, or disubstituted amino residue, particularly those comprising from 1 to 6 carbons, or 1 to four carbons. Unexpectedly good biological activity can often be obtained if $R_{125}$ is a small organic radical such as a methoxy, triflouromethoxy, dimethylamino, or chloride radical, so as to yield an $Ar_6$ radical comprising Formulas (217a), (217b), (217c) or (217d):

(217a)

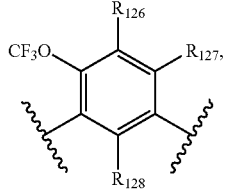

(217b)

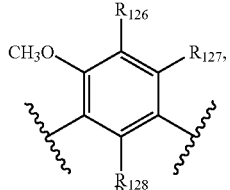

(217c)

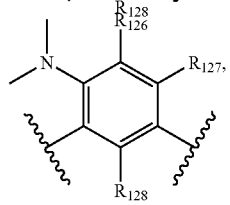

-continued (217d)

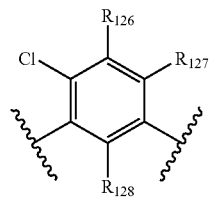

wherein $R_{126}$, $R_{127}$ and $R_{128}$ are independently or together hydrogen or halogen.

The compounds of the invention have a carbon atom bonded to both the $Ar_6$ radical and the HAr heterocyclic radical, so as to bridge or link the $Ar_6$ radical and the HAr heterocyclic radical. The bridging carbon atom bears an $R_{109}$ substituent that can be selected from hydrogen, hydroxy, or an organic residue comprising 1 to 10 carbon atoms. In some embodiments $R_{109}$ is selected from hydrogen, an alkyl, a substituted alkyl, hydroxy, an alkoxy or a haloalkoxy radical. In many embodiments, $R_{109}$ is hydrogen.

In some embodiments ----- represents a bond present and the compound is a benzylidene compound having Formula (220):

(220)

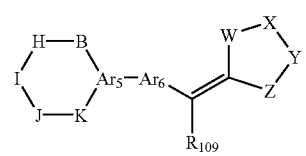

When ----- is present both E and Z configurations of the carbon-carbon bond between the benzylidene carbon and the HAr heterocycle are within the scope of the invention. Either isomer can predominate or be present in pure form, or in a mixture, which may or may not have equal proportions of the E and Z isomers. For example, 2,4-thiazolidinedione and 2-thioxo-4-thiazolidinedione of Formula (200) can have the following structures respectively:

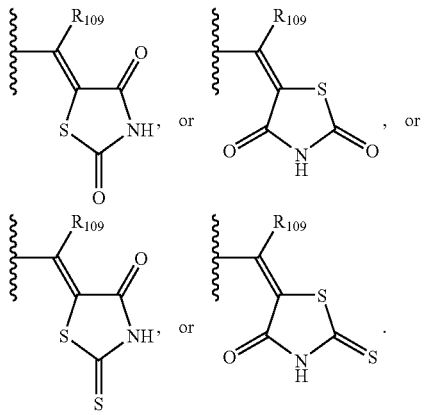

When only one of the two isomer is shown in this specification or in the claims, it should be presumed that both isomers and mixtures thereof are intended unless the context makes it plain that only a single isomer is intended.

In some embodiments ----- represents a bond absent and the compound is a benzyl compound with a single carbon-carbon bond between a benzylic carbon and the HAr ring, the compounds having the Formula (222):

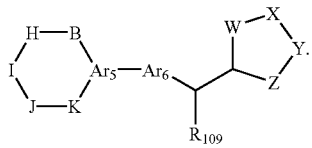

(222)

As already noted above, the 5 membered heterocyclic ring radical comprising the W, X, Y, and Z groups form one of four heterocycles, selected from a 2,4-thiazolidinedione, 2-thioxo-thiazolidine-4-one, 2,4-imidazolidinedione or 2-thioxo-imidazolidine-4-one residue, which can be collectively termed "HAr" heterocycles. The four possible HAr heterocyclic residues are shown in the drawing below:

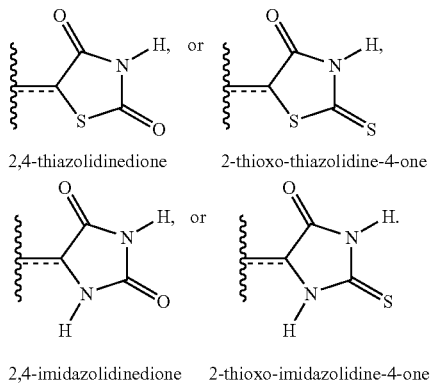

2,4-thiazolidinedione    2-thioxo-thiazolidine-4-one 2,4-imidazolidinedione    2-thioxo-imidazolidine-4-one All four of the HAr heterocycles shown above comprise at least one ring nitrogen atom bonded to a hydrogen atom. The nitrogen-bound hydrogen atoms of all four of the HAr heterocycles are known to be sufficiently acidic so as to react with common laboratory bases such as organic amine compounds, hydroxide salts, and the like.

The acidity of the four HAr heterocycles provides a ready method for preparing salts of the compounds of the invention, by reaction with an appropriate base, so as to generate an anion from the compound of the invention and a cation derived from the base employed. The salts formed by such reactions have the structure

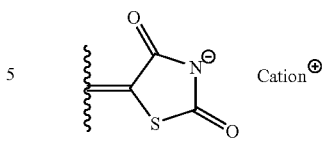

A wide variety of bases could be employed to produce such salts, including monovalent alkali metal hydroxides, divalent alkaline earth metal hydroxides, or bases comprising trivalent metal salts such as aluminum. Alternatively, organic bases such as primary, secondary, or tertiary amines can react with the acidic hydrogens of the compounds of the invention to form ammonium salts. The base and/or its associated cation are chosen so as to provide desirable solubility, toxicity, and/or bioavailability characteristics in the salt after formation of the desired salts. The identity of the base and/or the resulting cation will of course vary somewhat with the identity of the compound of the invention, and the nature of the pharmaceutical composition to be employed and its physical form as a solid or liquid, and the nature of any solvents and/or carriers employed.

Nevertheless, the United States Food and Drug Administration has published a list of pharmaceutically acceptable cations for pharmaceutically acceptable salts that includes aluminum, calcium, lithium, magnesium, potassium, sodium, and zinc cations, ammonium cations formed by the reactions of acidic compounds with benzathine, chloroprocaine, choline, diethanolamine, ethylenediamine, meglumine, procaine, t-butylamine, and tris(hydroxymethyl)aminomethane ("Tris"). Such "pharmaceutically acceptable" salts are often employed and/or evaluated for use in the invention simply because of the likelihood of decreased FDA regulatory scrutiny. Example 25 provides an example of the synthesis of a particularly useful "Tris" salt of one of the compounds of the invention.

Also, one or more compounds disclosed herein can include zwitterionic salts formed by reaction of a nitrogen contained internally within the compound, such as an amine, aniline, substituted aniline, pyridyl and like residues with the acidic hydrogen of the HAr group. Alternatively, a basic nitrogen contained internally within the compound can be reacted with an external acid, such as HCl, sulfuric acid, a carboxylic acid or the like.

Compounds disclosed herein can exist in various tautomeric forms. For example, 2,4-thiazolidinedione-containing compounds disclosed herein can exist in the form of tautomers (224a), (224b) and (224c).

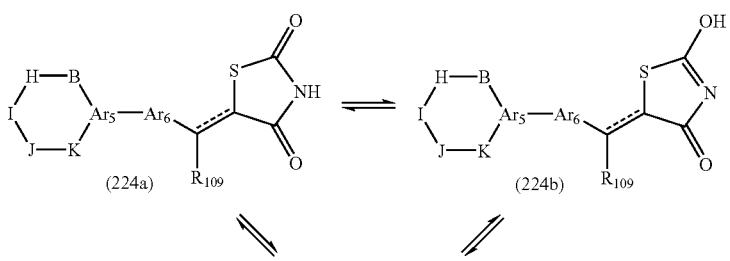

(224a)    (224b)

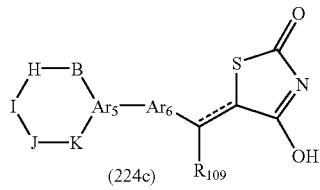

(224c)

It is understood by those of skill in the art that tautomers can also exist with compounds of the invention that contain the heterocycle 2-thioxo-thiazolidine-4-one, 2,4-imidazolidinedione or 2-thioxo-imidazolidine-4-one. For convenience, all of the tautomers can be presented herein by a single formula, but it is understood that all tautomers are within the scope of the invention.

Selected compounds of the invention can also be described more narrowly than the broadest embodiments described above. Two examples of such narrower descriptions are set forth below, but the meanings of the various relevant terms and symbols are intended the same as those same terms and symbols in the description above.

In one narrower description of the invention, the invention relates to a compound having the structure

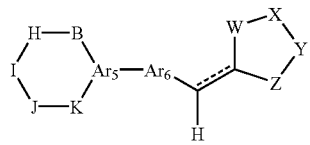

wherein
a) the residue

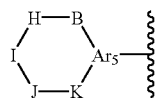

has the structure

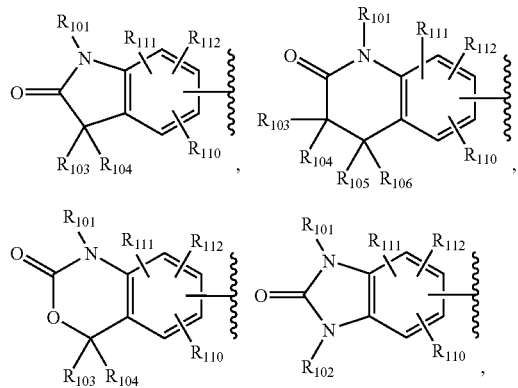

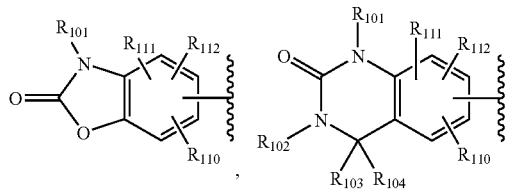

wherein $R_{101}$, $R_{102}$, $R_{103}$, $R_{104}$, $R_{105}$, $R_{106}$, $R_{110}$, $R_{111}$ and $R_{112}$ are independently selected from hydrogen, hydroxyl, a halogen, amino, or an organic residue comprising 1 to 6 carbon atoms;

b) $Ar_6$ has the structure

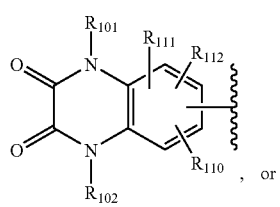 , 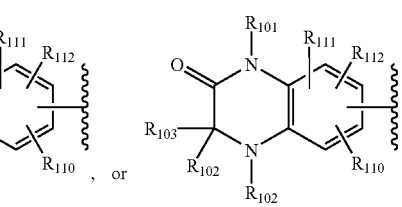 ,

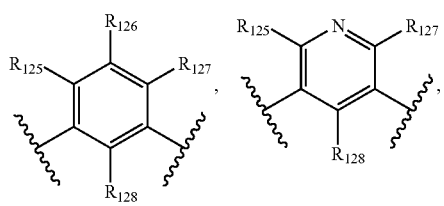 , 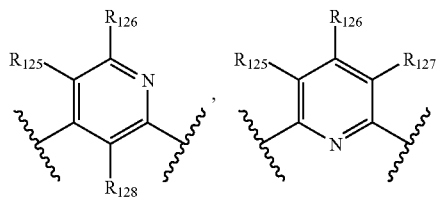

wherein $R_{125}$ is halogen, or an organic substituent residue comprising 1 to 4 carbon atoms selected from alkyl, haloalkyl, cyano, amino, mono-substituted amino, di-substituted amino, alkoxy, or haloalkoxy; and $R_{126}$, $R_{127}$ and $R_{128}$ are independently selected from hydrogen, halogen, amino, and/or organic substituents comprising 1 to 4 carbon atoms selected from alkyl, haloalkyl, cyano, acyloxy, mono-substituted amino, di-substituted amino, alkoxy, or haloalkoxy;

c) ----- is either present or absent; and d) W, X, Y and Z together form a heterocyclic radical having the structure

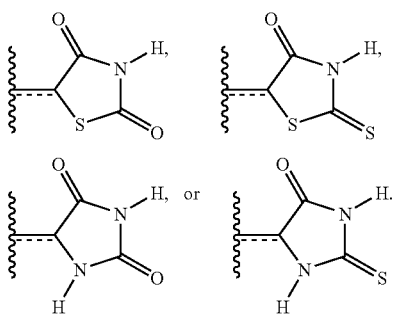

or a pharmaceutically acceptable salt thereof.

In another yet narrower description of the invention, the invention relates to a compound having the structure

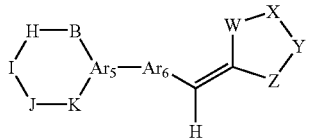

wherein
a) the residue

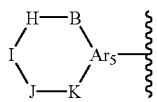

has the structure

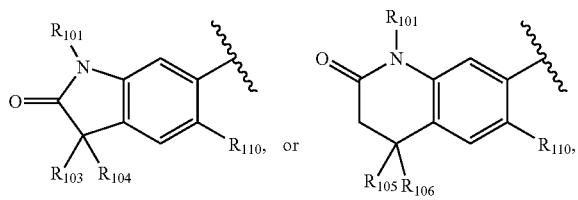

wherein $R_{101}$, $R_{103}$, $R_{104}$, $R_{105}$, $R_{106}$ and $R_{110}$ are independently selected from hydrogen, or an alkyl comprising 1 to 4 carbon atoms.

b) $Ar_6$ has the structure

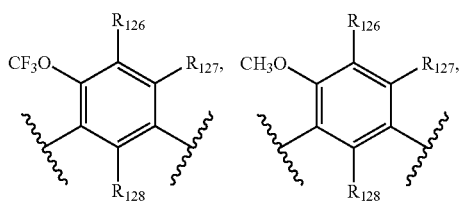

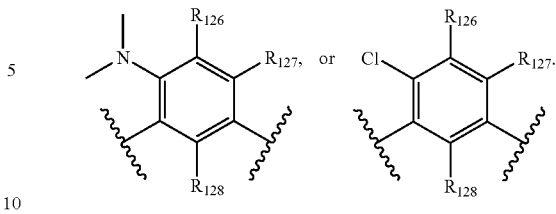

wherein $R_{126}$, $R_{127}$ and $R_{128}$ are independently selected from hydrogen or a halogen; and c) W, X, Y and Z together form a heterocyclic radical having the structure

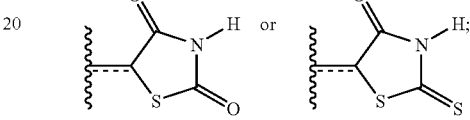

or a pharmaceutically acceptable salt thereof.

The present invention also provides, but is not limited to, the specific species compounds set forth in the Examples, or a pharmaceutically acceptable salt thereof:

Making Compounds of the Invention

Figure 8:
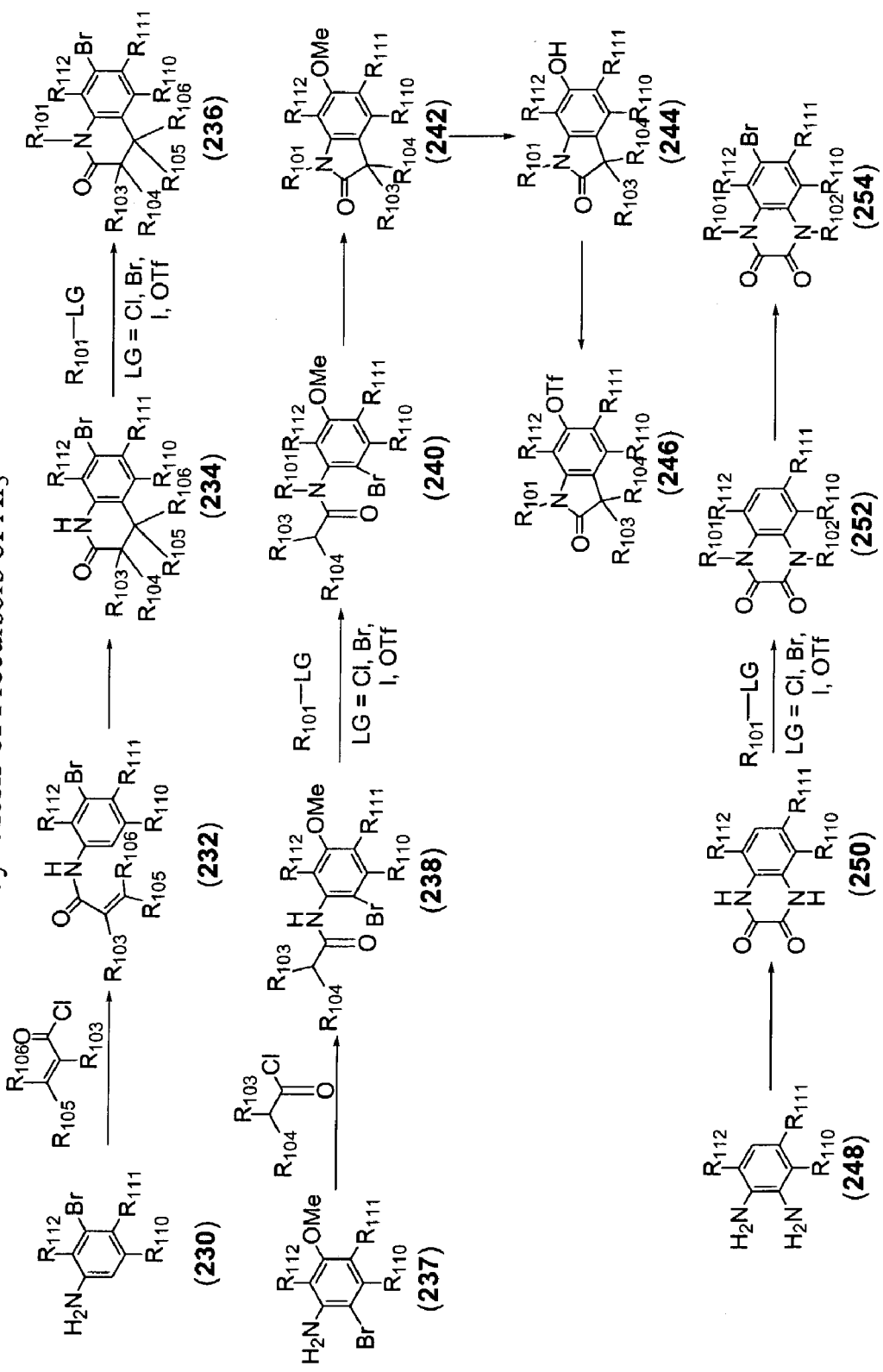
FIG. 8 shows examples of methods for synthesizing precancers of the compounds disclosed herein.

Various synthetic methods can be employed in the making of the compounds disclosed herein. A representative set of synthetic pathways is shown in FIG. 8 for the synthesis of precursors of the $Ar_5$ radical and the attached non-aromatic heterocyclic ring comprising an amide group. The synthetic precursors whose synthesis is shown in FIG. 8 that can be coupled with $Ar_6$ and subsequently elaborated to provide the compounds of the invention by the methods illustrated in FIG. 9.

One method of synthesizing precursors of the $Ar_5$ radical is shown in FIG. 8, and begins with anilines of structure (230), many of which are commercially available from suppliers such as Aldrich Chemical Company of Milwaukee Wis. Compounds of structure (230) can be coupled with an appropriately substituted acid chloride derivative of acrylic acid to give amide (232). The groups $R_{103}$, $R_{105}$, and $R_{106}$ can be introduced into compounds of the invention by the selection of the appropriately substituted acrylic acid chloride. Such acrylic acid chlorides are available by a variety of known methods, including as products of Wittig reactions of appropriate aldehydes and ketones with phosphorus ylids of haloacetic acid derivatives. Amide (232) can also be prepared by methods known in the art utilizing a carboxylic acid and a coupling agent such as, for example, a carbodiimide. The amide (232) is converted to 2-oxo-1,2,3,4-tetrahydro-quinoline (234) through a Lewis Acid cyclization. One Lewis acid that can be utilized in the process is, for example, $AlCl_3$. Mineral acids my effect the same cyclization. At this stage $R_{101}$ can be introduced to give 2-oxo-1, 2,3,4-tetrahydro-quinoline (236) by allowing $R_{101}$-LG, wherein LG is a leaving group, such as, for example, Cl, Br, I, OTf, and the like, to react with the nitrogen anion of 2-oxo-1,2,3,4-tetrahydro-quinoline (234). The anion of 2-oxo-1,2,3,4-tetrahydro-quinoline (234) can be generated using a base such as, for example, KOH/DMSO, NaH and the like.

Another method, for example, includes the use of aniline (237) that can be coupled with an acid chloride to give amide (238). The groups $R_{103}$ and $R_{104}$ can be introduced into compounds of the invention by the selection of the appropriate acid chloride. Amide (238) can also be prepared by methods known in the art utilizing a carboxylic acid and a coupling agent such as, for example, a carbodiimide. At this stage $R_{101}$ can be introduced to give amide (240) by allowing $R_{101}$-LG to react with the nitrogen anion of amide (238), wherein LG is a leaving group, such as, for example, Cl, Br, I, OTf, and the like. 2-oxo-2,3-dihydro-1H-indole (242) can be prepared from amide (240) through a Pd-assisted cyclization. Various ligands with Pd can be employed, such as, for example, tricyclohexyl-phosphine. The methoxy group of amide (242) can be converted to phenol (244) using a variety of methods known in the art, such as, for example, $BBr_3$. The resulting phenol (244) can be converted into triflate (246), or the like, using triflic anhydride or similar reagent that is suitable for coupling with $Ar_6$.

Another method, for example, includes the use of readily available phenylene diamines of structure (248), that can be condensed with oxylyl chloride to give quinoxaline-2,3-dione (250). $R_{101}$ can be introduced by allowing $R_{101}$-LG to react with the nitrogen anion of quinoxaline-2,3-dione (250), wherein LG is a leaving group, such as, for example, Cl, Br, I, OTf, and the like. $R_{102}$ can be introduced by allowing $R_{102}$-LG to react with the nitrogen anion of quinoxaline-2, 3-dione (250), wherein LG is a leaving group, such as, for example, Cl, Br, I, OTf, and the like. $R_{101}$ and $R_{102}$ can be the same or different. Quinoxaline-2,3-dione (252) can be brominated to give quinoxaline-2,3-dione (254) using methods known in the art, such as, for example, $Br_2$ or equivalent, in an appropriate solvent, such as acetic acid. Bromination might also be carried out prior to the introduction of $R_{101}$ and $R_{102}$.

Figure 9:
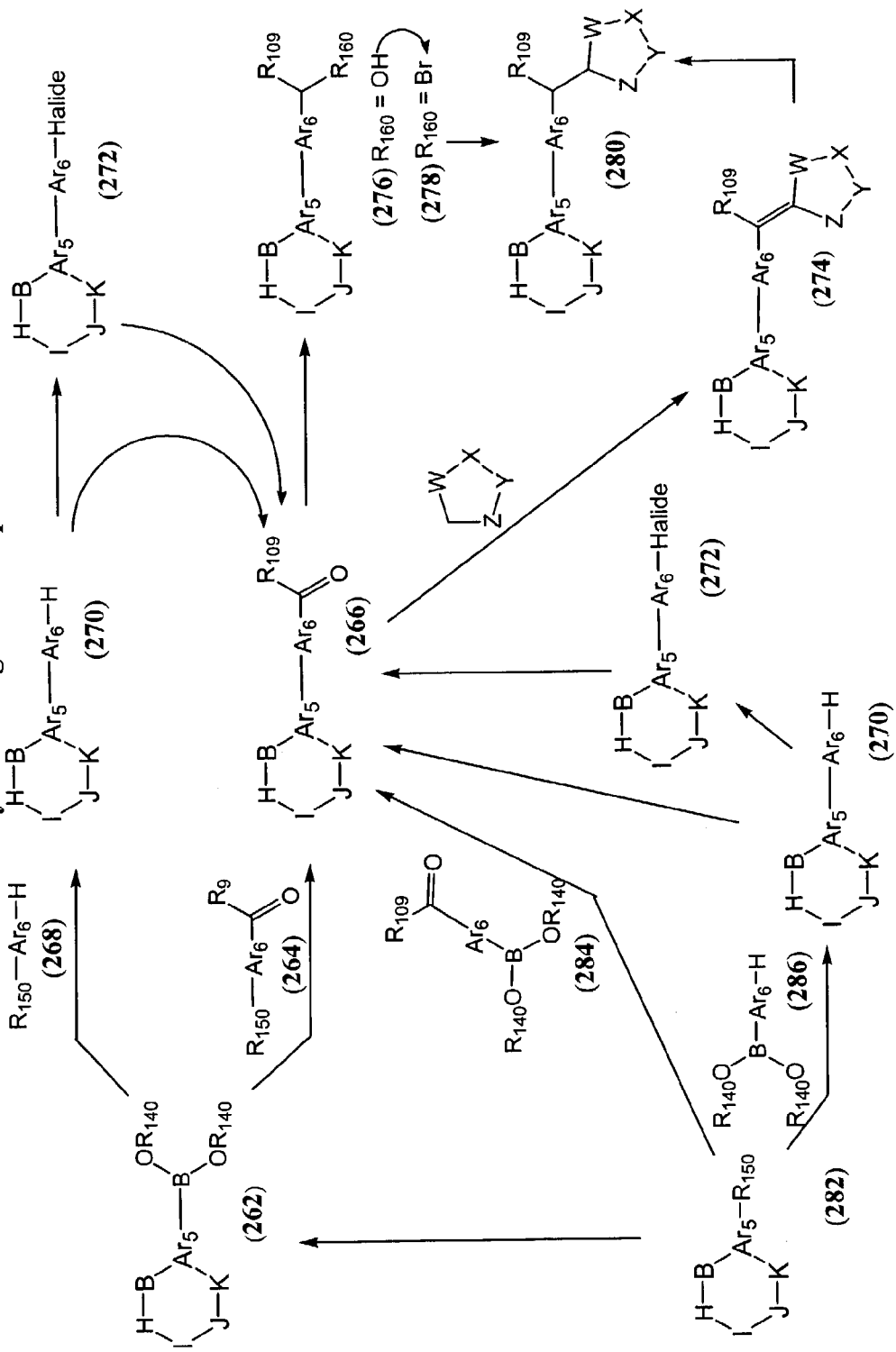
FIG. 9 shows examples of methods for synthesizing the compounds disclosed herein.

Various synthetic methods can be employed in coupling AR5 and AR6. A representative set of synthetic pathways is shown in FIG. 9. One method, for example, includes coupling a boronic acid of Formula (262), $R_{140}$=H, with a suitable carbonyl-containing aryl of Formula (264), such as $R_{150}$=Br, I, Cl, triflate or the like, to give biaryl (266) that is substituted with a carbonyl group, such as a formyl group (i.e., $R_{109}$=H). Alternatively, boronic acid (262) can be coupled with aryl (268), such as when $R_{150}$=Br, I, Cl, triflate or the like, to give biaryl (270) that is subsequently formylated using techniques known in the art, such as the Vilsmeier or the Vilsmeier-Haack reaction, the Gatterman reaction, the Duff reaction, the Reimer-Tiemann reaction or a like reaction. Coupling reactions such as that described for the formation of Biaryl (266) and (270) can also be conducted using boronic esters, such as where $R_{140}$ together with the boron from a pinacol borate ester (formation of pinacol esters: Ishiyama, T., et al., *J. Org. Chem.* 1995, 60, 7508–7510, Ishiyama, T., et al., *Tetrahedron Letters* 1997, 38, 3447–3450; coupling pinacol esters: Firooznia, F. et al., *Tetrahedron Letters* 1999, 40, 213–216, Manickam, G. et al., *Synthesis* 2000, 442–446; all four citations incorporated herein by reference). In the example for aryl (268) when $R_{150}$ is a triflate, it can easily be obtained by known methods from the corresponding phenol.

Biaryl (270) can also be acylated, for example by the Friedel-Crafts Acylation reaction (using an acid chloride) or the like to give biaryl (266) where $R_{109}$ is not hydrogen. Alternatively, in a two step manner, biaryl (270) is formylated by first performing a halogenation step to give biaryl (272), such as a bromination, followed by a halogen-metal exchange reaction using an alkyl lithium or lithium tributylmagnesate complex as described by Iida, et. al. in Tetrahedron Letters 2001, 42, 4841–4844 and reaction with DMF or equivalent known in the art to give biaryl (266) where $R_{109}$ is H. The carbonyl group of biaryl (266) can subsequently be condensed with a heterocycle possessing an active methylene moiety, such as 2,4-thiazolidinedione, 2-thioxo-thiazolidine-4-one, 2,4-imidazolidinedione or 2-thioxo-imidazolidine-4-one to give benzylidene (274). The carbonyl group of biaryl (266) can also be reduced, such as with sodium borohydride, diisobutyl aluminum hydride, or the like, to give benzyl alcohol (276, $R_{160}$=OH) and converted to benzyl bromide (278, $R_{160}$=Br) with HBr or some other method known in the art, such as $PPh_3/CBr_4$ or converted to another leaving group, such as, for example, mesylate or iodide. Benzyl bromide (278, $R_{160}$=Br) or like compound is allowed to react with the anion(s) of 2,4-thiazolidinedione to give biaryl [(280), where: W=—C(O)—, X=—NH—, Y=—C(O)— and Z=—S—]. Similarly, anions of other heterocycles disclosed herein can be used. Alternative, biaryl [(280), where: W=—C(O)—, X=—NH—, Y=—C(O)— and Z=—S—] can be prepared by a reduction of benzylidene [(274), where: W=—C(O)—, X=—NH—, Y=—C(O)— and Z=—S—] using methods known in the art, such as hydrogenation in the presence of Pd/C, Mg/MeOH, $LiBH_4$ in THF/pyridine and the like. A number of methods suitable for reducing benzylidene compounds to benzyl compounds (including hydrogenation, reaction with metal hydride reagents, or dissolving metal reductions) are known to those of skill in the art, and those methods can be applied in the methods of the instant invention.

In an alternative manner, the coupling can take place between aryl (282), such as where $R_{150}$=Br, I, Cl, triflate or the like, and boronic acid (284, $R_{140}$=H or alkyl) to give the above mention biaryl (266). Also aryl (282) can be coupled with boronic acid (286) to give biaryl (270). Employing the same strategy as described above biaryl (270) can be converted to biaryl (266).

Coupling of two aryl rings can be conducted using an aryl boronic acid or esters with an aryl halide (such as, iodo, bromo, or chloro), triflate or diazonium tetrafluoroborate; as described respectively in Suzuki, *Pure & Applied Chem.*, 66:213–222 (1994), Miyaura and Suzuki, *Chem. Rev.* 95:2457–2483 (1995), Watanabe, Miyaura and Suzuki, *Synlett.* 207–210 (1992), Littke and Fu, *Angew. Chem. Int. Ed.*, 37:3387–3388 (1998), Indolese, *Tetrahedron Letters*, 38:3513–3516 (1997), Firooznia, et. al., *Tetrahedron Letters* 40:213–216 (1999), and Darses, et. al., *Bull. Soc. Chim. Fr.* 133:1095–1102 (1996); all incorporated herein by reference. According to this coupling reaction, precursors such as (262) and (264) can be employed:

(262)

(264)

where $R_{140}$ is either alkyl, cycloalkyl (i.e., pinacol) or hydrogen and $R_{150}$ is a halide (such as, iodo, bromo, or chloro), triflate or diazonium tetrafluoroborate. Alternately, it is understood that the coupling groups can be reversed, such as the use of (282) and (284), to achieve the same coupling product:

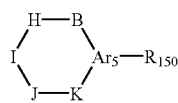
(282)

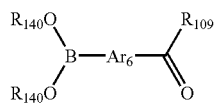
(284)

where $R_{140}$ and $R_{150}$ have the same meaning as described above. The preparation of the above mentioned precursors can be prepared by methods readily available to those skilled in the art. For example, the boronic ester can be prepared from aryl (282, where $R_{150}$=halide) by conversion of the halide to the corresponding aryl lithium, followed by treatment with a trialkyl borate. Methods are know in the art to prepare pinacol boronic esters from triflates such as aryl (282, where $R_{150}$=triflate). The coupling reaction can also be conducted between an arylzinc halide and an aryl halide or triflate. Alternately, the coupling reaction can also be executed using an aryl trialkyltin derivative and an aryl halide or triflate. These coupling methods are reviewed by Stanforth, *Tetrahedron* 54:263–303 (1998) and incorporated herein by reference. In general, the utilization of a specific coupling procedure is selected with respect to available precursors, chemoselectivity, regioselectivity and steric considerations.

Condensation of the biaryl carbonyl containing derivatives (e.g., FIG. 9, compound (266)) with a suitable active methylene compound, such as, 2,4-thiazolidinedione, can be accomplished by the use of methods known in the art. For example, the biaryl carbonyl product from the coupling reaction can be condensed with an active methylene compound to give a benzylidene compound of Formula (200) (i.e., ----- is a bond) as described by Tietze and Beifuss, *Comprehensive Organic Synthesis* (Pergamon Press), 2:341–394, (1991), incorporated herein by reference. It is understood by those skilled in the art that intermediates having hydroxyl groups bonded thereto can be formed during condensation of a biaryl carbonyl containing derivative and an active methylene compound, as shown below.

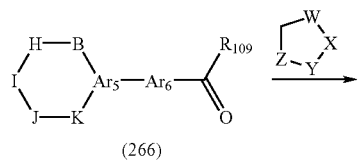
(266)

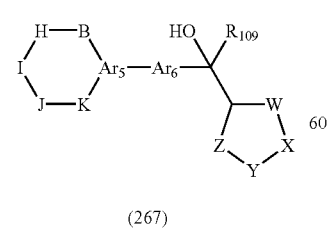
(267)

The hydroxyl groups of intermediates (267) are often eliminated (as water) during the condensation reaction, to form the desired benzylidene compound. Nevertheless, the conditions of the reaction can be modified for the isolation or further use of hydroxyl containing intermediates, and such embodiments are within the scope of the invention. Effective catalysts for the condensation can be selected from ammonia, primary, secondary and tertiary amines, either as the free base or the amine salt with an organic acid, such as acetic acid. Examples of catalysts include pyrrolidine, piperidine, pyridine, diethylamine and the acetate salts thereof. Inorganic catalysts can also be used for the condensation. Inorganic catalysts include, but are not limited to, titanium tetrachloride and a tertiary base, such as pyridine; and magnesium oxide or zinc oxide in an inert solvent system. This type of condensation can be strongly solvent-dependent and it is understood that routine experimentation may be necessary to identify the optimal solvent with a particular catalyst, preferable solvents include ethanol, tetrahydrofuran, dioxane or toluene; or mixtures thereof.

In view of the teachings and disclosure above, in some aspects, the invention relates to methods for preparing the compounds of the invention, wherein the method comprises a) coupling i) an $Ar_5$ precursor compound having the structure

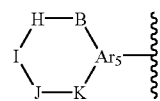

ii) with an $Ar_6$ precursor compound having the structure

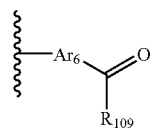

iii) to form a carbonyl containing precursor compound having the structure

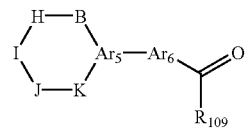

b) further reacting the carbonyl containing precursor compound so as to connect to the carbonyl of the carbonyl containing precursor an HAr heterocycle.

The methods of making the compounds of the invention further comprise steps wherein the further reacting comprises condensing the carbonyl containing precursor compound with a compound having the structure

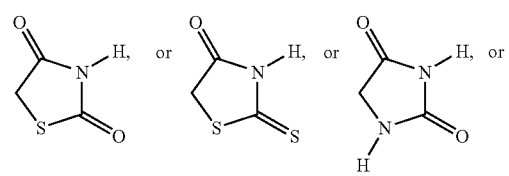

-continued

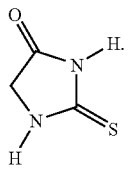

As is understood by those of ordinary skill in the art of synthetic organic chemistry, the various synthetic strategies, organic reactions, and/or functional group transformations utilized herein can be performed by a number of strategies, reactions, or procedures other than those explicitly described above. References for other synthetic procedures that can be utilized for the synthetic steps leading to the compounds disclosed herein can be found in, for example, March, J., *Advanced Organic Chemistry*, 4$^{th}$ *Edition*, Weiley-Interscience (1992); or Larock, R. C., *Comprehensive Organic Transformations, A Guide to Functional Group Preparations*, VCH Publishers, Inc. (1989), both incorporated herein by reference.

Pharmaceutical Compositions

Although the compounds described herein can be administered as pure chemicals, it is preferable to present the active ingredient as a pharmaceutical composition. Thus another embodiment is the use of a pharmaceutical composition comprising one or more compounds and/or a pharmaceutically acceptable salt thereof, together with one or more pharmaceutically acceptable carriers thereof and, optionally, other therapeutic and/or prophylactic ingredients. The carrier(s) must be 'acceptable' in the sense of being compatible with the other ingredients of the composition and not overly deleterious to the recipient thereof.

Pharmaceutical compositions include those suitable for oral, enteral, parental (including intramuscular, subcutaneous and intravenous), topical, nasal, vaginal, ophthalinical, sublingually or by inhalation administration. The compositions can, where appropriate, be conveniently presented in discrete unit dosage forms and can be prepared by any of the methods well known in the art of pharmacy. Such methods include the step of bringing into association the active compound with liquid carriers, solid matrices, semi-solid carriers, finely divided solid carriers or combination thereof, and then, if necessary, shaping the product into the desired delivery system.

Pharmaceutical compositions suitable for oral administration can be presented as discrete unit dosage forms such as hard or soft gelatin capsules, cachets or tablets each containing a predetermined amount of the active ingredient; as a powder or as granules; as a solution, a suspension or as an emulsion. The active ingredient can also be presented as a bolus, electuary or paste. Tablets and capsules for oral administration can contain conventional excipients such as binding agents, fillers, lubricants, disintegrants, or wetting agents. The tablets can be coated according to methods well known in the art., e.g., with enteric coatings.

Oral liquid preparations can be in the form of, for example, aqueous or oily suspensions, solutions, emulsions, syrups or elixirs, or can be presented as a dry product for constitution with water or other suitable vehicle before use. Such liquid preparations can contain conventional additives such as suspending agents, emulsifying agents, non-aqueous vehicles (which can include edible oils), or one or more preservative.

The compounds can also be formulated for parenteral administration (e.g., by injection, for example, bolus injection or continuous infusion) and can be presented in unit dose form in ampules, pre-filled syringes, small bolus infusion containers or in multi-does containers with an added preservative. The compositions can take such forms as suspensions, solutions, or emulsions in oily or aqueous vehicles, and can contain formulatory agents such as suspending, stabilizing and/or dispersing agents. Alternatively, the active ingredient can be in powder form, obtained by aseptic isolation of sterile solid or by lyophilization from solution, for constitution with a suitable vehicle, e.g., sterile, pyrogen-free water, before use.

For topical administration to the epidermis, the compounds can be formulated as ointments, creams or lotions, or as the active ingredient of a transdermal patch. Suitable transdermal delivery systems are disclosed, for example, in Fisher et al. (U.S. Pat. No. 4,788,603, incorporated herein by reference) or Bawas et al. (U.S. Pat. Nos. 4,931,279, 4,668,504 and 4,713,224; all incorporated herein by reference). Ointments and creams can, for example, be formulated with an aqueous or oily base with the addition of suitable thickening and/or gelling agents. Lotions can be formulated with an aqueous or oily base and will in general also contain one or more emulsifying agents, stabilizing agents, dispersing agents, suspending agents, thickening agents, or coloring agents. The active ingredient can also be delivered via iontophoresis, e.g., as disclosed in U.S. Pat. Nos. 4,140,122, 4,383,529, or 4,051,842; incorporated herein by reference.

Compositions suitable for topical administration in the mouth include unit dosage forms such as lozenges comprising active ingredient in a flavored base, usually sucrose and acacia or tragacanth; pastilles comprising the active ingredient in an inert base such as gelatin and glycerin or sucrose and acacia; mucoadherent gels, and mouthwashes comprising the active ingredient in a suitable liquid carrier.

When desired, the above-described compositions can be adapted to provide sustained release of the active ingredient employed, e.g., by combination thereof with certain hydrophilic polymer matrices, e.g., comprising natural gels, synthetic polymer gels or mixtures thereof. The pharmaceutical compositions according to the invention can also contain other adjuvants such as flavorings, coloring, antimicrobial agents, or preservatives.

Therefore, in some embodiments the invention relates to a pharmaceutical composition comprising one or more pharmaceutically acceptable carriers and one or more compounds of the invention, or a pharmaceutically acceptable salt thereof, in an amount that can be used to effectively treat diabetes, cancer, or atherosclerosis, or modulate lipid metabolism, carbohydrate metabolism, lipid and carbohydrate metabolism, or adipocyte differentiation, in a mammal.

Biological Activity Testing for Compounds of the Invention

The compounds of the present invention have been found to be potent compounds in a number of biological assays, both in vitro and in vivo, that correlate to, or are representative of, human diseases.

For instance, many of the compounds of the invention can induce the differentiation of preadipocytes into adipocytes. This biological activity (Harris and Kletzien, *Mol. Pharmacol.*, 45:439–445 (1994); Wilson et al., *J. Med. Chem.* 39:665–668 (1996)) has been observed for certain compounds that have antidiabetic activity in humans (Teboul et al., *J. Biol. Chem.* 270:28183–28187 (1995)) and has been used by many in the art to screen new compounds for anti-diabetic activity. The ability of the compounds to induce cells of the adipocyte lineage to differentiate can also correlate to the ability of the compounds to treat or prevent other diseases including proliferative diseases such as breast, prostate and other cancers.

The compounds of the invention have been screened in an in-vitro adipocyte differentiation assay, as described in Example 26. Mouse pre-adipocyte 3T3-L1 cells were treated with compounds at concentrations less than or equal to $10^{-6}$ M for 7 days. Pre-adipocyte cells that become differentiated into adipocytes begin to accumulate lipids, and accordingly can exhibit an increase in lipid content. Results from the testing are shown in FIG. 1, wherein the lipid content of the cells after treatment with the compounds of the invention is displayed as a function of the identity of the compound and the concentration at which it was applied. The relative lipid content of the cells is plotted in FIG. 1 relative to the results obtained by the application of compound 24, which has been shown to be a potent inducer of adipocyte differentiation, and also a compound that is useful for the treatment of diabetes.

As can be seen from FIG. 1 and/or Example 26, several of the compounds whose preparation is documented in the examples induced differentiation of the preadipocytes at concentrations ranging as low as $1\times10^{-10}$ Molar, and hence showed a positive indication of biological activity sufficient to justify further in-vivo testing.

In order to demonstrate the activity of the various compounds of the invention for effectiveness and/or activity for adipocyte differentiation, the compound can be applied at a concentration of about $1\times10^{-6}$ M for a period of about 7 days, to mouse preadipocyte 3T3-L1 cells, and measure the increase the lipid content of the cells. The compounds can be considered active for adipocyte differentiation if the lipid accumulation induced is at least about 20%, or at least about 40% of the lipid accumulation induced by 5-[3-(3,5,5,8,8-Pentamethyl-5,6,7,8-tetrahydro-naphthalen-2-yl)-4-trifluoromethoxy-benzylidene]-thiazolidine-2,4-dione when it is applied to control cultures of mouse preadipocyte 3T3-L1 cells at a concentration of about $1\times10^{-7}$ M.

The ability of the compounds to function as antidiabetic agents can be demonstrated in-vivo in certain known animal models for type 2 diabetes [Coleman, D. L, Diabetes, vol. 31, suppl 1, pp 1–6, (1982); Chang A. Y. et al, diabetes, pp 466–470, (1986)]. These known animal models include among others, db/db mice, ob/ob mice, and KKA$^y$ mice.

Diabetes and Lipid Metabolism Efficacy Testing in KKA$^y$ Mice.

(See Results in FIGS. 2a–e and Example 27.)

Of the three mouse models, the KKA$^y$ mice exhibit the most severe symptoms of type 2 diabetes, including hyperglycemia, hypertriglyceridemia and hypercholesterolemia, and therefore are often the most difficult to treat.

As can be readily seen from FIGS. 2a–2e, the compounds of the invention were found to be very effective for simultaneously and beneficially decreasing serum glucose, serum triglyceride, and/or serum cholesterol in KKA$^y$ Mice.

Figure 3:
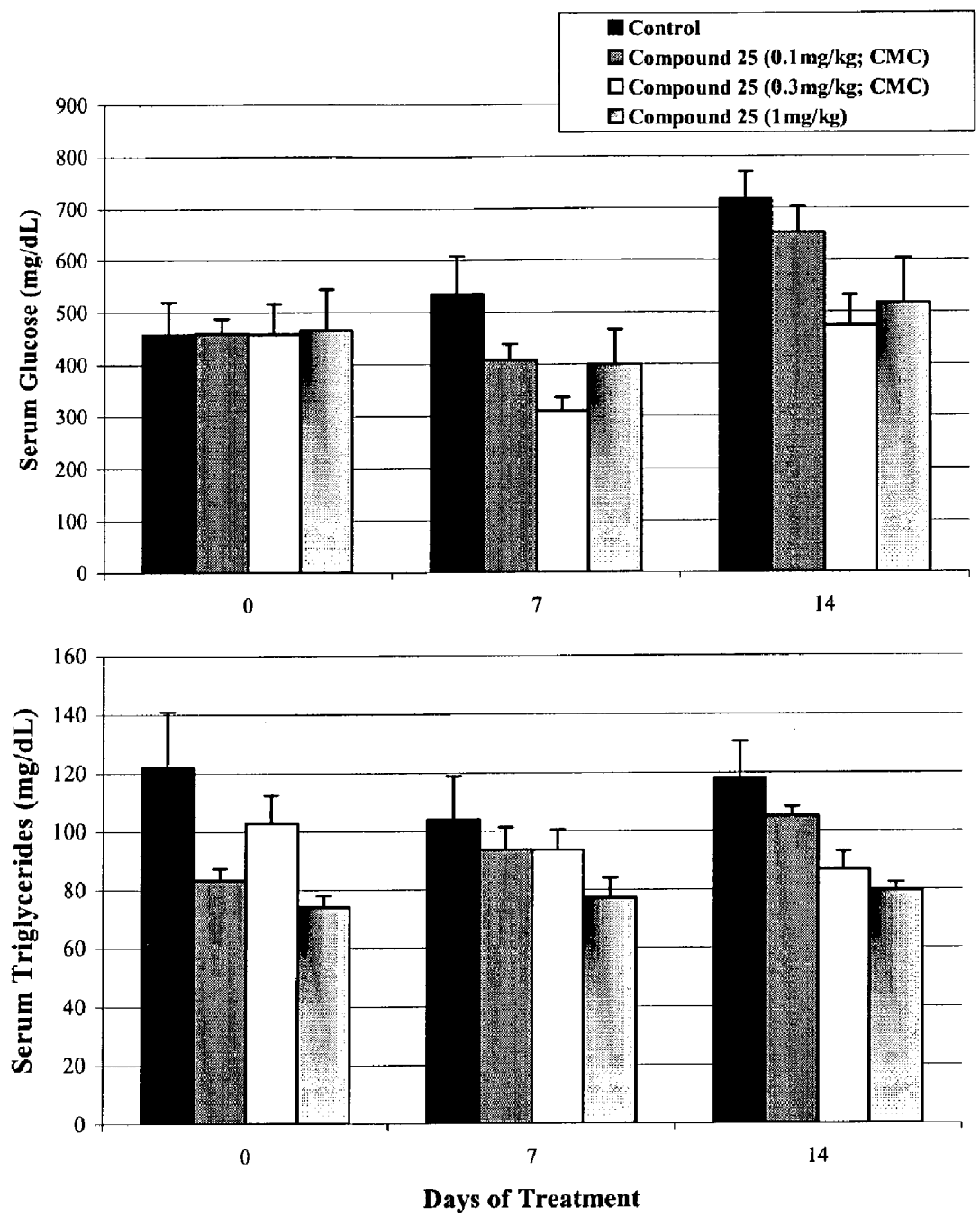
FIG. 3 shows the glucose and triglyceride lowering activity of compound 25 in the type 2 diabetic db/db Mouse Model.

Diabetes and Lipid Metabolism Efficacy Testing in db/db Mutant Mice (See Results in FIG. 3 and Example 28).

While both db/db mice, ob/ob mice are considered model of type 2 diabetes, the severity of the disease in these models is less pronounced than in KKA$^y$ mice. They are however still used as tools to demonstrate the efficacy of the compounds in treating type 2 diabetes. As can be readily seen from FIG. 3, Compound 25 was found to be effective very for simultaneously and beneficially decreasing serum glucose and serum triglycerides in db/db Mice.

Figure 4:
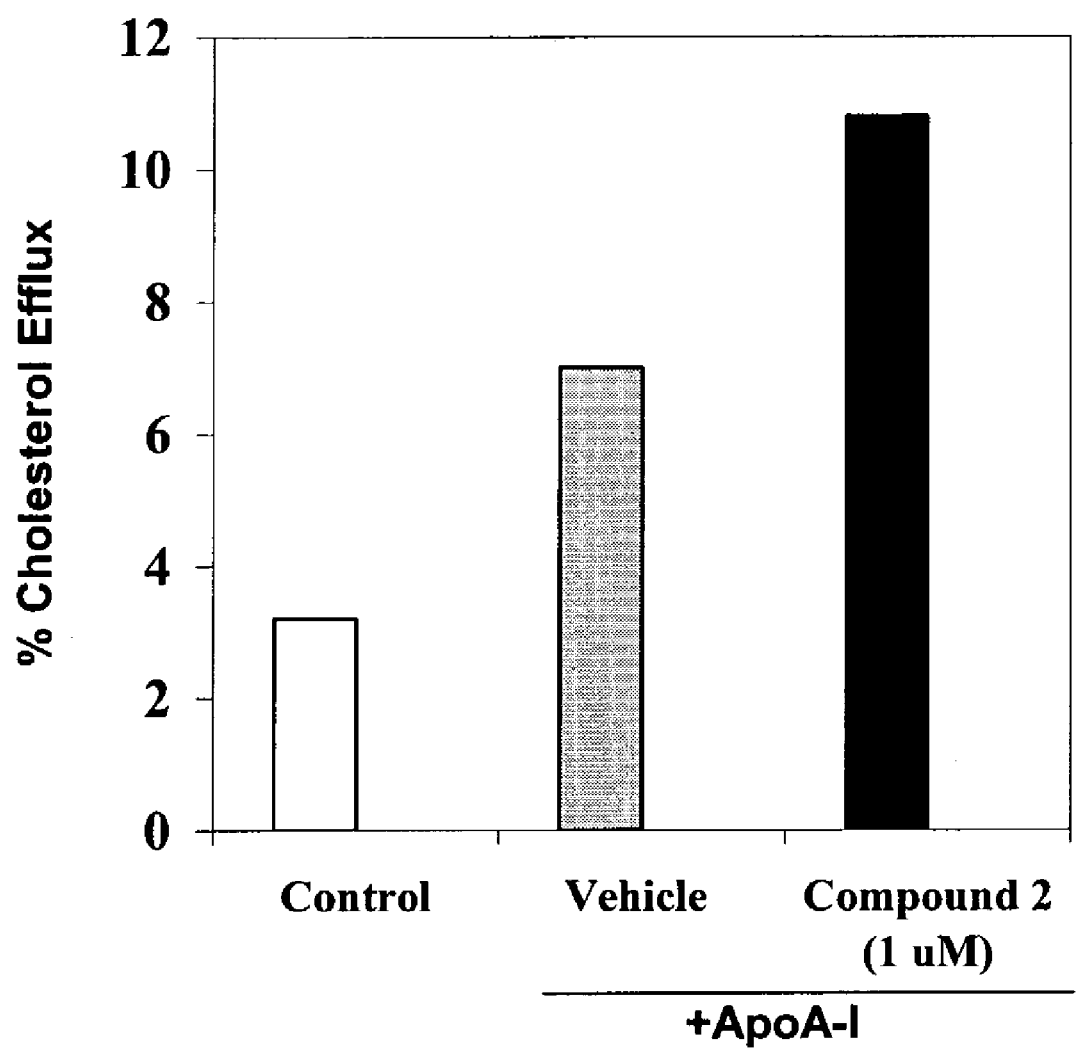
FIG. 4 shows the ability of compound 2 to increase cholesterol efflux from macrophage cells.

Activity for Inducing Cholesterol Efflux from Macrophage Foam Cells (See Results in FIG. 4 and Example 29)

Elevated levels of cholesterol lead to atherosclerosis and heart disease, which in many type 2 diabetes patients is the cause of death. Atherosclerotic lesions results from Cholesterol-loaded macrophage foam cells [Gown et al. (1986) Am. J. Phathol. 125, 191–207]. In vitro, macrophages that are cholesterol-loaded in cell culture can unload excess cholesterol, which can be measured in a "Cholesterol Efflux Assay" (see example 29). The cholesterol released from the Macrophage Foam Cells can be metabolized by the liver and eliminated from the body. Therefore, novel therapeutic agents that increase cholesterol efflux from macrophages in arteriosclerotic lesions can improve the outcome for patients with coronary artery disease such as in obese and diabetes patients.

As can be readily seen from FIG. 4, Compound 2 was found to be very effective for inducing cholesterol efflux from Macrophage Foam Cells, this indicating its use for the control and/or treatment of atherosclerosis.

Activity for Modulation of HDL and LDL Cholesterol Levels in Diet Induced Hypercholesterolemic Sprague Dawley Rats (See Results in FIG. 5 and Example 30.)

The ability of a compound to reduce certain lipids such as cholesterol or to change the ratio of good versus bad cholesterol, i.e. HDL versus LDL, can be measured in animal models. One animal model commonly used for such testing is the diet-induced hypercholesterolemic wild type Sprague Dawley rat (see example 30).

Figure 5A:
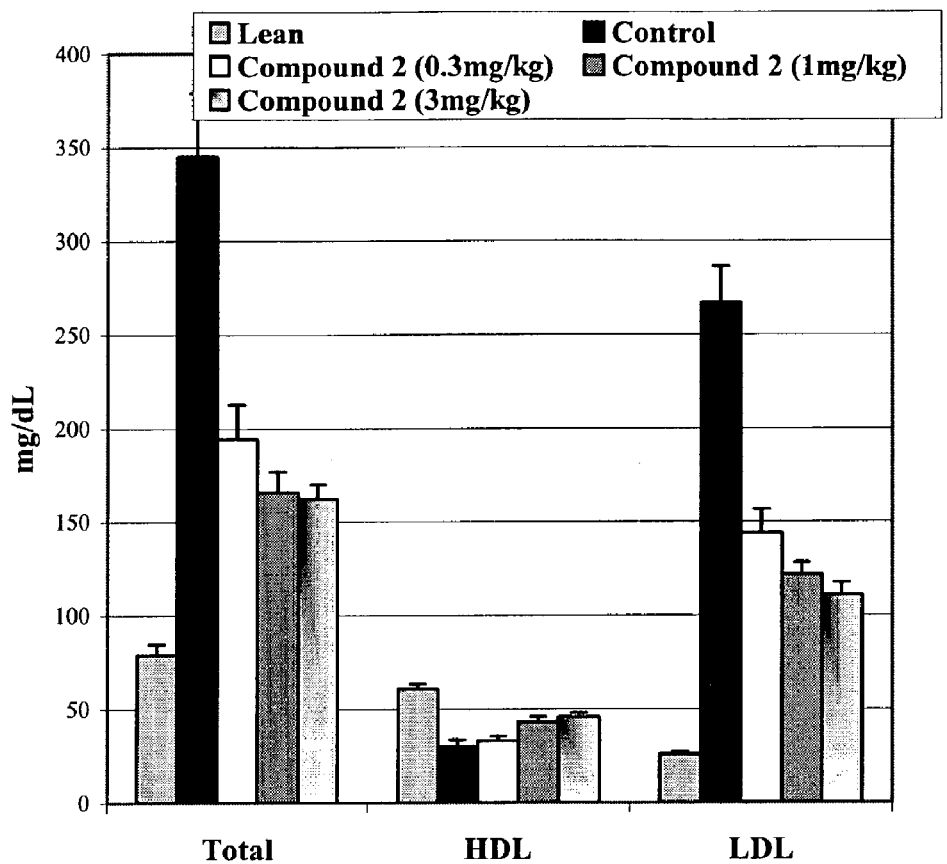
FIGS. 5a–c show the ability of compounds 2, 6, and 25 to decrease total cholesterol and LDL (bad cholesterol) while increasing HDL (good cholesterol) in Sprague Dawley rats.
Figure 5B:
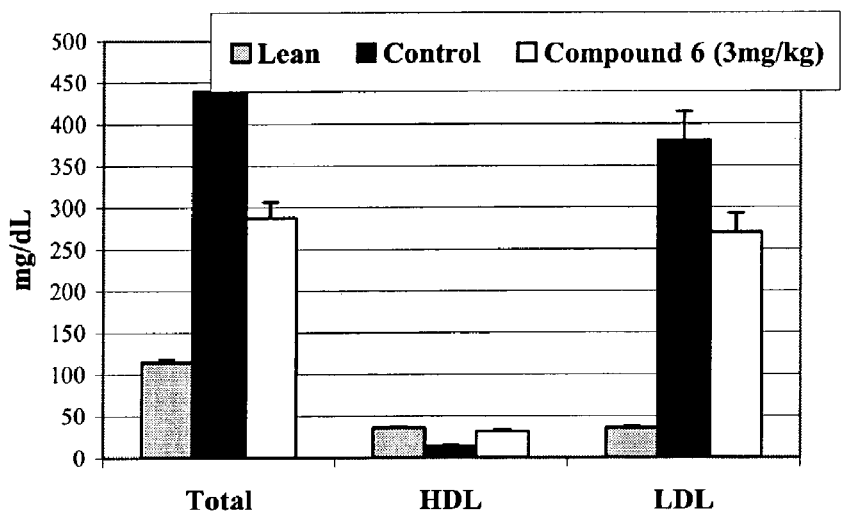
Figure 5C:
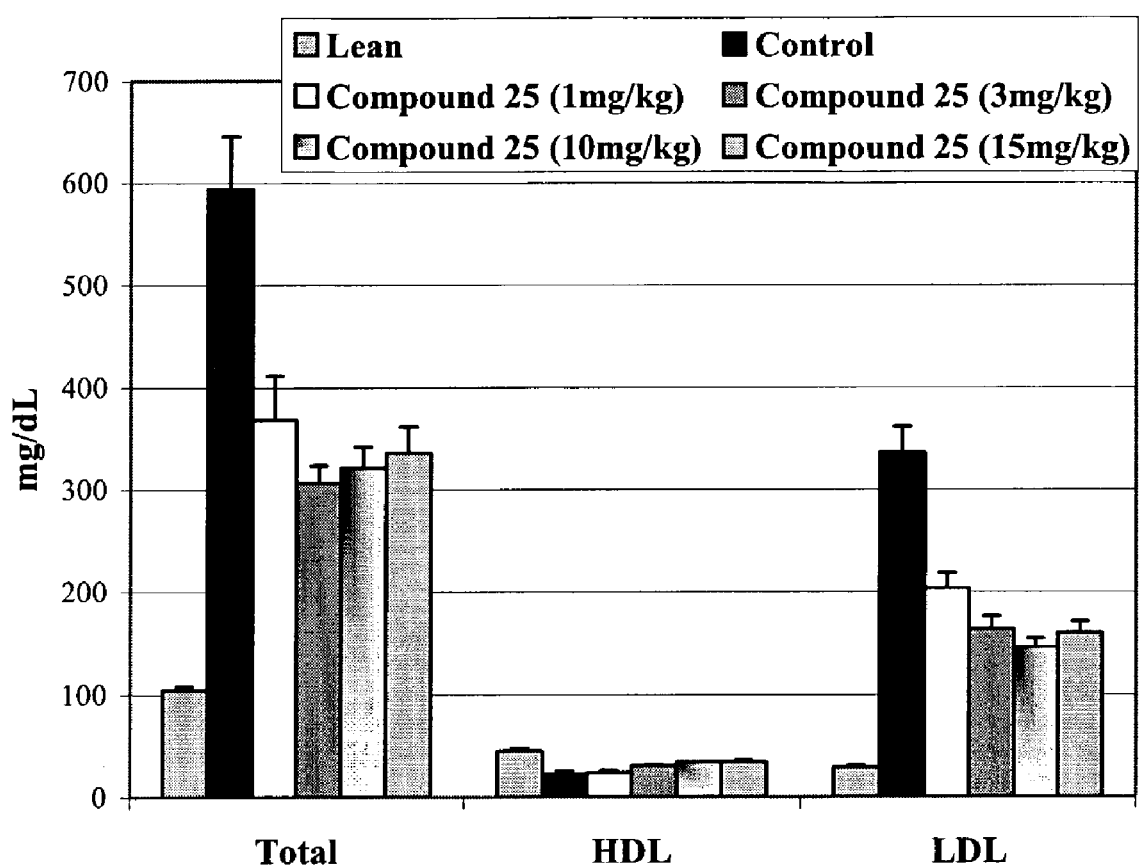

As can be readily seen from FIGS. 5a–c, Compounds 2, 6, and 25 were found to provide unexpectedly beneficial modulation of HDL and LDL cholesterol levels in diet-induced hypercholeterolemic Sprague Dawley Rats, thus indicating significant potential for the control and/or treatment of atherosclerosis in diabetes patients.

Figure 6:
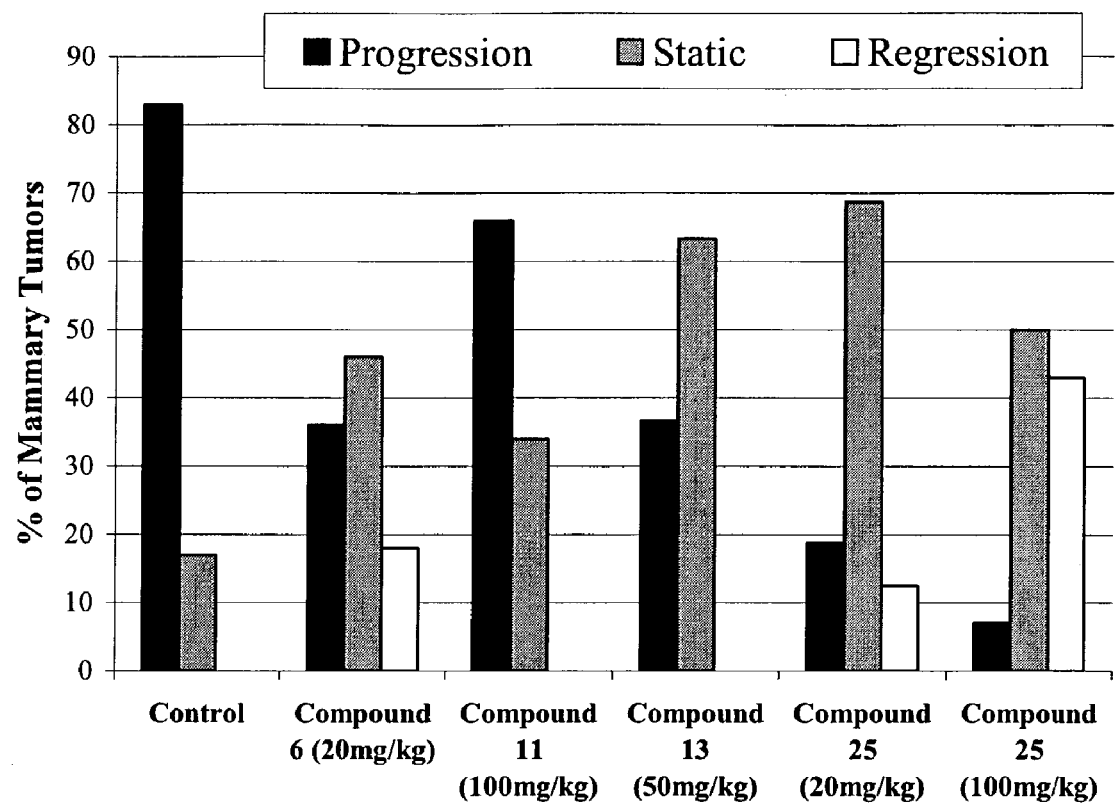
FIG. 6 shows the ability of the compounds to decrease the number of progressing carcinogen induced mammary tumors in Sprague Dawley rats, and increase the number of static and regressing tumors.

Effect on Breast Cancer Tumor Progression Caucinogen Induced Mammary Tumors in Wild Type Sprague Dawley Rats (See Results in FIG. 6 and Example 31.)

The ability of the compounds to function as anti-breast cancer agents can be demonstrated in vivo in carcinogen induced mammary tumors in wild type Sprague Dawley Rats [Thompson H. J et al, Carcinogenesis, 13(9), 1535–1539 (1992)].

As can be readily seen from FIG. 6, Compounds 6, 11, 13, and 25 were unexpectedly found to slow or cause regression in the growth of breast cancer tumors in Sprague Dawley Rats, thus indicating significant potential for the control and/or treatment of breast cancer in humans.

Comparison of Oral Bioavailability of Comparative Compound 24 and Compound 25.

Figure 7:
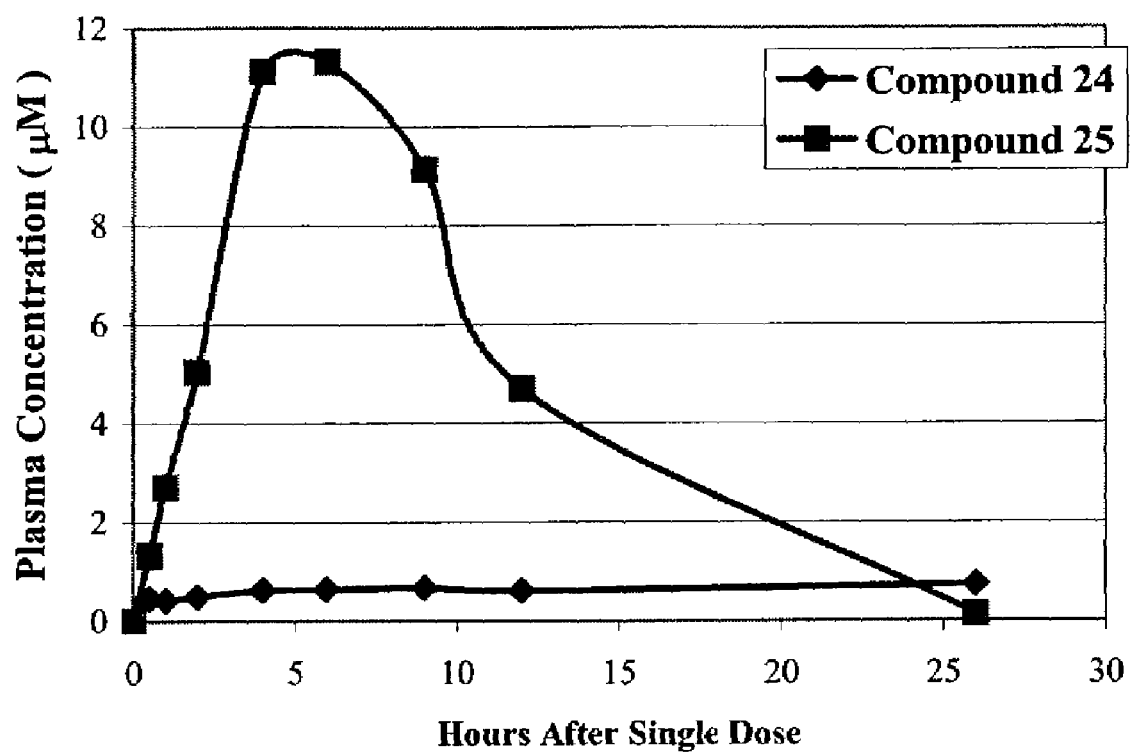
FIG. 7 shows the unexpectedly improved oral bioavailability of compound 25 compared to comparative compound 24.

(See Results in FIG. 7 and Example 32.)

Oral bioavailability is an important pharmaceutical characteristic for a compound to advance through drug development. A basic assessment of the oral bioavailability of a compound can be done in a single dose pharmacokinetic study in wild type rats.

As can be readily seen from FIG. 7, Compounds 25 exhibit unexpectedly superior bioavailability as compared to Compound 24.

Methods of Treating Diseases

Compounds disclosed herein are useful, for example, to modulate metabolism (such as, for example, lipid metabolism and carbohydrate metabolism) or adipocyte differentiation. Changes in carbohydrate metabolism can directly or indirectly also result in changes of lipid metabolism and, similarly, changes in lipid metabolism can lead to changes in carbohydrate metabolism. An example is type 2 diabetes where an increase in free fatty acids in the patients leads to decreased cellular uptake and metabolism of glucose.

Carbohydrate metabolism can be up-regulated or down-regulated to either approach the level of carbohydrate metabolism in a control or to deviate from the level of carbohydrate metabolism in a control. For example, the compounds of the invention can be effective to lower serum glucose levels of $KKA^y$ or db/db mice maintained on a high fat diet by at least about 5%, or at least about 10%, when orally administered to the mice at a concentration of about 0.3 mg/kg for 7 days, as compared to control mice that do not receive the compounds.

As a result of their activity for regulating carbohydrate metabolism, the compounds of the invention can be effective for treating type 2 diabetes. Therefore, in some embodiments, the invention relates to methods of treating type 2 diabetes comprising administering to a mammal diagnosed as needing such treatment, including humans, one or more compounds of the invention, or a pharmaceutically acceptable salt thereof, in an amount effective to treat type 2 diabetes. In some embodiments, the one or more compounds or salts are applied in an amount effective to decrease blood glucose levels in the mammal by at least about 5%, or at least about 10%.

Modulation of lipid metabolism, for example, can include an increase of lipid content intracellularly or extracellularly. Modulation, for example, could involve increase in lipid metabolism, such that lipid metabolism is greater than that of a control. Modulation, also includes, for example, an increase in lipid metabolism, such that the lipid metabolism approaches that of a control. For example, the compounds of the invention and their pharmaceutically acceptable salts can be employed to induce cholesterol efflux from Macrophage Foam Cells as described in Example 29, in order to treat atherosclerosis.

Modulation of lipid metabolism could also include a decrease of lipid content intracellularly or extracellularly. Modulation of metabolism can occur directly for example, through binding of the compound of the invention with its cognate receptor, which directly affects an increase or decrease in lipid content by up-regulation or down-regulation of a gene involved in lipid metabolism. Modulation of metabolism can also occur indirectly, for example, through binding of the compound of the invention with its cognate receptor, which up-regulates or down-regulates cellular differentiation or growth of cells that produce lipids, thereby indirectly causing lipid metabolism to be modulated. As shown in Examples 28 and 29, the compounds of the invention can be effective to lower serum triglyceride levels of $KKA^y$ or db/db mice maintained on a high fat diet by at least about 5%, or at least about 10%, when orally administered to the mice at a concentration of about 0.3 mg/kg for 7 days, as compared to control mice that do not receive the compounds.

Therefore, in some embodiments, the invention relates to methods of treating dyslipidemia comprising administering to a mammal diagnosed as needing such treatment one or more compounds of the invention, or a pharmaceutically acceptable salt thereof, in an amount effective to decrease triglyceride levels in the animal. In some such embodiments, the invention relates to such methods wherein the one or more compounds or salts are applied in an amount effective to decrease triglyeride levels by at least about 5%, or at least about 10%.

As is well known, cholesterol is a lipid that is closely linked with many biochemical functions, but also with diseases such as atherosclerosis. As is illustrated in Examples 29 and 30, the compounds of the invention can benefit modulate the level of cholesterol, including its manifestations in the HDL and LDL forms. Therefore, in some embodiments, the invention relates to a method of treating hypercholesterolemia comprising administering to a mammal diagnosed as needing such treatment one or more compounds the invention, or a pharmaceutically acceptable salt thereof. In some embodiments, the methods apply the one or more compounds or salts in an amount effective to decrease serum cholesterol levels by at least about 5%, or at least about 10%., or to increase the concentration of HDL cholesterol, or decrease the concentration of LDL cholesterol, or increase the HDL/LDL ratio by at least about 5%, or at least about 10%.

It is understood that a variety of lipid molecules can be modulated. The compounds disclosed herein can modulate a single type of lipid molecule, such as a triglyceride, or the compounds disclosed herein can modulate multiple types of lipid molecules. The compounds disclosed herein can also modulate a single or variety of carbohydrate molecules. Unexpectedly, the compounds of the invention can simultaneously and beneficially regulate carbohydrate and lipid metabolism so as to simultaneously decrease levels of serum glucose, serum triglycerides, and serum cholesterol. Drugs having such a combination of beneficial properties are of very high value for simultaneous treatment of type 2 diabetes and/or its associated diseases, such as atherosclerosis.

The amide compounds of the invention are also useful for inducing adipocyte differentiation, which can produce a modulation of the metabolism of lipids, including triglycerides and cholesterol. As is shown in Example 26, the compounds of the invention can be effective, when applied at a concentration of about 1 uM for a period of about 7 days, to induce differentiation of mouse preadipocyte 3T3-L1 cells so as to increase their lipid content by at least about 20%, or at least about 40%, or at least about 50%. Such activity for adipocyte differentiation is well known to those of skill in the art to be associated with activity for the treatment of diabetes, cancer, and/or inflammatory diseases. Inflammatory responses of macrophage foam cells are known to be involved in the formation atherosclerotic lesions. Without wishing to be bound by theory, the compounds of the invention are believed to be involved in lessening such inflammatory responses, and/or inducing the macrophages to increase their release of cholesterol, so as to lessen the buildup of cholesterol in blood vessel walls. Therefore, the compounds of the invention are unexpectedly useful in treating diabetes and simultaneously treating the atherosclerosis, which often occurs in diabetic patients.

The compounds of the invention are also useful for treating diseases of uncontrolled cellular proliferation, for which chronic inflammatory responses are known to be a factor, including various cancers. The composition can be useful in the treatment of polycystic kidney disease and cancers such as, carcinomas, lymphomas, leukemias, and sarcomas. A representative but non-limiting list of cancers is lymphoma, Hodgkin's Disease, myeloid leukemia, bladder cancer, brain cancer, head and neck cancer, kidney cancer, lung cancers such as small cell lung cancer and non-small cell lung cancer, myeloma, neuroblastoma/glioblastoma, ovarian cancer, pancreatic cancer, prostate cancer, skin cancer, liver cancer, melanoma, colon cancer, cervical carcinoma, breast cancer, and epithelial cancer. Compounds disclosed herein can also be used for the treatment of inflammatory diseases such as osteoarthritis, rheumatoid arthritis, Crohn's Disease, pulmonary fibrosis, and Inflammatory Bowel Disease.

Therefore, in some embodiments, the invention relates to method of treating cancer comprising administering to a mammal diagnosed as needing such treatment one or more compounds of the invention, or a pharmaceutically acceptable salt thereof, in an amount effective to treat the cancer. In some embodiments the cancer treated is breast cancer.

The compounds of the invention have suitably low molecular weights and good physiological stability. The compounds of the invention also have excellent oral bioavailability, as illustrated in Examples 27, 28, 30, 31, and 32, and therefore, represent a class that have superior pharmacological and physical properties that can be readily implemented to prevent, alleviate, and/or otherwise, treat disorders of lipid and carbohydrate metabolism, such as obesity, dyslipidemia, type 2 diabetes and other diseases related to type 2 diabetes.

A preferred embodiment of the invention relates to the use of the compounds disclosed herein. The compounds disclosed herein can be either used singularly or plurally, and in pharmaceutical compositions thereof for the treatment of mammalian diseases, particularly those related to humans. Compounds disclosed herein and compositions thereof can be administered by various methods including, for example, orally, enterally, parentally, topically, nasally, vaginally, ophthalinically, sublingually or by inhalation for the treatment of diseases related to lipid metabolism, carbohydrate metabolism, lipid and carbohydrate metabolism such as polycystic ovary syndrome, syndrome X, type 2 diabetes, including disorders related to type 2 diabetes such as, diabetic retinopathy, neuropathy, macrovascular disease or differentiation of adipocytes. Routes of administration and dose ages known in the art can be found in *Comprehensive Medicinal Chemistry, Volume* 5, Hansch, C. Pergamon Press, 1990; incorporated herein by reference.

It will be further appreciated that the amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

In general, one of skill in the art understands how to extrapolate in vivo data obtained in a model organism, such as an ob/ob or db/db mouse, to another mammal, such as a human. These extrapolations are not simply based on the weights of the two organisms, but rather incorporate differences in metabolism, differences in pharmacological delivery, and administrative routes. Based on these types of considerations, a suitable dose will, in alternative embodiments, typically be in the range of from about 0.5 to about 100 mg/kg/day, from about 1 to about 75 mg/kg of body weight per day, from about 3 to about 50 mg per kilogram body weight of the recipient per day.

The compound is conveniently administered in unit dosage form; for example, in alternative embodiments, containing 0.5 to 1000 mg, 5 to 750 mg, most conveniently, or 10 to 500 mg of active ingredient per unit dosage form.

One skilled in the art will recognize that dosage and dosage forms outside these typical ranges can be tested and, where appropriate, be used in the methods of this invention.

In separate embodiments, the active ingredient can be administered to achieve peak plasma concentrations of the active compound of from about 0.5 to about 75 µM, about 1 to 50 µM, or about 2 to about 30 µM. This can be achieved, for example, by the intravenous injection of a 0.05 to 5% solution of the active ingredient, optionally in saline, or orally administered as a bolus containing about 0.5–500 mg of the active ingredient. Desirable blood levels can be maintained by continuous infusion to provide about 0.01–5.0 mg/kg/hr or by intermittent infusions containing about 0.4–15 mg/kg of the active ingredients.

The desired dose can conveniently be presented in a single dose or as divided doses administered at appropriate intervals, for example, as two, three, four or more sub-doses per day. The sub-dose itself can be further divided, e.g., into a number of discrete loosely spaced administrations; such as multiple inhalations from an insufflator or by application of a plurality of drops into the eye.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as can be applied to the essential features hereinbefore set forth, and as follows in the scope of the appended claims.

The following examples are given to illustrate the invention and are not intended to be inclusive in any manner:

EXAMPLES

Example 1

5-[3-(1,4,4,6-Tetramethyl-2-oxo-1,2,3,4-tetrahydro-quinolin-7-yl)-4-trifluoromethoxy-benzylidene]-thiazolidine-2,4-dione, Which can be Referred to as "Compound 1"

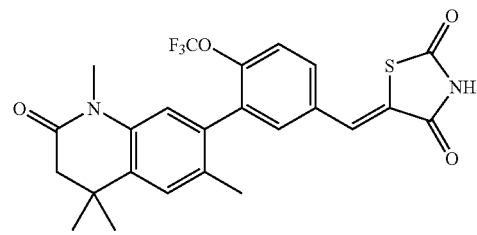

A mixture of toluene (80 mL), piperidine (380 µL), acetic acid (380 µL), 3-(1,4,4,6-Tetramethyl-2-oxo-1,2,3,4-tetrahydro-quinolin-7-yl)-4-trifluoromethoxy-benzaldehyde (7.5 g, 19.16 mmol) and 2,4-thiazolidinedione (2.25 g, 19.16 mmol) was heated at reflux overnight. The reaction mixture was cooled to room temperature, diluted with ethyl acetate and washed with water and brine, dried over MgSO$_4$. The residue was recrystallized successively from ethanol, dichloromethane/hexane and ethanol to afford 4.3 g (46%) of 5-[3-(1,4,4,6-tetramethyl-2-oxo-1,2,3,4-tetrahydroquinolin-7-yl)-4-trifluoromethoxy-benzylidene]-thiazolidine-2,4 dione. mp 182–184° C.

¹H-NMR (300 MHz, DMSO-d-6): 1.27 (s, 6 H), 2.08 (s, 3 H), 2.49 (s, 2 H), 3.25 (s, 3 H), 6.93 (s, 1 H), 7.31 (s, 1 H), 7.66 (s, 1 H), 7.67 (d, J=7.6 Hz, 1 H), 7.75 (dd, J=7.6 and 1.7 Hz, 1 H), 7.84 (s, 1 H), 12.71 (br s, 1 H).

The intermediate 3-(1,4,4,6-tetramethyl-2-oxo-1,2,3,4-tetrahydro-quinolin-7-yl)-4-trifluoromethoxy-benzaldehyde was prepared as follows:

a. 3-(1,4,4,6-Tetramethyl-2-oxo-1,2,3,4-tetrahydro-quinolin-7-yl)-4-trifluoromethoxy-benzaldehyde.

A mixture of 3-formyl-6-trifluoromethoxy-1-phenyl boronic acid (3.14 g, 13.42 mmol), 7-bromo-1,4,4,6-tetramethyl-3,4-dihydro-1H-quinoline-2-one (3.15 g, 11.19 mmol) and potassium carbonate (3.1 g, 22.38 mmol) in toluene (35 mL), ethanol (11.8 mL) and water (7.3 mL) was degassed with argon for 15 minutes. Tetrakis(triphenylphosphine) palladium(0) (0.259 g, 0.02 mmol) was added and the mixture heated at reflux under argon overnight. The solution was cooled to room temperature, diluted with ethyl acetate and washed successively with water and brine, dried over anhydrous magnesium sulfate, filtered and evaporated. The residue was purified on silica gel (20 to 30% ethyl acetate in hexane) to give 2.34 g of 3-(1,4,4,6-tetramethyl-2-oxo-1,2,3,4-tetrahydro-quinolin-7-yl)-4-trifluoromethoxy-benzaldehyde (54%). ¹H NMR (300 MHz; CDCl₃): 1.35 (s, 6 H), 2.11 (s, 3 H), 2.55 (s, 2 H), 3.35 (s, 3 H), 6.79 (s, 1 H), 7.20 (s, 1 H), 7.54 (dd, J=3 and 8.4 Hz, 1 H), 7.85 (d, J=2.7 Hz, 1 H), 7.90 (dd, J=2.1 and 8.7 Hz, 1 H), 10.04 (s, 1 H).

b. 3-formyl-6-trifluoromethoxy-1-phenyl boronic Acid.

To a mixture of 2-(3-bromo-4-trifluoromethoxy-1-phenyl)-1,3-dioxolane (7.20 g, 22.9 mmol) in THF (70 mL) cooled to −78° C. under an atmosphere of argon was added n-BuLi (13.8 mL, 2.5 M, 34.4 mmol) dropwise. The resulting suspension was stirred for 5 minutes and triisopropylborate (15.9 mL, 68.7 mmol) was added dropwise via syringe. The mixture was stirred at −50° C. for 2 hours then warmed up to room temperature and stirred overnight at room temperature. 1.0 N HCl (50 mL) was slowly added to the reaction mixture. After 3 hours the mixture was diluted with ethyl acetate and the layers separated, the aqueous layer was extracted once with ethyl acetate and the two organic layers combined. The resulting organic layer was washed with water, brine and dried (MgSO₄). The mixture was filtered, evaporated and the residue stirred in hexane. The resulting white suspension was filtered and the white solid dried under high vacuum to afford 3.00 g of 3-formyl-6-trifluoromethoxy-1-phenyl boronic acid (56%). ¹H NMR (300 MHz; CDCl₃): δ 7.42 (d, J=7.0 Hz, 1 H), 8.07 (dd, J=2.1 Hz, J₂=8.7 Hz, 1 H), 8.47 (d, J=1.8 Hz, 1 H), 10.05 (s, 1 H).

c. 2-(3-bromo-4-trifluoromethoxy-1-phenyl)-1,3-dioxolane.

To a solution of 3-bromo-4-trifluoromethoxybenzaldehyde (20 g, 74.0 mmol) in toluene (200 mL) was added ethylene glycol (82.6 mL, 1.48 mol) and p-toluenesulfonic acid monohydrate (0.84 g, 4.44 mmol). The reaction mixture was heated at reflux overnight and the water was removed using a Dean Stark apparatus. The solution was cooled to room temperature, poured into aqueous potassium carbonate (10%) and extracted with ethyl acetate. The organic layer was washed with water, brine and dried (MgSO₄). The residue was purified on silica gel (eluent: 10% ethyl acetate in hexane) to give 15.4 g of 2-(3-bromo-4-trifluoromethoxy)-1,3-dioxolane (66%). ¹H NMR (500 MHz; CDCl₃): δ 4.05 (m, 2 H), 4.11 (m, 2 H), 5.79 (s, 1 H), 7.32 (d, 1 H), 7.43 (d, 1 H), 7.77 (d, J=1.1 Hz, 1 H).

d. 7-bromo-1,4,4,6-tetramethyl-3,4-dihydro-1H-quinoline-2-one.

A mixture of powdered KOH (14.06 g, 0.250 mol) in DMSO (150 mL) was stirred at 0° C. for 10 min. 7-Bromo-4,4,6-trimethyl-3,4- dihydro-1H-quinoline-2-one (33.59 g, 0.125 mol) was added cautiously, followed immediately by the addition of methyl iodide (39 mL, 0.625 mol). The reaction mixture was kept at 0° C. for 30 min then slowly warmed up to room temperature and stirred overnight at room temperature. The reaction mixture was poured into water and extracted with dichloromethane washed with water and brine, dried (MgSO₄), filtered and evaporated to give 35.74 g of 7-bromo-1,4,4,6-tetramethyl-3,4-dihydro-1H-quinoline-2-one (99%) and used without further purification in the Suzuki coupling (step a). ¹H NMR (300 MHz; CDCl₃): 1.27 (s, 6 H), 2.37 (s, 3 H), 2.48 (s, 2 H), 3.35 (s, 3 H), 7.12 (s, 1 H), 7.16 (s, 1 H).

e. 7-bromo-4,4,6-trimethyl-3,4-dihydro-1H-quinoline-2-one.

To a solution of 3-methyl-but-2-enoic acid (3-bromo-4-methyl-phenyl)-amide (70.0 g, 261 mmol) at 90° C. was added portion wise, under argon, with vigorous stirring aluminum chloride (52.3 g, 391 mmol) over 1.5 hr. The reaction mixture was stirred for 2 hours at 110–120° C. The reaction mixture was cooled to room temperature and ice-water was carefully added. The solution was extracted with dichloromethane and the organic washed with 2N HCl, water, saturated aqueous NaHCO₃, water and brine, dried (MgSO₄), filtered and evaporated. The residue was crystallized from dichloromethane/hexane to give 46 g of 7-bromo-4,4,6-trimethyl-3,4- dihydro- 1H-quinoline-2-one. The mother liquor was further chromatographed on silica gel (20% ethyl acetate in hexane) to give 6.2 g more of product. (75%). ¹H NMR (300 MHz; CDCl₃): 1.30 (s, 6 H), 2.33 (s, 3 H), 2.46 (s, 2 H), 7.07 (s, 1 H), 7.10 (s, 1 H), 9.87 (br s, 1 H).

f. 3-Methyl-but-2-enoic Acid (3-bromo-4-methyl-phenyl)-amide.

To a biphasic mixture of 3-bromo-4-methylaniline (50 g, 0.269 mol), 10% NaOH (270 mL) and dichloromethane (160 mL) was added dropwise over a period of 2 hours 3,3-dimethylacryloyl chloride (36 mL, 0.322 mol) in dichloromethane (95 mL). The solution was stirred at room temperature for 48 hours then diluted with water (100 mL). The aqueous layer was further extracted with dichloromethane. The organic layers were combined and washed with water and brine, dried (MgSO₄), filtered and evaporated. The white solid was triturated with hexane and collected to give 70 g (97%) of 3-Methyl-but-2-enoic acid (3-bromo-4-methyl-phenyl)-amide. ¹H NMR (300 MHz; CDCl₃): 1.89 (s, 3 H), 2.21 (s, 3 H), 2.33 (s, 3 H), 5.68 (s, 1 H), 7.14 (d, J=8.0 Hz, 1 H), 7.17 (br s, 1 H), 7.33 (d, J=8.0 Hz, 1 H), 7.79 (s, 1 H).

g. 3-bromo-4-methylaniline.

To a solution of 2-bromo-4-nitrotoluene (50 g, 0.231 mol in ethylacetate (330 mL) and Ethanol (150 mL) was added Tin(II)chloride dihydrate (208 g, 0.924 mol) portionwise. The reaction mixture was stirred at room temperature overnight. The solution was then treated with potassium carbonate until pH=7 and filtered over celite. The filtrate was washed with water, aqueous NaHCO₃, water and brine, dried (MgSO₄), filtered and evaporated to give 42.71 g (100%) of 3-bromo-4-methylaniline. ¹H NMR (300 MHz; CDCl₃): 2.27 (s, 3 H), 3.57 (br s, 2 H), 6.54 (dd, J=2.7 Hz and 8.1 Hz, 1 H), 6.90 (d, J=2.1 Hz, 1 H), 6.98 (d, J=8.1 Hz, 1 H).

Example 2

5-[3-(1-Ethyl-4,4,6-trimethyl-2-oxo-1,2,3,4-tetrahydro-quinolin-7-yl)-4-trifluoromethoxy-benzylidene]-thiazolidine-2,4-dione, which can be Referred to as "Compound 2"

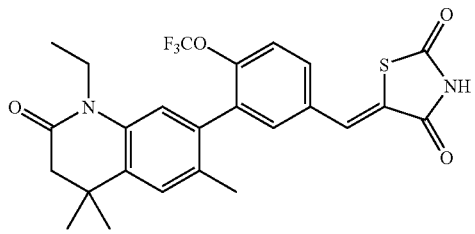

Prepared in a similar manner to example 1 using 3-(1-Ethyl-4,4,6-trimethyl-2-oxo-1,2,3,4-tetrahydro-quinolin-7-yl)-4-trifluoromethoxy-benzaldehyde. 56% yield after column chromatography on silica gel (40% ethyl acetate in hexane). mp 156–154° C. $^1$H-NMR (300 MHz, DMSO-d-6): 1.06 (t, J=7.5 Hz, 3 H); 1.26 (s, 6 H), 2.08 (s, 3 H), 2.46 (s, 2 H), 3.95 (br d, 2 H), 6.97 (s, 1 H), 7.31 (s, 1 H), 7.65 (s, 1 H), 7.66 (dd, J=1.5 Hz and 9 Hz, 1 H), 7.75 (dd, J=2.4 Hz and 8.7 Hz, 1 H), 7.87 (s, 1H), 12.71 (br s, 1 H).

The intermediate 3-(1-Ethyl-4,4,6-trimethyl-2-oxo-1,2,3,4-tetrahydro-quinolin-7-yl)-4-trifluoromethoxy-benzaldehyde was prepared as follows:

a. 3-(1-Ethyl-4,4,6-trimethyl-2-oxo-1,2,3,4-tetrahydro-quinolin-7-yl)-4-trifluoromethoxy-benzaldehyde.

A mixture of 3-formyl-6-trifluoromethoxy-1-phenyl boronic acid (Example 1b) (8.2 g, 34.84 mmol), 7-bromo-1-ethyl-4,4,6-trimethyl-3,4-dihydro-1H-quinoline-2-one (8.6 g, 29.03 mmol) and potassium carbonate (8 g, 58.06 mmol) in toluene (80 mL), ethanol (16 mL) and water (12 mL) was degassed with argon for 30 minutes. Tetrakis(triphenylphosphine)palladium(0) (1.34 g, 0.04 mmol) was added and the mixture heated at reflux under argon for 48 hrs. The solution was cooled to room temperature, diluted with ethyl acetate and washed successively with water and brine, dried over anhydrous magnesium sulfate, filtered and evaporated. The residue was purified on silica gel (30% ethyl acetate in hexane) to give 6.66 g of 3-(1-ethyl-4,4,6-trimethyl-2-oxo-1,2,3,4-tetrahydro-quinolin-7-yl)-4-trifluoromethoxy-benzaldehyde (57%). $^1$H NMR (300 MHz; CDCl$_3$): 1.20 (t, J=7.2 Hz, 3 H), 1.33 (s, 6 H), 1.62 (s, 3 H), 2.10 (s, 3 H), 2.53 (s, 2 H), 4.00 (br d, 2 H), 6.81 (s, 1 H), 7.19 (s, 1 H), 7.55 (dd, J=1.8 and 8.4 Hz, 1 H), 7.85 (d, J=2.4 Hz, 1 H), 7.97 (dd, J=2.1 and 8.4 Hz, 1 H), 10.05 (s, 1 H).

b. 7-bromo-1-ethyl-4,4,6-trimethyl-3,4-dihydro-1H-quinoline-2-one.

A mixture of powdered potassium hydroxide (3.35 g, 59.67 mmol) in DMSO (40 mL) was stirred at 0° C. for 10 min. 7-bromo-4,4,6-trimethyl-3,4- dihydro-1H-quinoline-2-one (Example 1e) (8.0 g, 29.83 mmol) was added cautiously, followed immediately by the addition of ethyl iodide (12 mL, 149.17 mmol). The reaction mixture was kept at 0° C. for 30 min then slowly warmed up to room temperature and stirred overnight at room temperature. The reaction mixture was poured into water and extracted with dichloromethane washed with water and brine, dried (MgSO$_4$), filtered and evaporated to give 8.8 g of 7-bromo-1,4,4,6-tetramethyl-3,4-dihydro-1H-quinoline-2-one and used without further purification in the Suzuki coupling (step a): $^1$H NMR (300 MHz; CDCl$_3$): 1.24 (t, J=7.2 Hz, 1 H), 1.25 (s, 6 H), 2.37 (s, 3 H), 2.45 (s, 2 H), 3.98 (q, 2 H), 7.13 (s, 1 H), 7.18 (s, 1 H).

Example 3

5-[4-Dimethylamino-3-(1,4,4,6-tetramethyl-2-oxo-1,2,3,4-tetrahydro-quinolin-7-yl)-benzylidene]-thiazolidine-2,4-dione, Which can be Referred to as "Compound 3"

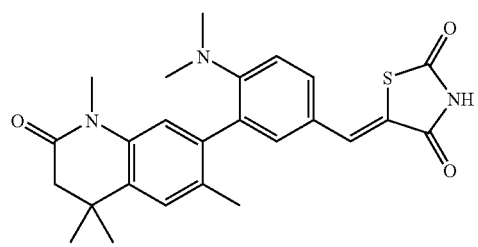

Prepared in a similar manner to example 1 using 4-Dimethylamino-3-(1,4,4,6-tetramethyl-2-oxo-1,2,3,4-tetrahydro-quinolin-7-yl)-benzaldehyde. 73% yield after recrystallisation from ethanol. mp 258–260° C. $^1$H NMR (300 MHz; DMSO) 1.25 (s, 3 H); 1.27 (s, 3 H), 2.07 (s, 3 H), 2.47 (s, 2 H), 2.59 (s, 6 H), 3.26 (s, 3 H), 6.96 (s, 1 H), 7.10 (d, J=9 Hz, 1 H), 7.24 (s, 1 H), 7.28 (d, J=2.1 Hz, 1 H), 7.49 (dd, JI=2.1 Hz, J2 =8.7 Hz, 1 H), 7.73 (s,1 H), 12.44 (s, 1 H).

The intermediate 4-Dimethylamino-3-(1,4,4,6-tetramethyl-2-oxo-1,2,3,4-tetrahydro-quinolin-7-yl)-benzaldehyde was prepared as followed:

a. 4-Dimethylamino-3-(1,4,4,6-tetramethyl-2-oxo-1,2,3,4-tetrahydro-quinolin-7-yl)-benzaldehyde.

A mixture of 6-dimethylamino-3-formyl-1-phenyl boronic acid (11.5 g, 59.5 mmol), 7-bromo-1,4,4,6-tetramethyl-3,4-dihydro-1H-quinoline-2-one (Example 1d) (14.0 g, 49.6 mmol) and potassium carbonate (13.7 g, 99.2 mmol) in toluene (140 mL), ethanol (28 mL) and water (21 mL) was degassed with argon for 40 minutes. Tetrakis(triphenylphosphine)palladium(0) (3.5 g, 0.06 mmol) was added and the mixture heated at reflux under argon for 24 hrs. The solution was cooled to room temperature, diluted with ethyl acetate and washed successively with water and brine, dried over anhydrous magnesium sulfate, filtered and evaporated. The residue was purified on silica gel (30% ethyl acetate in hexane) to give 14.66 g of 4-Dimethylamino-3-(1,4,4,6-tetramethyl-2-oxo-1,2,3,4-tetrahydro-quinolin-7-yl)-benzaldehyde (84%). $^1$H NMR (300 MHz; CDCl$_3$): 1.31 (s, 3 H), 1.33 (s, 3 H), 2.10 (s, 3 H), 2.53 (s, 2 H), 2.69 (s, 6 H), 3.36 (s, 3 H), 6.89 (s, 1 H), 6.99 (d, J=8.7 Hz, 1 H), 7.14 (s, 1 H), 7.58 (d, J=2.4 Hz, 1 H), 7.77 (dd, J=2.4 Hz and 8.4 Hz, 1 H), 9.82 (s, 1 H).

b. 6-dimethylamino-3-formyl-1-phenyl boronic acid.

To a mixture of 2-(3-bromo-4-dimethylamino-1-phenyl)-1,3-dioxolane (8.8 g, 32.34 mmol) in THF (80 mL) cooled to –78° C. under an atmosphere of argon was added n-BuLi (19.4 mL, 2.5 M, 48.50 mmol) dropwise. The resulting suspension was stirred for 5 minutes and triisopropylborate (22.4 mL, 97.0 mmol) was added dropwise via syringe. The mixture was stirred at –50° C. for 2 hours then warmed up to room temperature and stirred overnight at room temperature. 1.0 N HCl (50 mL) was slowly added to the reaction mixture. After 4 hours 10% aqueous potassium carbonate was added to the reaction mixture until pH=6~7. The solution was diluted with ethyl acetate and the layers separated. The organic layer was further washed with water, brine and dried (MgSO$_4$). The mixture was filtered and evaporated to afford 6.4 g of crude 6-dimethylamino-3-formyl-1-phenyl boronic acid used without further purification in the Suzuki coupling (step a).

c. 2-(3-bromo-4-dimethylamino-1-phenyl)-1,3-dioxolane.

To a solution of 3-bromo-4-dimethylamino-benzaldehyde (10 g, 43.84 mmol) in toluene (80 mL) was added ethylene glycol (48.9 mL, 877 mmol) and p-toluenesulfonic acid monohydrate (0.5 g; 2.63 mmol). The reaction mixture was heated at reflux overnight and the water was removed using a Dean Stark apparatus. The solution was cooled to room temperature, aqueous potassium carbonate (10%) was added and the solution extracted with ethyl acetate. The organic layer was washed with water, brine and dried (MgSO$_4$). The residue was purified on silica gel (eluent: 10% ethyl acetate in hexane) to give 10.84 g of 2-(3-bromo-4-dimethylamino-1-phenyl)-1,3-dioxolane. (90%). $^1$H NMR (300 MHz; CDCl$_3$): δ 2.81 (s, 6 H), 4.02 (m, 2 H), 4.13 (m, 2 H), 5.74 (s, 1 H), 7.06 (d, J=8.1 Hz, 1 H), 7.43 (dd, J=1.1 Hz and 8.4 Hz, 1 H), 7.69 (d, J=1.5 Hz, 1 H).

d. 3-bromo-4-dimethylamino-benzaldehyde.

To a solution of 4-dimethylamino-benzaldehyde (10 g, 67.03 mmol) in dichloromethane (250 mL) was added pyridinium tribromide (21.4 g, 67.03 mmol) and the reaction mixture stirred at room temperature overnight. The solution was washed with water and brine, dried (MgSO$_4$), filtered and evaporated. The residue was purified on silica gel (eluent: 15% ethyl acetate in hexane) to give 14.06 g of 3-bromo-4-dimethylamino-benzaldehyde (92%). $^1$H NMR (300 MHz; CDCl$_3$): δ 2.59 (s, 6 H), 7.06 (d, J=8.1 Hz, 1 H), 7.75 (dd, J=7.8 Hz and 1.5 Hz, 1 H), 5.74 (s, 1 H), 7.06 (d, J=8.1 Hz, 1 H), 7.43 (dd, J=2.1 Hz and 8.4 Hz, 1 H), 8.04 (d, J=1.8 Hz, 1 H), 9.81 (s, 1 H).

Example 4

5-[4-Dimethylamino-3-(1-ethyl-4,4,6-trimethyl-2-oxo-1,2,3,4-tetrahydro-quinolin-7-yl)-benzylidene]-thiazolidine-2,4-dione, Which can be Referred to as "Compound 4"

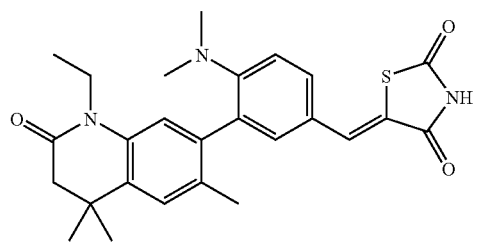

Prepared in a similar manner to example 1 using 4-Dimethylamino-3-(1-ethyl-4,4,6-trimethyl-2-oxo-1,2,3,4-tetrahydro-quinolin-7-yl)-benzaldehyde. 61% yield after recrystallisation from ethanol. mp 266–268° C. $^1$H-NMR (300 MHz, DMSO-d-6): 1.09 (t, J=6.6 Hz, 3 H), 1.27 (2 s, 6 H), 2.08 (s, 3 H), 2.49 (d, 2 H), 2.59 (s, 6 H), 3.98 (m, 2 H), 7.01 (s, 1 H), 7.10 (d, J=8.7 Hz, 1 H), 7.25 (s, 1 H), 7.28 (d, J=2.4 Hz,1 H), 7.50 (dd, J1=7.7 Hz, J2=2.1 Hz, 1H), 7.74 (s, 1 H), 7.84 (s, 1 H), 12.44 (br s, 1 H).

The intermediate 4-Dimethylamino-3-(1-ethyl-4,4,6-tetramethyl-2-oxo-1,2,3,4-tetrahydro-quinolin-7-yl)-benzaldehyde was prepared in a similar manner to example 3a using 6-dimethylamino-3-formyl-1-phenyl boronic acid (example 3b) and 7-bromo-1-ethyl-4,4,6-trimethyl-3,4-dihydro-1H-quinoline-2-one (example 2b). 59% yield. $^1$H NMR (300 MHz; CDCl$_3$): 1.21 (t, J=6.9 Hz, 3 H), 1.32 (s, 6 H), 2.12 (s, 3 H), 2.52 (s, 2 H), 2.70 (s, 6 H), 4.09 (m, 2 H), 6.93 (s, 1 H), 6.98 (d, J=8.7 Hz, 1 H), 7.16 (s, 1 H), 7.59 (d, J=2.1 Hz, 1 H), 7.77 (dd, J=2.1 Hz and 8.4 Hz, 1 H), 9.84 (s, 1 H).

Example 5

5-[3-(1,4,4,6-Tetramethyl-2-oxo-1,2,3,4-tetrahydro-quinolin-7-yl)-4-chloro-benzylidene]-thiazolidine-2,4-dione, Which can be Referred to as "Compound 5"

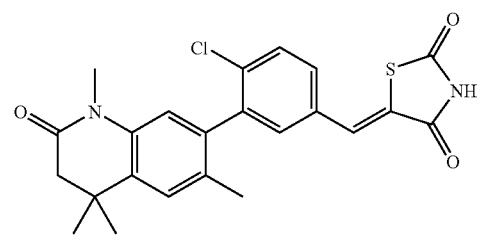

Prepared in a similar manner to example 1 using 4-chloro-3-(1,4,4,6-tetramethyl-2-oxo-1,2,3,4-tetrahydro-quinolin-7-yl)-benzaldehyde. 50% yield after recrystallisation from ethanol. mp 176–178° C. $^1$H-NMR (300 MHz, DMSO-d-6): 1.25 (s, 3 H), 1.28 (s, 3 H), 2.07 (s, 3 H), 2.50 (s, 2 H), 3.24 (s, 3 H), 7.90 (s, 1 H), 7.29 (s, 1 H), 7.56 (s, 1 H), 7.62 (d, J=8.7 Hz, 1 H), 7.73 (d, J=8.1 Hz, 1 H), 7.83 (s, 1 H), 12.68 (br s, 1 H).

The intermediate 4-chloro-3-(1,4,4,6-tetramethyl-2-oxo-1,2,3,4-tetrahydro-quinolin-7-yl)-benzaldehyde was prepared as follows:

a. 4-chloro-3-(1,4,4,6-tetramethyl-2-oxo-1,2,3,4-tetrahydro-quinolin-7-yl)-benzaldehyde.

A mixture of 6-chloro-3-formyl-1-phenyl boronic acid (1.18 g, 6.38 mmol), 7-bromo-1,4,4,6-tetramethyl-3,4-dihydro-1H-quinoline-2-one (Example 1d) (1.5 g, 5.32 mmol) and potassium carbonate (1.47 g, 10.64 mmol) in toluene (15 mL), ethanol (3 mL) and water (2 mL) was degassed with argon for 30 minutes. Pd (Ph$_3$)$_4$ (0.123 g, 0.02 mmol) was added and the mixture heated at reflux under argon overnight. The solution was cooled to room temperature, diluted with ethyl acetate and washed successively with water and brine, dried over anhydrous magnesium sulfate, filtered and evaporated. The residue was purified on silica gel (0 to 20% ethyl acetate in hexane) to give 0.514 g of 4-chloro-3-(1,4,4,6-tetramethyl-2-oxo-1,2,3,4-tetrahydro-quinolin-7-yl)-benzaldehyde (28%). $^1$H NMR (300 MHz; CDCl$_3$): 1.33 (s, 3 H), 1.36 (s, 3 H), 2.09 (s, 3 H), 2.55 (2 s, 2 H), 3.35 (s, 3 H), 6.76 (s, 1 H), 7.19 (s, 1 H), 7.65 (d, J=8.1 Hz, 1 H), 7.77 (d, J=2.1 Hz, 1 H), 7.97 (dd, J=2.1 and 8.4 Hz, 1 H), 10.02 (s, 1 H).

b. 6-chloro-3-formyl-1-phenyl boronic acid.

Prepared in a similar manner to example 1b using 2-(3-bromo-4-chloro-1-phenyl)-1,3-dioxolane e (70%). $^1$H NMR (300 MHz; DMSO-d$_6$+1 drop of D$_2$O): δ 7.61 (d, J=8.4 Hz, 1 H), 7.84 (dd, J$_1$=2.1 Hz, J$_2$=8.4 Hz, 1 H), 7.95 (d, J=2.4 Hz, 1 H), 10.0 (s, 1 H).

c. 2-(3-bromo-4-chloro-1-phenyl)-1,3-dioxolane.

Prepared in a similar manner to example 1c using 3-bromo-4-chlorobenzaldehyde (90%). $^1$H NMR (500 MHz; CDCl$_3$): δ 4.03 (m, 2 H), 4.09 (m, 2 H), 5.79 (s, 1 H), 7.35 (dd, J=2.1 Hz and 8.4 Hz, 1 H), 7.44 (d, J=8.1 Hz, 1 H), 7.74 (d, J=2.1 Hz, 1 H).

d. 3-bromo-4-chlorobenzaldehyde.

To a solution of 4-chlorobenzaldehyde (20.5 g, 0.142 mol) in trifluoroacetic acid (83 mL) and sulfuric acid (16.6 mL) was added N-bromosuccinimide (51.6 g, 0.288 mol) in portion over 6 hrs. The reaction mixture was stirred at room temperature for 4 days. The solution was poured on ice-water and extracted with dichloromethane. The organic layer was washed with water, saturated aqueous NaHCO$_3$, water and brine, dried (MgSO$_4$), filtered and evaporated. The residue was taken up in hexane, filtered and evaporated to give 20.4 g of crude 3-bromo-4-chlobenzaldehyde that was used without purification in the next step (5c). $^1$H NMR (300 MHz; CDCl$_3$): 7.62 (d, J=8.1 Hz, 1 H), 7.80 (dd, J=2.1 and 8.4 Hz, 1 H), 8.12 (d, J=1.5 Hz, 1 H), 9.94 (s, 1 H).

Example 6

5-[3-(1-Ethyl-4,4,6-trimethyl-2-oxo-1,2,3,4-tetrahydro-quinolin-7-yl)-4-chloro-benzylidene]-thiazolidine-2,4-dione, Which can be Referred to as "Compound 6"

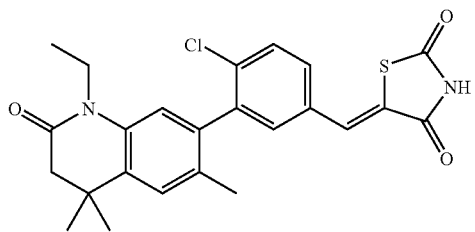

Prepared in a similar manner to example 1 using 4-chloro-3-(1-Ethyl-4,4,6-trimethyl-2-oxo-1,2,3,4-tetrahydro-quinolin-7-yl)-benzaldehyde. 41% yield after recrystallisation from ethanol. mp 221–223° C. 1H-NMR (300 MHz, DMSO-d-6): 1.07 (t, J=7.5 Hz, 3 H), 1.26 (2 s, 6H), 2.05 (s, 3 H), 2.46 (s, 2 H), 2.50 (m, 2 H), 3.95 (br d, 2 H), 6.94 (s, 1 H), 7.03 (s, 1 H), 7.56 (d, J=2.1 Hz, 1 H), 7.61 (dd, J=2.1 and 8.1 Hz, 1 H), 7.75 (d, J=8.1 Hz, 1 H), 7.84 (s, 1 H), 12.68 (br s, 1 H).

The intermediate 4-chloro-3-(1-Ethyl-4,4,6-trimethyl-2-oxo-1,2,3,4-tetrahydro-quinolin-7-yl)-benzaldehyde was prepared in a similar manner as example 5a using 7-bromo-1-ethyl-4,4,6-trimethyl-3,4-dihydro-1H-quinoline-2-one (example 2b) and 6-chloro-3-formyl-1-phenyl boronic acid (example 5b). Yield: 46%. $^1$H NMR (300 MHz, CDCl$_3$): 1.21 (t, J=6.9 Hz), 1.32 (s, 3 H), 1.34 (s, 3 H), 2.09 (s, 3 H), 2.53 (2 s, 2 H), 4.01 (m, 2 H), 6.76 (s, 1 H), 7.20 (s, 1 H), 7.65 (d, J=8.1 Hz, 1 H), 7.77 (d, J=2.1 Hz, 1 H), 7.84 (dd, J=2.1 and 8.4 Hz, 1 H), 10.02 (s, 1 H).

Example 7

5-[2-Fluoro-4-methoxy-3-(1,4,4,6-tetramethyl-2-oxo-1,2,3,4-tetrahydro-quinolin-7-yl)-benzylidene]-thiazolidine-2,4-dione, Which can be Referred to as "Compound 7"

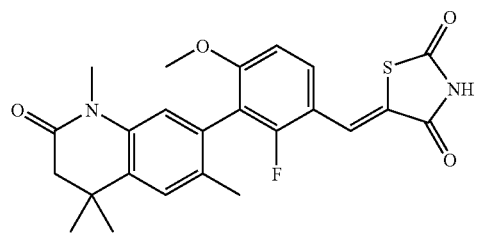

Prepared in a similar manner to example 1 using 2-Fluoro-4-methoxy-3-(1,4,4,6-tetramethyl-2-oxo-1,2,3,4-tetrahydro-quinolin-7-yl)-benzaldehyde. 64% yield.

mp 271–276° C. $^1$H-NMR (300 MHz, DMSO-d-6): 1.27 (s, 6 H), 2.01 (s, 3 H), 2.48 (s, 2 H), 3.22 (s, 3 H), 3.82 (s, 3 H), 6.90 (s, 1 H), 7.20 (d, J=8.8 Hz, 1 H), 7.28 (s, 1 H), 7.58 (t, J=8.8 Hz, 1 H), 7.76 (s, 1 H), 12.66 (br s, 1 H).

The intermediate 2-Fluoro-4-methoxy-3-(1,4,4,6-tetramethyl-2-oxo-1,2,3,4-tetrahydro-quinolin-7-yl)-benzaldehyde was prepared as follows:

a. 2-Fluoro-4-methoxy-3-(1,4,4,6-tetramethyl-2-oxo-1,2,3,4-tetrahydro-quinolin-7-yl)-benzaldehyde.

To a solution of 7-bromo-1,4,4,6-tetramethyl-3,4-dihydro-1H-quinoline-2-one (example 1d) (0.96 g, 3.40 mmol) in dioxane (2 mL) were added under argon, triethylamine 1.9 mL, 13.61 mmol), palladium acetate (38 mg, 0.17 mmol), 2-(dicyclohexylphosphino) biphenyl (238 mg, 0.68 mmol) and pinacolborane (1M in THF, 10.2 mL, 10.2 mmol). The mixture was stirred at 80° C. for 1 hr 45 min, then cooled to room temperature. Water (1.5 mL), barium hydroxide octahydrate (3.22 g, 10.20 mmol) and 2-Fluoro-3-iodo-4-methoxy benzaldehyde dissolved in dioxane (7 mL) were successively added and the mixture heated at 100° C. for 13 hrs. The mixture was cooled to room temperature and filtered over celite. Brine was added and the aqueous layer was extracted with dichloromethane. The organic extract was washed successively with water and brine, dried over anhydrous magnesium sulfate, filtered and evaporated. The residue was purified on silica gel (20% to 30% ethyl acetate in hexane) to give 0.63 g of 2-Fluoro-4-methoxy-3-(1,4,4,6-tetramethyl-2-oxo-1,2,3,4-tetrahydro-quinolin-7-yl)-benzaldehyde (52%). $^1$H NMR (300 MHz; CDCl$_3$): 1.33 (s, 3 H), 1.35 (s, 3 H), 2.09 (s, 3 H), 2.54 (s, 2 H), 3.35 (s, 3 H), 3.87 (s, 3 H), 6.79 (s, 1 H), 6.92 (d, J=8.7 Hz, 1 H), 7.21 (s, 1 H), 7.94 (t, J=8.7 Hz, 1 H), 10.25 (s, 1 H).

b. 2-Fluoro-3-iodo-4-methoxy benzaldehyde.

To a solution of 3-fluoroanisole (24 g, 190 mmol) in dichloromethane (350 mL) was added at room temperature pyridium tribromide (61 g, 190 mmol). The reaction mixture was stirred at room temperature for 24 hrs, then washed successively with water and brine, dried (MgSO$_4$), filtered and evaporated. The residue was chromatographed on silica gel (10% ethyl acetate in hexane) to give 34.5 g of 4-bromo- 3-fluoro anisole (88%) use as this in the next step. ¹H NMR (300 MHz; CDCl₃): 3.79 (s, 3 H), 6.62 (d, J=10 Hz, 1 H), 6.71 (d, J=10 Hz, 1 H), 7.40 (t, J=9 Hz, 1 H), 10.25 (s, 1 H).

To a solution of 4-bromo-3-fluoro anisole (34.4 g, 168 mmol) in anhydrous THF (300 mL) was added dropwise, at −78° C. under argon, n-BuLi (2.5 M in THF, 101 mL, 252 mol). After 5 min DMF (40 mL, 503 mmol) was added and the reaction micture was kept at −78° C. for 2 hrs. Aqueous NH₄Cl (250 mL) was carefully added and the layers separated. The aqueous phase was further extracted with ethyl acetate. The organic phases were combined and washed successively with water, brine and dried (MgSO₄). The residue was purified on silica gel (eluent: 10% ethyl acetate in hexane) to give 13.99 g of 2-fluoro-4-methoxy-benzaldehyde (54%). ¹H NMR (300 MHz; CDCl₃): 3.88 (s, 3 H), 6.65 (d, J=12.3 Hz, 1 H), 6.80 (d, J=8.7 Hz, 1 H), 7.82 (t, J=8.7 Hz, 1 H), 10.21 (s, 1 H).

To a solution of 2-fluoro-4-methoxy-benzaldehyde (13.98 g, 90.7 mmol) in toluene (100 mL) was added ethylene glycol (101 mL, 1.81 mol) and p-toluenesulfonic acid monohydrate (1.04 g, 5.44 mmol). The reaction mixture was heated at reflux for 16 hrs. The water was removed using a Dean Starck apparatus. After cooling, aqueous potassium carbonate (10%, 200 mL) was added and the mixture stirred for 30 minutes. The solution was extracted with ethyl acetate. The organic phase was washed successively with 10% aqueous potassium carbonate, brine and dried (MgSO₄). The residue was purified on silica gel (eluent: 10% ethyl acetate in hexane) to give 9.187 g of 2-(2-fluoro-4-methoxy-phenyl)-[1,3] dioxolane (51%). ¹H NMR (300 MHz; CDCl₃): 3.81 (s, 3 H), 4.06 (m, 2 H), 4.15 (m, 2 H), 6.03 (s, 1 H), 6.60 (dd, J=12.3 and 2.7 Hz, 1 H), 6.72 (d, J=8.4 Hz, 1 H), 7.44 (t, J=8.4 Hz, 1 H).

To a solution of 2-(2-fluoro-4-methoxy-phenyl)-[1,3] dioxolane (4.27 g, 21.54 mmol) in anhydrous THF (30 mL) was added, at −78° C. under argon, n-BuLi (1.6 M in hexane, 13.5, 21.54 mmol). The resulting orange solution was stirred at −78° C. for 2 hours then iodine (6.015 g, 23.70 mmol) in THF (30 mL) was added. At the end of the addition the reaction mixture was warmed to room temperature and stirred for 1 hr. The solution was extracted with ethyl acetate. The organic phase was washed successively with 10% aqueous sodium thiosulfate (2×50 mL), water, brine and dried (MgSO₄), filtered and evaporated to give 5.794 g of crude 2-(2-fluoro-3-iodo-4-methoxy-phenyl)-[1,3] dioxolane. use as this in the next step.

To a solution of 2-(2-fluoro-3-iodo-4-methoxy-phenyl)-[1,3] dioxolane (5.284 g, 16.30 mmol) in acetone (170 mL) was added HCl (1N, 170 mL) and the solution stirred at room temperature for 48 hrs. The solution was extracted with ethyl acetate and washed successively with water, brine, dried (MgSO₄), filtered and evaporated. The residue was purified on silica gel (eluent: 10% ethyl acetate in hexane) to give 2.22 g of 2-Fluoro-3-iodo-4-methoxy benzaldehyde (38% for 2 steps). ¹H NMR (300 MHz; CDCl₃): 4.00 (s, 3 H), 6.74 (d, J=8.4 Hz, 1 H), 7.88 (t, J=8.1 Hz, 1 H), 10.21 (s, 1 H).

Example 8

5-[3-(1-Propyl-4,4,6-trimethyl-2-oxo-1,2,3,4-tetrahydro-quinolin-7-yl)-4-trifluoromethoxy-benzylidene]-thiazolidine-2,4-dione, Which can be Referred to as "Compound 8"

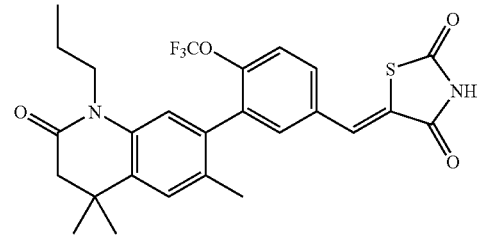

Prepared in a similar manner to example 1 using 3-(1-Porpyl-4,4,6-trimethyl-2-oxo-1,2,3,4-tetrahydro-quinolin-7-yl)-4-trifluoromethoxy-benzaldehyde. 45% yield after crystallization from ethyl acetate and hexane. mp 219–223° C. ¹H-NMR (300 MHz, DMSO-d-6): 0.84 (t, J=7.2 Hz, 3 H), 1.26 (s, 6 H), 1.49 (m, 2 H), 2.07 (s, 3 H), 2.46 (s, 2 H), 3.95 (br d, 2 H), 6.97 (s, 1 H), 7.31 (s, 1 H), 7.63 (d, J=1.8 Hz, 1 H), 7.66 (d, J=8.1 Hz, 1 H), 7.75 (dd, J₁=2.4 Hz, J₂=8.7 Hz, 1 H), 7.87 (s, 1 H), 12.71 (br s, 1 H). The intermediate 3-(1-propyl-4,4,6-trimethyl-2-oxo-1,2,3,4-tetrahydro-quinolin-7-yl)-4-trifluoromethoxy-benzaldehyde was prepared as follows:

a. 3-(1-Propyl-4,4,6-trimethyl-2-oxo-1,2,3,4-tetrahydro-quinolin-7-yl)-4-trifluoromethoxy-benzaldehyde.

A mixture of 3-formyl-6-trifluoromethoxy-1-phenyl boronic acid (Example 1b) (0.905 g, 3.87 mmol), 7-bromo-1-propyl-4,4,6-trimethyl-3,4-dihydro-1H-quinoline-2-one (1.0 g, 3.22 mmol) and potassium carbonate (0.89 g, 6.44 mmol) in toluene (10 mL), ethanol (2 mL) and water (1.5 mL) was degassed with argon for 30 minutes. Tetrakis (triphenylphosphine)palladium(0) (0.186 g, 0.161 mmol) was added and the mixture heated at reflux under argon for 24 hrs. The solution was cooled to room temperature, diluted with ethyl acetate and washed successively with water and brine, dried over anhydrous magnesium sulfate, filtered and evaporated. The residue was purified on silica gel (0–15% ethyl acetate in hexane) to give 0.70 g of 3-(1-propyl-4,4,6-trimethyl-2-oxo-1,2,3,4-tetrahydro-quinolin-7-yl)-4-trifluoromethoxy-benzaldehyde (52%). ¹H NMR (300 MHz; CDCl₃): 0.92 (t, J=7.2 Hz, 3 H), 1.33 (s, 6 H), 1.61 (m, 5 H), 2.09 (s, 3 H), 2.53 (s, 2 H), 3.95 (br d, 2 H), 6.78 (s, 1 H), 7.19 (s, 1 H), 7.55 (d, J=8.1 Hz, 1 H), 7.83 (d, J=2.1 Hz, 1 H), 7.98 (dd, J=2.1 and 8.74 Hz, 1 H), 10.05 (s, 1 H).

b. 7-bromo-1-propyl-4,4,6-trimethyl-3,4-dihydro-1H-quinoline-2-one.

A mixture of powdered potassium hydroxide (1.26 g, 22.38 mmol) in DMSO (40 mL) was stirred at 0° C. for 10 min. 7-bromo-4,4,6-trimethyl-3,4- dihydro-1H-quinoline-2-one (Example 1e) (3.0 g, 11.19 mmol) was added cautiously, followed immediately by the addition of 1-iodopropane (5.5 mL, 55.95 mmol). The reaction mixture was warmed up to room temperature and stirred overnight at room temperature. The reaction mixture was poured into water and extracted with dichloromethane washed with water and brine, dried (MgSO₄), filtered and evaporated to give 4.0 g of 7-bromo-1-propyl-4,4,6-trimethyl-3,4-dihydro-1H-quinoline-2-one and used without further purification in the Suzuki coupling (step a). ¹H NMR (300 MHz; CDCl₃): 0.98 (t, J=7.5 Hz,1 H), 1.26 (s, 6 H), 1.65 (t, J=7.5 Hz, 1 H), 2.37 (s, 3 H), 2.46 (s, 2 H), 3.88 (t, J=7.8 Hz, 2 H), 7.13 (s, 1 H), 7.15 (s, 1 H).

Example 9

5-[4-Dimethylamino-3-(1-propyl-4,4,6-trimethyl-2-oxo-1,2,3,4-tetrahydro-quinolin-7-yl)-benzylidene]-thiazolidine-2,4-dione, Which can be Referred to as "Compound 9"

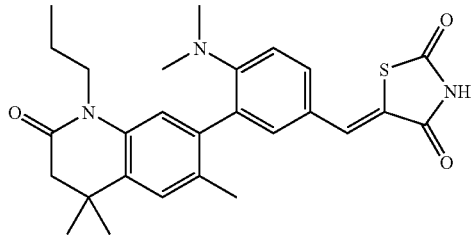

Prepared in a similar manner to example 1 using 4-Dimethylamino-3-(1-propyl-4,4,6-trimethyl-2-oxo-1,2,3,4-tetrahydro-quinolin-7-yl)-benzaldehyde. 67% yield after recrystallisation from ethanol. mp 258–260° C. ¹H-NMR (300 MHz, DMSO-d-6): 0.86 (t, J=7.5 Hz, 3 H), 1.24 (s, 3 H), 1.26 (s, 3 H), 1.53 (m, 2 H), 2.07 (s, 3 H), 2.46 (2 s, 2 H), 2.58 (s, 6 H), 3.90 (br m, 2 H), 7.02 (s,1 H), 7.10 (d, J=9.0 Hz, 1 H), 7.25 (s+d, 2 H), 7.50 (dd, J₁=2.1 Hz, J₂=8.4 Hz, 1 H), 7.74 (s, 1 H), 12.44 (br s, 1 H).

The intermediate 4-Dimethylamino-3-(1-propyl-4,4,6-tetramethyl-2-oxo-1,2,3,4-tetrahydro-quinolin-7-yl)-benzaldehyde was prepared in a similar manner to example 3a using 6-dimethylamino-3-formyl-1-phenyl boronic acid (example 3b) and
7-bromo-1-propyl-4,4,6-trimethyl-3,4-dihydro-1H-quinoline-2-one (example 8b). 57% yield. ¹H NMR (300 MHz; CDCl₃): 0.93 (t, J=7.2 Hz, 3 H), 1.32 (2 s, 6 H), 1.64 (m, 5 H), 2.12 (s, 3 H), 2.68 (s, 6 H), 3.91 (m, 2 H), 6.89 (s, 1 H), 6.98 (d, J=8.1 Hz, 1 H), 7.15 (s, 1 H), 7.59 (d, J=2.1 Hz, 1 H), 7.78 (dd, J=2.1 Hz and 8.4 Hz, 1 H), 9.83 (s, 1 H).

Example 10

5-[3-(1-Ethyl-4,4,6-trimethyl-2-oxo-1,2,3,4-tetrahydro-quinolin-7-yl)-2-fluoro-4-methoxy-benzylidene]-thiazolidine-2,4-dione, Which can be Referred to as "Compound 10"

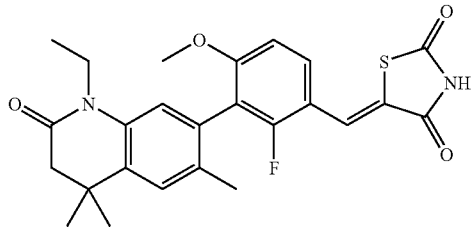

Prepared in a similar manner to example 1 using 2-Fluoro-4-methoxy-3-(1-ethyl-4,4,6-trimethyl-2-oxo-1,2,3,4-tetrahydro-quinolin-7-yl)-benzaldehyde. 81% yield after recrystallisation from ethanol. mp 279–281° C. ¹H-NMR (300 MHz, DMSO-d-6): 1.05 (t, J=6.7 Hz, 3 H), 1.25 (s, 6 H), 2.01 (s, 3 H), 2.46 (s, 2 H), 3.83 (s, 3 H), 3.93 (q, J=6.7 Hz, 2 H), 6.94 (s, 1 H), 7.20 (d, J=8.8 Hz,1 H), 7.28 (s, 1 H), 7.58 (t, J=8.8 Hz, 1H), 7.77 (s, 1 H), 12.65 (br s, 1 H).

The intermediate 2-Fluoro-4-methoxy-3-(1-ethyl-4,4,6-trimethyl-2-oxo-1,2,3,4-tetrahydro-quinolin-7-yl)-benzaldehyde was prepared in a similar manner to example 7a using 7-bromo-1-ethyl-4,4,6-trimethyl-3,4-dihydro-1H-quinoline-2-one (example 2b) and 2-Fluoro-3-iodo-4-methoxy benzaldehyde (example 7b). 59% yield. ¹H NMR (300 MHz; CDCl₃): 1.21 (t, J=6.9 Hz, 3 H), 1.31 (s, 3 H), 1.34 (s, 3 H), 1.60 (s, 2 H), 2.10 (s, 3 H), 2.52 (s, 2 H), 3.88 (s, 3 H), 4.02 (q, J=7.2 Hz, 1 H), 6.82 (s, 1 H), 6.93 (d, J=9.0 Hz, 1 H), 7.22 (s, 1 H), 7.95 (t, J=8.1 Hz, 1 H), 10.26 (s, 1 H).

Example 11

5-[3-(1-Isopropyl-4,4,6-trimethyl-2-oxo-1,2,3,4-tetrahydro-quinolin-7-yl)-4-trifluoromethoxy-benzylidene]-thiazolidine-2,4-dione, Which can be Referred to as "Compound 11"

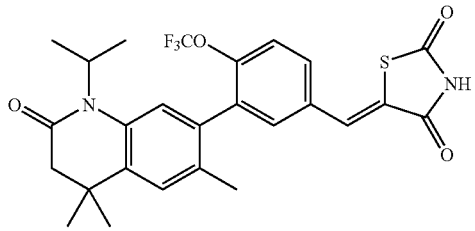

Prepared in a similar manner to example 1 using 3-(1-isopropyl-4,4,6-trimethyl-2-oxo-1,2,3,4-tetrahydro-quinolin-7-yl)-4-trifluoromethoxy-benzaldehyde. 48% yield after crystallization from ethanol/water. mp 233–235° C. 1H-NMR (300 MHz, DMSO-d-6): 1.26 (s, 6 H), 1.38 (s, 3 H), 1.40 (s, 3 H), 2.07 (s, 3 H), 2.38 (s, 2 H), 4.62 (m, 1 H), 6.98 (s, 1 H), 7.28 (s, 1 H), 7.66 (m, 2 H), 7.76 (dd, J₁=1.8 Hz, J₂=8.7 Hz, 1 H), 7.87 (s, 1 H), 12.71 (br s, 1 H).

The intermediate 3-(1-isopropyl-4,4,6-trimethyl-2-oxo-1,2,3,4-tetrahydro-quinolin-7-yl)-4-trifluoromethoxy-benzaldehyde was prepared as follows:

a. 3-(1-Isoropyl-4,4,6-trimethyl-2-oxo-1,2,3,4-tetrahydro-quinolin-7-yl)-4-trifluoromethoxy-benzaldehyde.

A mixture of 3-formyl-6-trifluoromethoxy-1-phenyl boronic acid (Example 1b) (1.09 g, 4.64 mmol), 7-bromo-1-isopropyl-4,4,6-trimethyl-3,4-dihydro-1H-quinoline-2-one (1.2 g, 3.87 mmol) and potassium carbonate (1.07 g, 7.74 mmol) in toluene (10 mL), ethanol (2 mL) and water (1.5 mL) was degassed with argon for 30 minutes. Tetrakis(triphenylphosphine)palladium(0) (0.224 g, 0.194 mmol) was added and the mixture heated at reflux under argon for 24 hrs. The solution was cooled to room temperature, diluted with ethyl acetate and washed successively with water and brine, dried over anhydrous magnesium sulfate, filtered and evaporated. The residue was purified on silica gel (0–15% ethyl acetate in hexane) to give 0.54 g of 3-(1-isopropyl-4,4,6-trimethyl-2-oxo-1,2,3,4-tetrahydro-quinolin-7-yl)-4-trifluoromethoxy-benzaldehyde (33%). ¹H NMR (300 MHz; CDCl₃): 1.32 (s, 6 H), 1.48 (s, 3 H), 1.50 (s, 3 H), 2.09 (s, 3 H), 2.45 (s, 2 H), 4.7 (m, 1 H), 6.91 (s, 1 H), 7.16 (s, 1 H), 7.55 (d, J=8.4 Hz, 1 H), 7.84 (d, J=1.8 Hz, 1 H), 7.98 (dd, J=1.8 and 8.4 Hz, 1 H), 10.05 (s, 1 H).

b. 7-bromo-1-isopropyl-4,4,6-trimethyl-3,4-dihydro-1H-quinoline-2-one.

Prepared in a similar manner to example 1d using 7-bromo-4,4,6-trimethyl-3,4-dihydro-1H-quinoline-7-yl)-2-one (example 1e) and 2-iodopropane. 72% yield. ¹H NMR (300 MHz; CDCl₃): 1.25 (s, 1 H), 1.51 (s, 3 H), 1.53 (s, 3 H), 2.36 (s, 3 H), 2.38 (s, 2 H), 4.62 (m, 1 H), 7.10 (s, 1 H), 7.27 (s, 1 H).

Example 12

5-[4-Dimethylamino-3-(1-isopropyl-4,4,6-trimethyl-2-oxo-1,2,3,4-tetrahydro-quinolin-7-yl)-benzylidene]-thiazolidine-2,4-dione, Which can be Referred to as "Compound 12"

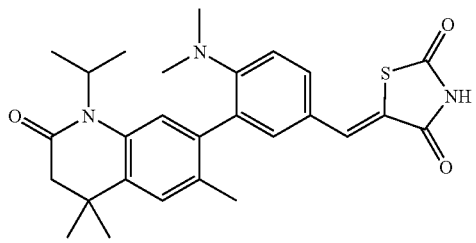

Prepared in a similar manner to example 1 using 4-Dimethylamino-3-(1-isopropyl-4,4,6-trimethyl-2-oxo-1,2,3,4-tetrahydro-quinolin-7-yl)-benzaldehyde. 72% yield. mp 274–276° C. $^1$H-NMR (300 MHz, DMSO-d-6): 1.24 (s, 3 H), 1.26 (s, 3 H), 1.40 (m, 6 H), 2.08 (s, 3 H), 2.38 (d, 2 H), 2.58 (s, 6 H), 4.71 (m, 1 H), 7.02 (s, 1 H), 7.12 (d, J=9 Hz, 1 H), 7.22 (s, 1 H), 7.28 (d, J=2.1 Hz, 1 H), 7.50 (dd, $J_1$=1.8 Hz, $J_2$=8.7 Hz, 1 H), 7.75 (s, 1 H), 12.45 (br s, 1 H).

The intermediate 4-Dimethylamino-3-(1-isopropyl-4,4,6-tetramethyl-2-oxo-1,2,3,4-tetrahydro-quinolin-7-yl)-benzaldehyde was prepared in a similar manner to example 3a using 6-dimethylamino-3-formyl-1-phenyl boronic acid (example 3b) and 7-bromo-1-isopipyl-4,4,6-trimethyl-3,4-dihydro-1H-quinoline-2-one (example 11b). 48% yield. $^1$H NMR (300 MHz; CDCl$_3$): 1.31 (s, 6 H), 1.48 (s, 6 H), 2.10 (s, 3 H), 2.44 (s, 2 H), 2.69 (s, 6 H), 4.76 (m, 2 H), 6.98 (d, 1 H), 7.02 (s, 1 H), 7.12 (s, 1 H), 7.59 (d, J=1.5 Hz, 1 H), 7.77 (dd, J=1.5 Hz and 8.7 Hz, 1 H), 9.83 (s, 1 H).

Example 13

5-[3-(1-Ethyl-4,4,6-trimethyl-2-oxo-1,2,3,4-tetrahydro-quinolin-7-yl)-2,5-difluoro-4-methoxy-benzylidene]-thiazolidine-2,4-dione, Which can be Referred to as "Compound 13"

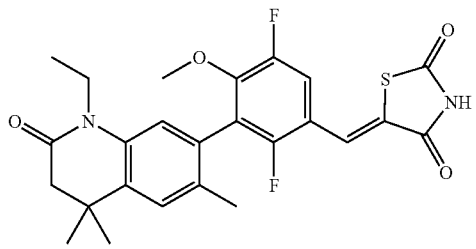

Prepared in a similar manner to example 1 using 3-(1-ethyl-4,4,6-trimethyl-2-oxo-1,2,3,4-tetrahydro-quinolin-7-yl)-2,5-difluoro-4-methoxy-benzaldehyde. 22% yield after recrystallisation from dichloromethane and hexane. mp 203–207° C. 1H NMR (300 MHz; DMSO) 1.05 (t, J=6.9 Hz, 3 H), 1.25 (s, 6 H), 2.05 (s, 3 H), 2.47 (s, 2 H), 3.80 (s, 3 H), 3.94 (m, 1 H), 7.04 (s, 1 H), 7.31 (s, 1 H), 7.47 (dd, $J_1$=6.9 Hz, $J_2$=12.3 Hz, 1 H), 12.77 (s, 1 H).

The intermediate 3-(1-ethyl-4,4,6-trimethyl-2-oxo-1,2,3,4-tetrahydro-quinolin-7-yl)-2,5-difluoro-4-methoxy-benzaldehyde was prepared in a similar manner to example 7a using 7-bromo-1-ethyl-4,4,6-trimethyl-3,4-dihydro-1H-quinoline-2-one (example 2b) and 3-bromo-2,5-difluoro-4-methoxy benzaldehyde. 14% yield. $^1$H NMR (300 MHz; CDCl$_3$): 1.21 (t, J=6.9 Hz, 3 H), 1.32 (s, 3 H), 1.33 (s, 3 H), 2.13 (s, 3 H), 2.53 (s, 2 H), 3.81 (2 s, 3 H), 4.02 (q, J=6.9 Hz, 1 H), 6.81 (s, 1 H), 7.23 (s, 1 H), 7.68 (dd, $J_1$=6.3 Hz, $J_2$=11.7 Hz, 1 H), 10.25 (2 s, 1 H).

a. 3-bromo-2,5-difluoro-4-methoxy benzaldehyde

Hexamethyltetramine (53.88 g, 0.384 mmol) was added carefully to TFA (140 mL) and the solution warmed to 80° C. A solution of 2,5-dinitrophenol (25 g, 0.192 mmol) in THF (60 mL) was added dropwise to the reaction mixture and the reaction stirred for 3 hrs at 80° C. The solution was diluted with toluene and the TFA removed under reduced pressure. The solution was then poured into ice-water and extracted with ethylacetate, washed successively with water, saturated aqueous NaHCO$_3$ (to pH=6), water and brine, dried (MgSO$_4$), filtered and evaporated to give 17 g of crude 2,5-difluoro-4-hydroxybenzaldehyde use as this in the next step.

To a solution of 2,5-difluoro-4-hydroxybenzaldehyde (37.5 g, 0.237 mmol) in dichloromethane (1.5 L) was added pyridinium tribromide (75.9 g, 0.237 mmol). The reaction mixture was stirred at 40° C. for 7 hrs then at room temperature overnight. The reaction was washed with water and brine, dried over magnesium sulfate, filtered and evaporated to give 48.4 g of crude 3-bromo-2,5-difluoro-4-hydroxybenzaldehyde use as this in the next step.

To a solution of 3-bromo-2,5-difluoro-4-hydroxybenzaldehyde (48.4 g, 0.193 mmol) in DMF (200 mL) was added potassium carbonate (40.0 g) and dimethylsulfate (27.4 mL). The reaction mixture was stirred at room temperature overnight. The reaction was diluted wit ethylacetate and washed successively with water and brine, dried over magnesium sulfate, filtered and evaporated. The residue was triturated with hexane to afford 26 g of 3-bromo-2,5-difluoro-4-methoxy benzaldehyde. The mother liquor was evaporated and chromatographed on silica gel (0–10% ethyl acetate in hexane) to give 10.86 g of more product. (38% overall yield from 2,5-dinitrophenol).

Example 14

5-[4-Ethylamino-3-(1-ethyl-4,4,6-trimethyl-2-oxo-1,2,3,4-tetrahydro-quinolin-7-yl)-benzylidene]-thiazolidine-2,4-dione, Which can be Referred to as "Compound 14"

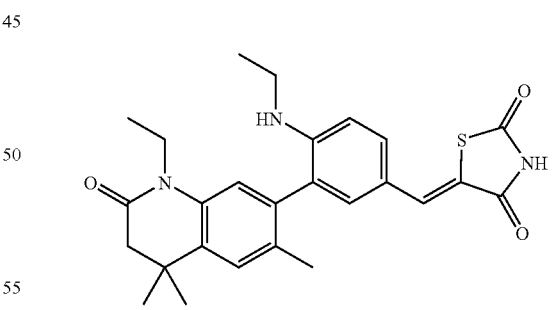

Prepared in a similar manner to example 1 using 4-ethylamino-3-(1-ethyl-4,4,6-trimethyl-2-oxo-1,2,3,4-tetrahydro-quinolin-7-yl)-benzaldehyde. 86% yield after crystallisation from dichloromethane and hexane. mp 283–285° C. $^1$H-NMR (300 MHz, DMSO-d-6): 1.08 (t, J=7.0 Hz, 3 H), 1.09 (t, J=7.0 Hz, 3 H), 1.25 (s, 3 H), 1.28 (s, 3 H), 2.06 (s, 3 H), 2.45 (d, J=3.5 Hz, 2 H), 3.22 (m, 2 H), 3.95 (m, 2 H), 5.19 (t, J=5.9 Hz, 1 H), 6.83 (d, J=8.8 Hz, 1 H), 6.89 (s, 1 H), 7.14 (d, J=2.3 Hz, 1 H), 7.30 (s, 1 H), 7.46 (dd, $J_1$=8.8 Hz $J_2$=2.3 Hz, 1 H), 7.69 (s, 1 H).

a. 4-ethylamino-3-(1-ethyl-4,4,6-trimethyl-2-oxo-1,2,3,4-tetrahydro-quinolin-7-yl)-benzaldehyde.

The intermediate 4-ethylamino-3-(1-ethyl-4,4,6-trimethyl-2-oxo-1,2,3,4-tetrahydro-quinolin-7-yl)-benzaldehyde was prepared in a similar manner to example 7a using 7-bromo-1-ethyl-4,4,6-trimethyl-3,4-dihydro-1H-quinoline-2-one (example 2b) and 3-bromo-4-ethylamino benzaldehyde. 53% yield. $^1$H NMR (300 MHz; CDCl$_3$): 1.21 (t, J=6.9 Hz, 3 H), 1.31 (s, 3 H), 1.35 (s, 3 H), 2.08 (s, 3 H), 2.53 (s, 2 H), 3.27 (m, 2 H), 4.02 (q, J=7.5 Hz, 1 H), 6.75 (d, J=8.7 Hz, 1 H), 6.83 (s, 1 H), 7.21 (s, 1 H), 7.52 (s, 1 H), 7.81 (d, J=8.4 Hz, 1 H), 9.76 (s, 1 H).

b. 3-bromo-4-ethylamino benzaldehyde.

To a solution of 4-diethylamino-benzaldehyde (10 g, 56.4 mmol) in dichloromethane (300 mL) was added at room temperature pyridium tribromide (54 g, 169.2 mmol). The reaction mixture was stirred at room temperature for 48 hrs, then it was washed successively with water and brine, dried (MgSO$_4$), filtered and evaporated. The residue was chromatographed on silica gel (10% ethyl acetate in hexane) to give 10.3 g of 3-bromo-4-ethylamino benzaldehyde (80%). $^1$H NMR (300 MHz; CDCl$_3$): 1.38 (t, J=6.9 Hz, 3 H), 3.31 (m, 2 H), 4.92 (br s, 1 H), 6.67 (d, J=9 Hz, 1 H), 7.69 (dd, J$_1$=1.5 Hz, J$_2$=8.1 Hz, 1 H), 7.95 (d, J=1.5 Hz, 1 H), 9.68 (s, 1 H).

Example 15

6-[2-Dimethylamino-5-(2,4-dioxo-thiazolidin-5-ylidenemethyl)-phenyl]-1,4,7-trimethyl-1,4-dihydro-quinoxaline-2,3-dione, which can be Referred to as "Compound 15"

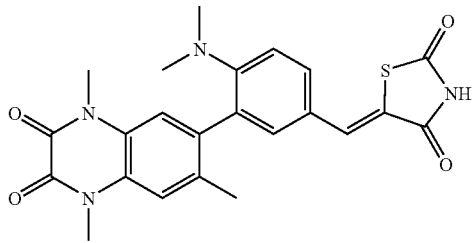

Prepared in a similar manner to example 1 using 4-Dimethylamino-3-(1,4,7-trimethyl-2,3-dioxo-1,2,3,4-tetrahydro-quinoxalin-6-yl)-benzaldehyde (8%). mp 247–251° C. $^1$H-NMR (300 MHz, DMSO-d-6): 2.15 (s, 3 H), 2.58 (s, 6 H), 3.51 (s, 3 H), 3.57 (s, 3 H), 7.12 (d, J=8.8 Hz, 1 H), 7.26 (s, 1 H), 7.28 (d, 1H, J=2.3 Hz), 7.36 (s, 1 H), 7.50 (dd, J$_1$=2.3 Hz, J$_2$=8.8 Hz, 1 H), 7.72 (s, 1 H), 12.4 (br s, 1 H).

The intermediate 4-Dimethylamino-3-(1,4,7-trimethyl-2,3-dioxo-1,2,3,4-tetrahydro-quinoxalin-6-yl)-benzaldehyde was prepared in a similar manner to example 3a using 6-dimethylamino-3-formyl-1-phenyl boronic acid (example 3b) and 6-bromo-1,4,7-trimethyl-1,4-dihydro-quinoxaline-2,3-dione (18%). $^1$H NMR (300 MHz; CDCl$_3$): 2.12 (s, 3 H), 2.69 (s, 6 H), 3.65 (s, 6 H), 7.1–7.6 (m, 5 H), 9.84 (s, 1 H).

a. 6-bromo-1,4,7-trimethyl-1,4-dihydro-quinoxaline-2,3-dione.

To a solution of 1,4,6-trimethyl-1,4-dihydro-quinoxaline-2,3-dione (0.66 g, 3.2 mmol) in acetic acid (40 mL) was added bromine (0.52 g, 3.2 mmol) and the solution stirred at 50° C. overnight. The reaction mixture was cooled to room temperature and poured into water. The solution was neutralized with aqueous NaOH to Ph=7, extracted with dichloromethane and washed with brine, dried (MgSO$_4$), filtered and evaporated to give 0.9 g of 6-bromo-1,4,7-trimethyl-1,4-dihydro-quinoxaline-2,3-dione used without further purification in the Suzuki coupling (step a). $^1$H NMR (300 MHz; CDCl$_3$): 2.47 (s, 3 H), 3.64 (s, 6 H), 7.09 (s, 1 H), 7.40 (s, 1 H).

b. 1,4,6-trimethyl-1,4-dihydro-quinoxaline-2,3-dione.

To a solution of 6-methyl-1,4-dihydro-quinoxaline-2,3-dione (5.3 g, 30 mmol) in THF (150 mL) was added, at 0° C. under argon, sodium hydride (3.68 g, 80% in mineral oil, 120 mmol) followed by methyl iodide (7.5 mL, 120 mmol). The solution was stirred at 0° C. for 3 hrs and at room temperature overnight. The reaction mixture was cooled to 0° C. and acidified with 1N HCl. The solution was extracted with dichloromethane washed with brine, dried (MgSO$_4$), filtered and evaporated. The residue was chromatographed on silica gel (10 to 25% acetonitrile in dichloromethane) to give 1.1 g of 1,4,6-trimethyl-1,4-dihydro-quinoxaline-2,3-dione (18%). $^1$H NMR (300 MHz; CDCl$_3$): 2.44 (s, 3 H), 3.66 (s, 6 H), 7.06–7.15 (m, 3 H).

C. 6-methyl-1,4-dihydro-quinoxaline-2,3-dione.

3,4-Diaminotoluene (24.4 g, 0.2 mmol) was dissolved in 2N HCl (300 mL), oxalic acide dihydrate (27.7 g, 0.22 mmol) was added and the mixture was heated at reflux for 3.5 hrs. The reaction mixture was cooled to room temperature, filtered, washed with water, dried (MgSO$_4$), filtered and evaporated to give 34 g of 6-methyl-1,4-dihydro-quinoxaline-2,3-dione (96%). $^1$H NMR (300 MHz; CDCl$_3$): 2.25 (s, 3 H), 6.87–6.99 (m, 3 H), 11.87 (br s, 2 H).

Example 16

5-[3-(1-Benzyl-3,3,5-trimethyl-2-oxo-2,3-dihydro-1H-indol-6-yl)-4-trifluoromethoxy-benzylidene]-thiazolidine-2,4-dione, Which can be Referred to as "Compound 16"

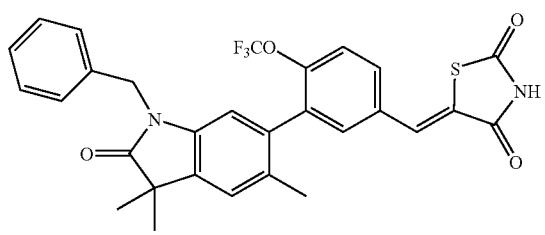

Prepared in a similar manner to example 1 using 3-(1-Benzyl-3,3,5-trimethyl-2-oxo-2,3-dihydro-1H-indol-6-yl)-4-trifluoromethoxy-benzaldehyde. 72% yield. $^1$H-NMR (300 MHz, DMSO-d-6): 1.37 (s, 6 H), 2.03 (s, 3 H), 4.89 (s, 2 H), 6.77 (s, 1 H), 7.28 (m, 5 H), 7.37 (s, 1 H), 7.48 (d, J=2.0 Hz, 1 H), 7.61 (dd, J=1.6 Hz and 8.8 Hz, 1 H), 7.74 (dd, J=2.3 Hz and 8.8 Hz, 1 H), 7.82 (s, 1 H), 12.71 (br s, 1 H).

a. 3-(1-Benzyl-3,3,5-trimethyl-2-oxo-2,3-dihydro-1H-indol-6-yl)-4-trifluoromethoxy-benzaldehyde.

The intermediate 3-(1-Benzyl-3,3,5-trimethyl-2-oxo-2,3-dihydro-1H-indol-6-yl)-4-trifluoromethoxy-benzaldehyde was prepared in a similar manner to example 1a using 3-formyl-6-trifluoromethoxy-1-phenyl boronic acid (Example 1b) and trifluoro-methanesulfonic acid 1-benzyl-3,3,5-trimethyl-2-oxo-2,3-dihydro-1H-indol-6-yl ester. 27% yield. $^1$H NMR (300 MHz; CDCl$_3$): 1.48 (s, 6 H), 2.07 (s, 3 H), 4.89 (s, 2 H), 6.50 (s, 1 H), 1.74 (t, J=6.0 Hz, 2 H), 2.01

(s, 3 H), 2.69 (s, 6 H), 2.91 (dd, J=7.2 and 14.7 Hz, 1 H), 7.13 (s, 1 H), 7.27 (m, 5 H), 7.47 (d, J=8.4 Hz, 1 H), 7.71 (s, 1 H), 7.93 (d, J=8.4 Hz, 1 H)), 9.99 (s, 1 H).

b. Trifluoro-methanesulfonic acid 1-benzyl-3,3,5-trimethyl-2-oxo-2,3-dihydro-1H-indol-6-yl ester.

To a solution of 1-benzyl-6-hydroxy-3,3,5-trimethyl-1,3-dihydro-indol-2-one (1.85 g, 6.60 mmol) in anhydrous dichloromethane (30 mL) was added slowly, under argon at 0° C., pyridine (0.64 mL, 7.92 mmol) followed by triflic anhydride (1.33 mL, 7.92 mmol). The reaction was warmed up to room temperature and stirred overnight. The mixture was washed successively with water, 1N HCl, water, saturated aqueous NaHCO$_3$, water and brine. The organic extract was dried over MgSO$_4$, filtered and evaporated to give 2.6 g of trifluoro-methanesulfonic acid 1-benzyl-3,3,5-trimethyl-2-oxo-2,3-dihydro-1H-indol-6-yl ester (95% yield). $^1$H NMR (300 MHz; CDCl$_3$): 1.42 (s, 6 H), 2.31 (s, 3 H), 4.87 (s, 2 H), 6.55 (s, 1 H), 7.09 (s, 1 H), 7.29 (m, 5 H).

c. 1-benzyl-6-hydroxy-3,3,5-trimethyl-1,3-dihydro-indol-2-one.

To a solution of 1-benzyl-6-methoxy-3,3,5-trimethyl-1,3-dihydro-indol-2-one (1.52 g, 5.15 mmol) in anhydrous dichloromethane (50 mL) was added slowly, under argon at −78° C., BBr$_3$ (0.87 mL, 9.27 mmol). The reaction was warmed up to −20° C. and stirred overnight at room temperature. Water and the layer separated. The aqueous layer was neutralized with NaHCO$_3$ and extracted with dichloromethane. The organic combined extract was washed with aqueous NaHCO$_3$, water and brine, dried over MgSO$_4$, filtered and evaporated to give 1-benzyl-6-hydroxy-3,3,5-trimethyl-1,3-dihydro-indol-2-one (93% yield). $^1$H NMR (300 MHz; CDCl$_3$): 1.38 (s, 6 H), 2.19 (s, 3 H), 4.82 (s, 2 H), 5.47 (br s, 1 H), 6.26 (s, 1 H), 6.93 (s, 1 H), 7.26 (m, 5 H).

d. 1-benzyl-6-methoxy-3,3,5-trimethyl-1,3-dihydro-indol-2-one.

To a solution of N-benzyl-N-(2-bromo-5-methoxy-4-methyl-phenyl)-isobutyramide (4.35 g, 11.56 mmol) in 1,4-dioxane (115 mL) was added sodium tert-butoxide (1.66 g, 17.34 mmol). The mixture was degassed under argon for 30 minutes, then palladium (II) acetate (130 mg, 0.58 mmol) and tricyclohexylphosphine (162 mg, 0.58 mmol) were added and the mixture refluxed overnight. A solution of saturated aqueous ammonium chloride was added and the solution extracted with ethyl acetate. The organic extract was washed successively with water and brine, dried over MgSO$_4$, filtered and evaporated. The residue was chromatographed on silica gel (20% ethyl acetate in hexane) to give 1.94 g of 1-benzyl-6-methoxy-3,3,5-trimethyl-1,3-dihydro-indol-2-one (57% yield). $^1$H NMR (300 MHz; CDCl$_3$): 1.40 (s, 6 H), 2.16 (s, 3 H), 3.67 (s, 3 H), 4.90 (s, 2 H), 6.26 (s, 1 H), 6.96 (s, 1 H), 7.27 (m, 5 H).

e. N-benzyl-N-(2-bromo-5-methoxy-4-methyl-phenyl)-isobutyramide.

A mixture of powdered KOH (1.3 g, 23.13 mmol) in DMSO (25 mL) was stirred at 0° C. for 5 minutes. N-(2-bromo-5-methoxy-4-methyl-phenyl)-isobutyramide (3.30 g, 11.56 mmol) was added cautiously followed immediately by the addition of benzylbromide (2.75 mL, 23.13 mmol) and the reaction stirred at room temperature for 48 hrs. Water was added and the mixture extracted with ethyl acetate. The organic extract was washed successively with water and brine, dried over MgSO$_4$, filtered and evaporated. The residue was chromatographed on silica gel (20% ethyl acetate in hexane) to give 4.3 g of N-benzyl-N-(2-bromo-5-methoxy-4-methyl-phenyl)-isobutyramide (99% yield). $^1$H NMR (300 MHz; CDCl$_3$): 1.02 (d, J=6.6 Hz, 3 H), 1.15 (d, J=6.6 Hz, 3 H), 2.16 (s, 3 H), 2.29 (m, 1 H), 3.43 (s, 3 H), 3.85 (d, J=14.1 Hz, 1 H), 5.75 (d=14.1 Hz, 1 H), 6.02 (s, 1 H), 7.18–7.27 (m, 5 H), 7.38 (s, 1 H).

f. N-(2-bromo-5-methoxy-4-methyl-phenyl)-isobutyramide.

To a biphasic mixture of 2-bromo-5-methoxy-4-methyl-aniline (5.6 g, 25.96 mmol), 10% KOH (27 mL) and dichloromethane (30 mL), was added dropwise isobutyryl chloride (3 mL, 28.55 mmol) in dichloromethane (10 mL). The reaction mixture was stirred at room temperature for 48 hrs. The layers were separated. The aqueous layer was further extracted with dichloromethane and the combined organics washed successively with water and brine, dried over MgSO$_4$, filtered and evaporated to give 7.38 g of N-(2-bromo-5-methoxy-4-methyl-phenyl)-isobutyramide (99% yield). $^1$H NMR (300 MHz; CDCl$_3$): 1.29 (d, J=6.9 Hz, 6 H), 2.14 (s, 3 H), 2.59 (m, 1 H), 3.84 (s, 3 H), 7.24 (s, 1 H), 7.66 (br s, 1 H), 8.07 (s, 1 H).

g. 2-bromo-5-methoxy-4-methyl-aniline.

To a solution of 3-methoxy-4-methyl-aniline (8.19 g, 59.71 mmol) in dichloromethane (200 mL), was added tetrabutylammonium tribromide (28.79 g, 59.71 mmol) and the reaction mixture was stirred at room temperature for 2.5 hrs. Aqueous NaHCO$_3$ was added and the layers separated. The aqueous layer was further extracted with dichloromethane and the combined organics washed successively with water and brine, dried over MgSO$_4$, filtered and evaporated. The residue was chromatographed on silica gel (20% ethyl acetate in hexane) to give 11.05 g of 2-bromo-5-methoxy-4-methyl-aniline (85% yield). $^1$H NMR (300 MHz; CDCl$_3$): 2.09 (s, 3 H), 3.75 (s, 3 H), 3.95 (br s, 1 H), 6.27 (s, 1 H), 7.13 (s, 1 H).

h. 3-methoxy-4-methyl-aniline.

To a solution of 2-methyl-5-nitroanisole (11.56 g, 69.2 mmol) in a mixture of ethyl acetate (200 mL) and ethanol (70 mL) was added portionwise tin (II) chloride dihydrate (109 g, 0.483 mol) and the mixture was stirred at room temperature overnight. The reaction mixture was basified with aq. K$_2$CO$_3$ and filtered over celite. The layers were separated. The aqueous layer was further extracted with ethyl acetate and the combined organics washed successively with water and brine, dried over MgSO$_4$, filtered and evaporated to give 8.02 g of 3-methoxy-4-methyl-aniline (86% yield). $^1$H NMR (300 MHz; CDCl$_3$): 2.09 (s, 3 H), 3.76(s, 3 H), 4.01 (br s, 1 H), 6.20 (m, 2 H), 6.90 (d, J=8.4 Hz, 1 H).

Example 17

5-[3-(1-Ethyl-4,4,6-trimethyl-2-oxo-1,2,3,4-tetrahydro-quinolin-7-yl)-5-fluoro-4-methoxy-benzylidene]-thiazolidine-2,4-dione, which can be Referred to as "Compound 17"

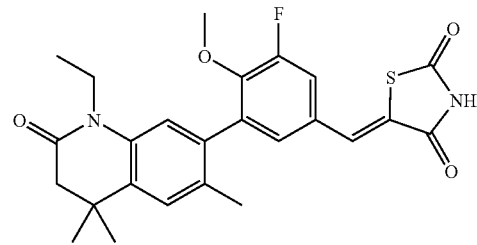

Prepared in a similar manner to example 1 using 3-(1-ethyl-4,4,6-trimethyl-2-oxo-1,2,3,4-tetrahydro-quinolin-7-yl)-5-fluoro-4-methoxy-benzaldehyde. 36% yield, mp 260–262° C. $^1$H-NMR (300 MHz, DMSO-d-6): 1.08 (t, J=6.7 Hz, 3 H), 1.25 (s, 6 H), 2.09 (s, 3 H), 2.46 (s, 2 H), 3.83 (s, 3 H), 3.96 (q, J=6.7 Hz, 2 H), 6.98 (s, 1 H), 7.25 (br s, 1 H), 7.28 (s, 1 H), 7.56 (dd, J$_1$=12.6 Hz, J$_2$=2.0 Hz, 1 H), 7.80 (s, 1 H), 12.67 (br s, 1 H).

The intermediate 3-(1-ethyl-4,4,6-trimethyl-2-oxo-1,2,3,4-tetrahydro-quinolin-7-yl)-5-fluoro-4-methoxy-benzaldehyde was prepared in a similar manner to example 7a using 7-bromo-1-ethyl-4,4,6-trimethyl-3,4-dihydro-1H-quinoline-2-one (example 2b) and 3-bromo-5-fluoro-4-methoxy-benzaldehyde. 12% yield. $^1$H-NMR (300 MHz, CDCl$_3$): 1.23 (t, J=7.0 Hz, 3 H), 1.33 (s, 6 H), 2.13 (s, 3 H), 2.53 (s, 2 H), 3.91 (s, 3 H), 4.01 (q, J=7.0 Hz, 2 H), 6.83 (s, 1 H), 7.19 (s, 1 H), 7.50 (d, J=1.8 Hz, 1 H), 7.66 (dd, J$_1$=11.7 Hz, J$_2$=2.1 Hz, 1 H), 9.91 (s, 1 H).

The intermediate 3-bromo-5-fluoro-4-methoxy-benzaldehyde was prepared in a similar manner to example 5d using 3-fluoro-4-methoxy-benzaldehyde. It was used without purification in the next step. $^1$H-NMR (300 MHz, CDCl$_3$): 4.11 (s, 3 H), 7.60 (d, J=11.1 Hz, 1 H), 7.87 (s, 1 H), 9.87 (s, 1 H).

Example 18

5-(1'-Ethyl-4',4',6'-trimethyl-2'-oxo-1',2',3',4'-tetrahydro-[4,7']biquinolinyl-2-ylmethylene)-thiazolidine-2,4 which can be Referred to as "Compound 18"

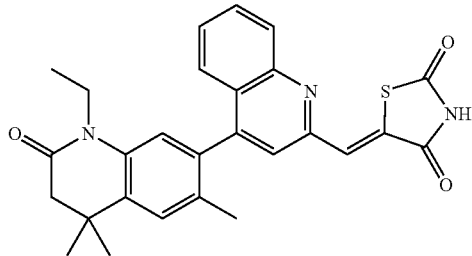

Prepared in a similar manner to example 1 using 1'-Ethyl-4',4',6'-trimethyl-2'-oxo-1',2',3',4'-tetrahydro-[4,7']biquinolinyl-2-carbaldehyde. mp 299–301° C. $^1$H-NMR (300 MHz, DMSO-d6): 1.05 (t, J=7.2 Hz, 3 H); 1.28 (s, 3 H); 1.33 (s, 3 H); 1.97 (s, 3 H); 3.94 (q, J=6.0 Hz, 2 H); 7.06 (s, 1 H); 7.40 (s,1 H); 7.49 (d, J=8.4 Hz, 1 H); 7.64 (t, J=7.2 Hz, 1 H); 7.86 (t, J=7.5 Hz, 1 H); 7.90 (s, 1 H); 8.01 (s, 1 H); 8.22 (d, J=8.1, 1 H); 12.54 (br s, 1 H).

a. 1'-Ethyl-4',4',6'-trimethyl-2'-oxo-1',2',3',4'-tetrahydro-[4,7']biquinolinyl-2-carbaldehyde.

A mixture of 1-Ethyl-4,4,'-trimethyl-2-oxo-1,2,3,'-tetrahydro-quinoline-7-boronic acid (0.25 g, 0.96 mmol), 4-trifluoromethanesulfonyloxy-quinoline-2-carbaldehyde (example 18 d) (0.17 g, 0.80 mmol) and potassium carbonate (0.21 g, 1.6 mmol) in toluene (5 mL), ethanol (1 mL) and water (0.75 mL) was degassed with argon for 30 minutes. Tetrakis(triphenylphosphine)palladium(0) (20 mg, 0.016 mmol) was added and the mixture heated at reflux under argon for 20 hrs. The solution was cooled to room temperature, diluted with ethyl acetate and washed successively with water and brine, dried over anhydrous magnesium sulfate, filtered and evaporated. The residue was purified on silica gel (0%–20% ethyl acetate in hexane) to give 0.18 g of 1'-Ethyl-4',4',6'-trimethyl-2'-oxo-1',2',3',4'-tetrahydro-[4,7'] biquinolinyl-2-carbaldehyde (52%).
$^1$H NMR (300 MHz; CDCl$_3$): 1.20 (t, J=7.2 Hz, 3 H), 1.35 (s, 3 H), 1.39 (s, 3 H), 1.99 (s, 3 H), 2.56 (s, 2 H), 4.00 (br d, 2 H), 6.86 (s, 1 H), 7.26 (d, J=2.7 Hz, 1 H), 7.62 (d, J=3.6 Hz, 1 H), 7.83 (m, J=1 H), 7.92 (s, 1 H), 8.33 (d, J=8.4 Hz, 1 H), 10.29 (s, 1 H).

b. 1-Ethyl-4,4,'-trimethyl-2-oxo-1,2,3,'-tetrahydro-quinoline-7-boronic acid.

To a solution of 7-Ethyl-4,4,6-trimethyl-7-(4,45,5-tetramethyl-[1,3,2]dioxaborolan-2-yl)-3,4-dihydro-1H-quinolin-2-one (13.8 g, 40.20 mmol) in dichloromethane (150 mL), was added dropwise under argon at −78° C. boron tribromide (19 mL, 201 mmol) and the solution slowly warmed up to room temperature and left overnight at room temperature. The solution was poored on ice-water slowly and extracted with ethylacetate, washed successively with water and brine, dried over anhydrous magnesium sulfate, filtered and evaporated. The residue was recrystalised from ethylacetate and hexane to give 1-ethyl-4,4,'-trimethyl-2-oxo-1,2,3,'-tetrahydro-quinoline-7-boronic acid (9 g, 86% yield). $^1$H NMR (300 MHz; CDCl$_3$): 1.06 (t, J=7.5 Hz, 3 H), 1.12 (s, 6 H), 2.30 (s, 3 H), 3.84 (brd, 2 H), 7.05 (s, 1 H), 7.11 (s, 1 H).

c. 1-Ethyl-4,4,6-trimethyl-7-(4,45,5-tetramethyl-[1,3,2] dioxaborolan-2-yl)-3,4-dihydro-1H-quinolin-2-one.

To a solution of 7-bromo-1-ethyl-4,4,6-trimethyl-3,4-dihydro-1H-quinoline-2-one (example 2b) (6.5 g, 91.95 mmol) in dioxane (65 mL), were added dropwise under argon triethylamine (12.3 mL, 87.78 mmol), palladium(II) acetate (0,246 g, 1.098 mmol), 2-(dicyclohexylphosphino) biphenyl (1.54 g, 4.39 mmol) and pinacolborane (9,6 mL, 65.85 mmol). The reaction mixture was heated at 85° C. for 3 hours then cooled to room temperature. Water (7 mL) was added slowly to the mixture followed by a saturated aqueous solution of ammonium chloride (100 mL). The mixture was extrated with ethylacetate and washed successively with water and brine, dried over anhydrous magnesium sulfate, filtered and evaporated. The crude was purified on silica gel (0–20% ethylacetate in hexane) to give 1-Ethyl-4,4,6-trimethyl-7-(4,45,5-tetramethyl-[1,3,2]dioxaborolan-2-yl)-3,4-dihydro-1H-quinolin-2-one (5.1 g, 67% yield). $^1$H NMR (300 MHz; CDCl$_3$): 1.24 (m, 9 H), 1.31 (s, 12 H), 2.45 (s, 2 H), 2.51 (s, 3 H), 4.09 (m, 2 H), 7.09 (s, 1 H), 7.42 (s, 1 H).

d. 4-trifluoromethanesulfonyloxy-quinoline-2-carbaldehyde.

To a solution of 4-trifluoromethanesulfonyloxy-quinoline-2-carboxylic acid ethyl ester (4.5 g, 12.88 g) in toluene (80 mL) was added slowly under argon at −78° C. diisobuthylaluminum hydride (1.5M in toluene, 12.88 mL, 19.33 mmol). The reaction mixture was stirred at −78° C. for 1 hour. Methanol (13 mL) was added slowly followed by water (26 mL). The reaction mixture was slowly warmed up to room temperature extracted with ethylacetate and washed with brine, dried over magnesium sulfate, filtered and evaporated. The residue was purified on silica gel (5–10% ethylacetate in hexane) to give 2.9 g of 4-trifluoromethanesulfonyloxy-quinoline-2-carbaldehyde (74%). $^1$H NMR (300 MHz; DMSO-d6): 8–8.2 (m, 4 H), 8.43 (m, 1 H), 10.05 (s, 1H).

e. 4-trifluoromethanesulfonyl-quinoline-2-carboxylic acid ethyl ester.

To a solution of 4-hydroxy-quinoline-2-carboxylic acid ethyl ester (3.7 g, 17.03 g) in dichloromethane (100 mL) was added slowly under argon pyridine (1.65 mL, 20.44 mmol). The reaction mixture was cooled to 0° C. then trific anhydride (3.44 mL, 20.44 mmol) was added dropwise. The reaction mixture was slowly warmed up to room temperature and stirred at room temperature overnight. The solution was successively washed with water, 1N HCl, water, sat. NaHCO$_3$, water and brine, dried over magnesium sulfate, filtered and evaporated. The residue was purified on silica gel (5–15% ethylacetate in hexane) to give 4.5 g of 4-trifluoromethanesulfonyl-quinoline-2-carboxylic acid erthyl ester (76%).

Example 19

5-[2,5-Difluoro-4-methoxy-3-(1,4,4,6-tetramethyl-2-oxo-1,2,3,4-tetrahydro-quinolin-7-yl)-benzylidene]-thiazolidine-2,4-dione Which can be Referred to as "Compound 19"

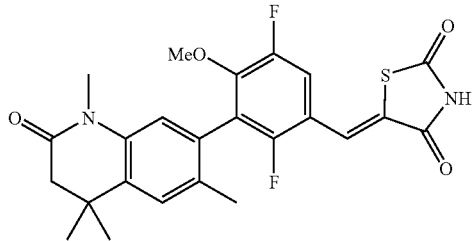

Prepared in a similar manner to example 1 using 2,5-Difluoro-4-methoxy-3-(1,4,4,6-tetramethyl-2-oxo-1,2,3,4-tetrahydro-quinolin-7-yl)-benzaldehyde. mp 165–167° C. $^1$H-NMR (300 MHz, DMSO-d-6): δ 1.27 (s, 6 H); 2.06 (s, 3 H); 2.49 (s, 2H); 3.24 (s, 3 H); 3.81(d, J=1.8 Hz, 3 H); 6.98 (s, 1 H); 7.31 (s, 1 H); 7.46 (dd, J$_1$=7.2 Hz, J$_2$=12.3 Hz, 1 H); 7.70 (s, 1 H); 12.77 (s, 1 H).

a. 2,5-Difluoro-4-methoxy-3-(1,4,4,6-tetramethyl-2-oxo-1,2,3,4-tetrahydro-quinolin-7-yl)-benzaldehyde.

A mixture of 1,4,4,6-tetramethyl-7-(4,4,5,5-tetramethyl-[1,3,2]dioxaborolan-2-yl)-3,4-dihydro-1H-quinoline-2-one (0.36 g, 1.1 mmol), 3-bromo-2,5-difluoro-4-methoxybenzaldehyde (example 13 a) (0.25 g, 0.1 mmol) and potassium carbonate (0.275 g, 1.99 mmol) in toluene (5 mL), ethanol (1 mL) and water (0.75 mL) was degassed with argon for 30 minutes. Tetrakis(triphenylphosphine)palladium(0) (58 mg, 0.05 mmol) was added and the mixture heated at reflux under argon for 20 hrs. The solution was cooled to room temperature, diluted with ethyl acetate and washed successively with water and brine, dried over anhydrous magnesium sulfate, filtered and evaporated. The residue was purified on silica gel (0%–20% ethyl acetate in hexane) to give 97 mg of 2,5-Difluoro-4-methoxy-3-(1,4,4,6-tetramethyl-2-oxo-1,2,3,4-tetrahydro-quinolin-7-yl)-benzaldehyde.

b. 1,4,4,6-tetramethyl-7-(4,4,5,5-tetramethyl-[1,3,2]dioxaborolan-2-yl)-3,4-dihydro-1H-quinoline-2-one.

To a solution of 7-bromo-1,4,4,6-tetramethyl-3,4-dihydro-1H-quinoline-2-one (example 1d) (1 g, 3.54 mmol) in dioxane (10 mL), were added dropwise under argon triethylamine (1.98 mL, 14.175 mmol), palladium(II)acetate (39.8 mg, 1.772 mmol), 2-(dicyclohexylphosphino)biphenyl (248 mg, 0.709 mmol) and pinacolborane (1.54 mL, 10.632 mmol). The reaction mixture was heated at 85° C. for 1.5 hours then cooled to room temperature. Water (1 mL) was added slowly to the mixture followed by a saturated aqueous solution of ammonium chloride. The mixture was extrated with ethylacetate and washed successively with water and brine, dried over anhydrous magnesium sulfate, filtered and evaporated. The crude was purified on silica gel (25% ethylacetate in hexane) to give 1,4,4,6-tetramethyl-7-(4,4,5,5-tetramethyl-[1,3,2]dioxaborolan-2-yl)-3,4-dihydro-1H-quinoline-2-one (0.91 g, 78% yield).

Example 20

5-[4-Trifluoromethoxy-3-(4,4,6-trimethyl-2-oxo-1,2,3,4-tetrahydro-quinolin-7-yl)-benzylidene]-thiazolidine-2,4-dione, which can be Referred to as "Compound 20"

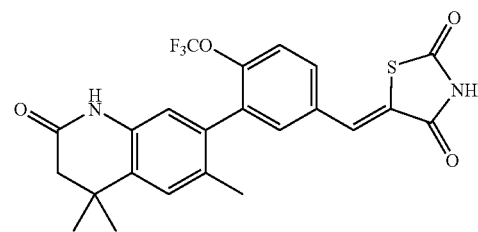

Prepared in a similar manner to example 1 using 4-Trifluoromethoxy-3-(4,4,6-trimethyl-2-oxo-1,2,3,4-tetrahydroquinolin-7-yl)-benzaldehyde. 76% yield. mp 306–308° C. $^1$H-NMR (300 MHz, DMSO-d-6): 1H NMR (300 MHz: DMSO): 1.26 (s, 3 H); 1.29 (s, 3 H); 2.04 (s, 3 H); 2.38 (m, 2 H); 6.69 (s, 1 H); 7.26 (s, 1 H); 7.58 (d, J=1.8 Hz, 1 H); 7.64 (dd, J$_1$=1.2 Hz, J$_2$=8.7 Hz, 1 H); 7.74 (dd, J$_1$=2.4 Hz, J$_2$=8.7 Hz., 1 H); 7.86 (s, 1 H); 10.16 (s, 1 H); 12.71 (br. s, 1 H)

The intermediate 4-Trifluoromethoxy-3-(4,4,6-trimethyl-2-oxo-1,2,3,4-tetrahydro-quinolin-7-yl)-benzaldehyde was prepared in a similar manner to example 1 a using 7-bromo-4,4,6-trimethyl-3,4- dihydro-1H-quinoline-2-one (Example 1e) and 3-formyl-6-trifluoromethoxy-1-phenyl boronic acid (example 1b).

Example 21

5-[3-(1-Ethyl-3,3,5-trimethyl-2-oxo-2,3-dihydro-1H-indol-6-yl)-4-trifluoromethoxy-benzylidene]-thiazolidine-2,4-dione, which can be Referred to as "Compound 21"

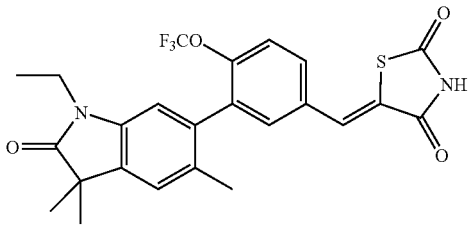

Prepared in a similar manner to example 1 using 3-(1-Ethyl-3,3,5-trimethyl-2-oxo-2,3-dihydro-1H-indol-6-yl)-4-trifluoromethoxy-benzaldehyde. 51% yield. $^1$H-NMR (300 MHz, DMSO-d-6): 1.1 (t, J=7.03 Hz, 3 H), 1.30 (s, 6 H), 2.07 (s, 3 H), 3.70 (q, J=7.33 Hz, 2 H), 6.91 (s, 1 H), 7.34 (s, 1 H), 7.65–7.68 (m, 2 H), 7.75 (dd, J$_1$=2.35, J$_2$=8.79 Hz, 1 H), 7.88 (s, 1 H), 12.7 (bs, 1 H).

a. 3-(1-Ethyl-3,3,5-trimethyl-2-oxo-2,3-dihydro-1H-indol-6-yl)-4-trifluoromethoxy-benzaldehyde To a solution of 4-trifluoromethoxy-3-(3,3,5-trimethyl-2-oxo-2,3-dihydro-1H-indol-6-yl)-benzaldehyde (210 mg, 0.58 mmol) in DMSO (5 mL) was added KOH (powder, 65 mg, 1.16 mmol) and iodoethane (180 mg, 1.16 mmol) under argon. The mixture was stirred at room temperature for about 2 hours. 5 mL of water was added, the product was extracted with EtOAc, washed with brine, dried over $MgSO_4$, filtered and evaporated under reduced pressure. The residue was purified by column chromatography on silica gel (hexane: EtOAc/4:1). 120 mg of pale colorles solid was obtained (yield: 53%). $^1$H NMR (300 MHz, $CDCl_3$, ppm): δ: 1.24 (t, J=7.03 Hz, 3 H), 2.10 (s, 3 H), 3.74 (m, 2 H), 6.65 (s, 1 H), 7.12 (s, 1 H), 7.53 (dd, $J_1$=1.76 Hz, $J_2$=8.50 Hz, 1 H), 7.85 (d, J=2.34 Hz, 1 H), 7.96 (dd, $J_1$=2.34 Hz, $J_2$=8.50 Hz, 1 H), 10.05 (s, 1 H).

b. 4-Trifluoromethoxy-3-(3,3,5-trimethyl-2-oxo-2,3-dihydro-1H-indol-6-yl)-benzaldehyde A mixture of trifluoro-methanesulfonic acid 3,3,5-trimethyl-2-oxo-2,3-dihydro-1H-indol-6-yl ester (243 mg, 0.75 mmol), 3-formyl-6-trifluoromethoxy-1-phenyl boronic acid (Example 1b) (194 mg, 0.83 mmol) in toluene (10 mL), EtOH (1.5 mL) and water (1 mL) was deassed with argon for 20 minutes. Tetrakis(triphenylphosphine)palladium(0) (398 mg, 0.34 mmol), sodium carbonate (159 mg, 1.50 mmol) and lithium chloride (98 mg, 2.25 mmol) were added and the reaction mixture was heated to reflux under argon for 22 hours. The reaction was cooled to room temperature, diluted with ethylacetate and washed successively with water and brine, dried over $MgSO_4$, filtered and evaporated under reduced pressure. The residue was purified by column chromatography on silica gel (hexane: EtOAc/3:1) to give 166 mg of 4-trifluoromethoxy-3-(3,3,5-trimethyl-2-oxo-2,3-dihydro-1H-indol-6-yl)-benzaldehyde (61%). $^1$H NMR (300 MHz, $CDCl_3$, ppm): δ: 1.44 (s, 6 H), 2.09 (s, 3 H), 6.72 (s, 1 H), 7.10 (s, 1 H), 7.50–7.53 (m, 1H), 7.82 (d, J=2.34 Hz, 1 H), 7.94–7.97 (m, 2 H), 10.03 (s, 1 H).

c. Trifluoro-methanesulfonic acid 3,3,5-trimethyl-2-oxo-2,3-dihydro-1H-indol-6-yl ester To a solution of 6-Hydroxy-3,3,5-trimethyl-1,3-dihydro-indol-2-one (640 mg, 3.17 mmol) in dichloromethane (15 mL) was added at 0° C. triethylamine (642 mg, 884 uL, 6.34 mmol) followed by slow addition of trifluomethanesulfonic anhydride (984 mg, 586 uL, 3.49 mmol). The mixture was slowy warmed to room temperature and stirred at room temperature overnight. The solution was washed with water and brine, dried over $MgSO_4$, filtered and evaporated under reduced pressure. The residue was purified by column chromatography on silica gel (hexane: EtOAc/2:1) to give 750 mg of trifluoro-methanesulfonic acid 3,3,5-trimethyl-2-oxo-2,3-dihydro-1H-indol-6-yl ester (73%). $^1$H NMR (300 MHz, $CDCl_3$, ppm): δ: 1.40 (s, 6 H), 2.35 (s, 3 H), 6.82 (s, 1 H), 7.09 (s, 1 H), 8.10 (bs, 1 H).

d. 6-Hydroxy-3,3,5-trimethyl-1,3-dihydro-indol-2-one

6-Methoxy-1-(4-methoxy-benzyl-3,3,5-trimethyl-1,3-dihydro-indol-2-one (640 mg, 1.97 mmol) was mixed with acetic acid (0.7 mL)and 48% hydrobromic acid (7 mL) and heated to reflux 12 hours. The solution was cooled to 0° C. and aqueous $Na_2CO_3$ was added to adjust to pH=7 then extracted with EtOAc, washed with brine, dried over $MgSO_4$, filtered and evaporated under reduced pressure. The residue was purified by column chromatography on silica gel (hexane: EtOAc/4:1 to 1:1) to give 280 mg of 6-Hydroxy-3,3,5-trimethyl-1,3-dihydro-indol-2-one (74%). $^1$H NMR (300 MHz, DMSO-$d_6$, ppm): δ: 1.15 (s, 6 H), 2.026.34 (s,1 H), 6.89 (s, 1 H), 9.21 (s,1 H), 10.01(s, 1 H).

e. 6-Methoxy-1-(4-methoxy-benzyl-3,3,5-trimethyl-1,3-dihydro-indol-2-one

To a solution of N-(2-bromo-5-methoxy-4-methyl-phenyl)-N-(4-methoxy-benzyl)-isobutyramide (8.72 g, 21.4 mmol) in dry 1,4-dioxane (80 mL) was added sodium tert-butoxide (3.09 g, 32.1 mmol). Argon was bubbled through for about 15 minutes before adding palladium(II) acetate (241 mg, 1.07 mmol) and tricyclohexylphosphine (300 mg, 1.07 mmol). The mixture was heated to reflux for 16 hours. The mixture was cooled to room temperature, diluted with water and extracted with EtOAc, washed with brine, dried over $MgSO_4$, filtered and evaporated. The residue was purified by column chromatography on silica gel (hexane: EtOAc/5:1 to 3:1) to give 5.4 g of 6-Methoxy-1-(4-methoxy-benzyl-3,3,5-trimethyl-1,3-dihydro-indol-2-one (77%). $^1$H NMR (300 MHz, $CDCl_3$, ppm): δ: 1.38 (s, 6 H), 2.16(s, 3 H), 3.71(s, 3 H), 3.77 (s, 3 H), 4.84 (s, 2 H), 6.28 (s, 1 H), 6.82–6.85(m, 2 H), 6.95(s, 1 H), 7.19–7.22 (m, 2 H).

f. N-(2-bromo-5-methoxy-4-methyl-phenyl)-N-(4-methoxy-benzyl)-isobutyramide

To a solution of N-(2-bromo-5-methoxy-4-methyl-phenyl)-isobutyramide (6.83 g) in DMSO (40 mL) was added powder KOH (2.68 g, 47.7 mmol) and 4-methoxybenzyl chloride (7.5 g, 47.7 mmol) under argon. The mixture was stirred at room temperature for 17 hours. Water (30 mL) was added and the mixture extracted with EtOAc, washed with brine, dried over $MgSO_4$, filtered and evaporated under reduced pressure. The residue was purified by column chromatography on silica gel (hexane:EtOAc/10:1 t0 3:1) to give 8.72 g of N-(2-bromo-5-methoxy-4-methyl-phenyl)-N-(4-methoxy-benzyl)-isobutyramide (90%). $^1$H NMR (300 MHz, $CDCl_3$, ppm): δ: 1.00 (d, J=7.03 Hz, 3 H), 1.13 (d, J=6.45 Hz, 3 H), 2.17 (s, 3 H), 2.28 (m, 1 H), 3.48 (s, 3 H), 3.78 (s, 3 H), 3.84 (d, J=14.07 Hz, 1 H), 5.62 (d, J=14.07 Hz, 1 H), 6.06 (s, 1 H), 6.78–6.81 (m, 2 H), 7.10–7.13 (m, 2 H), 7.38 (s, 1 H).

g. N-(2-bromo-5-methoxy-4-methyl-phenyl)-isobutyramide

To a solution of N-(3-methoxy-4-methyl-phenyl)-isobutyramide (5.0 g, 24.1 mmol) in dichloromethane (200 mL) was added tetrabutylammonium tribromide (12.2 g, 25.3 mmol) at 0° C. The mixture was then stirred at room temperature for 20 hours. The solution was washed with water, brine, aqueous sodium bicarbonate solution, brine, dried over $MgSO_4$, filtered and evaporated under reduced pressure to give 6.83 g of N-(2-bromo-5-methoxy-4-methyl-phenyl)-isobutyramide (99%). $^1$H NMR (300 MHz, $CDCl_3$, ppm): δ: 1.29 (d, J=7.03 Hz, 6 H), 2.15 (s, 3 H), 2.59 (m, 1 H), 3.84 (s, 1 H), 7.24 (s, 1 H), 7.65 (bs, 1 H), 8.08 (s, 1 H).

h. N-(3-methoxy-4-methyl-phenyl)-isobutyramide

N-(3-hydroxy-4-methyl-phenyl)-isobutyramide (6.48 g, 33.5 mmol) was dissolved in 40 mL of acetone, potassium carbonate (13.9 g, 100.5 mmol) was added followed by methyl iodide (14.3 g, 100.5 mmol). The mixture was stirred at room temperature for about 3 days. The solution was filtered and evaporated under reduced pressure to give 6.6 g of N-(3-methoxy-4-methyl-phenyl)-isobutyramide (95%). $^1$H NMR (300 MHz, $CDCl_3$, ppm): δ: 1.26 (d, J=7.03 Hz, 6 H), 2.17 (s, 3 H), 2.49 (m, 1 H), 3.83 (s, 3 H), 6.71 (dd, J=2.05 Hz, 8.21 Hz, 1 H), 7.02 (d, J=7.91 Hz, 1 H), 7.11 (bs, 1 H), 7.47 (d, J=1.76 Hz, 1 H).

i. N-(3-hydroxy-4-methyl-phenyl)-isobutyramide

To a mixture of 5-amino-2-methylphenol (30 g, 244 mmol), 10% NaOH (210 mL) and dichloromethane (120 mL) was added at 0° C. slowly isobuyryl chloride (25.5 mL, 244 mmol) in dichloromethane (50 mL). The mixture was stirred at room temperature overnight. The aqueous layer was separated and extracted with EtOAc, washed with brine, dried over MgSO₄, filtered and evaporated under reduced pressure to give 37.2 g of N-(3-hydroxy-4-methyl-phenyl)-isobutyramide (78%). ¹H NMR (300 MHz, CDCl₃ ppm): δ: 1.21 (d, J=7.03 Hz, 6 H), 2.17(s, 3 H), 2.53 (m, 1 H), 2.58 (s, 3 H), 6.81(dd, J=2.05 Hz, 7.91 Hz, 1H), 6.97 (d, J=7.91 Hz, 1H), 7.38 (d, J=2.05 Hz, 1 H), 8.14 (bs, 1 H), 8.58 (s, 1 H).

Example 22

5-[4-Trifluoromethoxy-3-(3,3,5-trimethyl-2-oxo-2,3-dihydro-1H-indol-6-yl)-benzylidene]-thiazolidine-2,4-dione, which can be Referred to as "Compound 22"

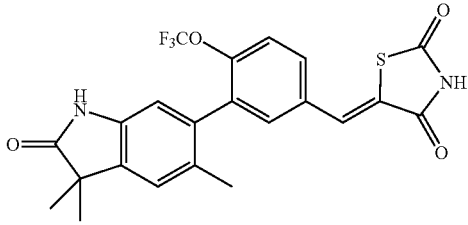

Prepared in a similar manner to example 1 using 4-trifluoromethoxy-3-(3,3,5-trimethyl-2-oxo-2,3-dihydro-1H-indol-6-yl)-benzaldehyde (example 21b). 58% yield.

¹H-NMR (300 MHz, DMSO-d-6): 1.29 (s, 6 H), 2.03 (s, 3 H), 6.64 (s, 1 H), 7.28 (s, 1 H), 7.61–7.66 (m, 2 H), 7.74 (dd, J=2.34, 8.79 Hz, 1 H), 7.86(s, 1 H), 10.33 (s, 1 H), 12.71 (bs, 1 H).

Example 23

5-[4-Trifluoromethoxy-3-(3,3,5-trimethyl-2-oxo-1-propyl-2,3-dihydro-1H-indol-6-yl)-benzylidene]-thiazolidine-2,4-dione, Which can be Referred to as "Compound 23"

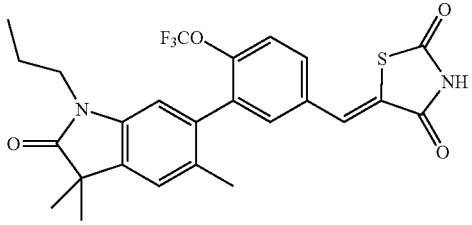

Prepared in a similar manner to example 1 using 4-trifluoromethoxy-3-(3,3,5-trimethyl-2-oxo-1-propyl-2,3-dihydro-1H-indol-6-yl)-benzaldehyde. 58% yield. ¹H-NMR (300 MHz, DMSO-d6, ppm): 0.82 (t, J=7.33 Hz, 3 H), 1.31 (s, 6 H), 1.58 (m, 2 H), 2.06 (s, 3 H), 3.62 (t, J=7.62 Hz, 2 H), 6.91 (s, 1 H), 7.34 (s, 1 H), 7.65 (d, J=2.35 Hz,1 H), 7.6 (m, 1 H), 7.75 (dd, J=2.34, 8.79 Hz, 1 H), 7.87 (s, 1 H), 12.7 (bs, 1 H).

The intermediate 4-trifluoromethoxy-3-(3,3,5-trimethyl-2-oxo-1-propyl-2,3-dihydro-1H-indol-6-yl)-benzaldehyde was prepared in a similar manner to example 21a using 4-trifluoromethoxy-3-(3,3,5-trimethyl-2-oxo-2,3-dihydro-1H-indol-6-yl)-benzaldehyde (example 21b) and propyl iodide. ¹H NMR (300 MHz, CDCl₃, ppm): δ: 0.93(t, J=7.3 Hz, 3 H), 1.45(s, 6 H), 1.70(m, 2 H), 2.10(s, 3 H), 3.66 (m, 2 H), 6.63 (s, 1 H), 7.11 (s, 1 H), 7.52–7.55 (m, 1 H), 7.85 (m, 1 H), 7.98 (m, 1H), 10.05 (s, 1 H).

Example 24

5-[3-(3,5,5,8,8-Pentamethyl-5,6,7,8-tetrahydro-naphthalen-2-yl)-4-trifluoromethoxy-benzylidene]-thiazolidine-2,4-dione, which can be Referred to as "Compound 24"

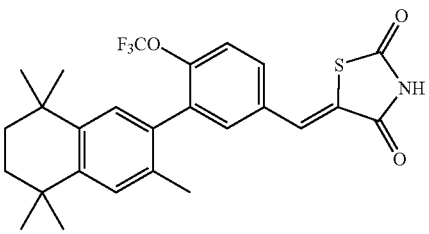

The synthesis and utility of Compound 24 was disclosed in U.S. Pat. No. 6,515,003, issued Feb. 4, 2003, which is incorporated herein in its entirety by this reference.

Example 25

5-[3-(1-Ethyl-4,4,6-trimethyl-2-oxo-1,2,3,4-tetrahydro-quinolin-7-yl)-4-trifluoromethoxy-benzylidene]-thiazolidine-2,4-dione, TRIS Salt, which can be Referred to as "Compound 25"

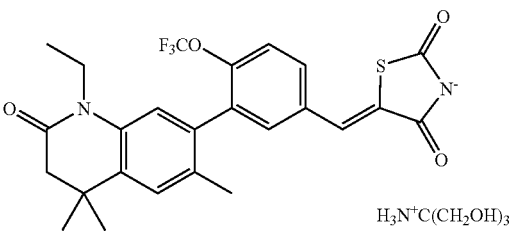

Compound 2 (14.85 g, 29.37 mmol) was dissolved in dry THF (100 mL) and a solution of tris(hydroxymethyl)aminomethane ("Tris," 3.56 g, 29.37 mmol) in dry methanol (20 mL0 was added dropwise at room temperature. The reaction mixture was stirred 48 hrs at room temperature, filtered and evaporated. The residue was redissolved in ethanol, evaporated and dried under high vacuum to afford 16.6 g of: 5-[3-(1-Ethyl-4,4,6-trimethyl-2-oxo-1,2,3,4-tetrahydro-quinolin-7-yl)-4-trifluoromethoxy-benzylidene]-thiazolidine-2,4-dione.TRIS. ¹H-NMR (300 MHz, DMSO-d-6): 1.06 (t, J=7.2 Hz, 3 H); 1.26 (s, 6 H), 2.08 (s, 3 H), 2.46 (s, 2 H), 3.47 (s, 6 H), 3.96 (br d, 2 H), 5.16 (s, 3H), 6.97 (s, 1 H), 7.30 (s, 1 H), 7.36(s, 1 H), 7.52 (d, J=2.4 Hz, 1 H), 7.55 (dd, J=1.5 Hz and 8.4 Hz, 1 H), 7.68 (dd, J=2.1 Hz and 8.7 Hz, 1 H).

Example 26

Differentiation of 3T3-L1 Pre-Adipocytes in an In Vitro Assay. (See Results in FIG. 1)

The following protocol was used to determine adipocyte differentiation activity of the compounds of the invention: Mouse pre-adipocyte 3T3-L1 cells obtained from ATCC (American Tissue Culture Collection, MD) were initially grown in DME Dulbecco's modified Eagle's medium containing 4500 mg/L glucose; 4 mM L-glutamine; 10 U/ml Pen-G; 10 mcg/ml Streptomycin and 10% Bovine Calf Serum (CS) at 37° C. and 10% $CO_2$. Cells were plated in 96 well plates at a density of approximately 3,000 cells/well and grown to confluence (when cells use 100% of the available space on the well) in the same medium. Differentiation experiments were conducted two days after confluence in a differentiation medium (DM) consisting of DME Dulbecco's modified Eagle's medium containing 4500 mg/L glucose; 4 mM L-glutamine; 10 U/ml Pen-G; 10 mcg/ml Streptomycin and 10% Fetal Calf Serum (FCS) and 1 µg/mL of insulin. Cells were then treated with the test compound at a concentration of $10^{-10}$ to $10^{-6}$ M, or with a control for fully-differentiated adipocytes, such as Dexamethasone/Insulin (2.5 µM; 10 µg/ml, respectively). Differentiation medium containing the compounds, with no further addition of insulin, was replaced every 2–3 days for a total of 7 days. Compound 24 was used as a standard for differention activity, and its ability to differentiate 3T3-L1 cells at 0.1 µM was taken as reference for 100% differentiation. Upon termination of the experiments the treated cells were washed once with PBS (Phosphate Buffer Saline, Irvine Scientific, Irvine, Calif.) and lysed in situ with 50 µL 10% Hecameg (Detergent, Calbiochem, San Diego). The cellular lysates were analyzed for their lipid content using the Triglyceride-GPO Trinder reagent from Sigma.

As shown in FIG. 1, many of compounds of the invention induce differenciation of 3T3-L1 cells.

Example 27

Oral Administration of Selected Compounds in the Treatment of Type 2 Diabetes in $KKA^y$ Mice (FIGS. 2a–e)

The procedure for this in-vivo assay for anti-diabetes activity was described in detail by Iwatsuka, et al. (1970 General Survey of Diabetic Features of Yellow KK Mice. *Endocrinol. Japon.* 17: 23–35, incorporated herein in its entirety by reference).

Experimental Procedures: Six to eight week-old male $KKA^y$ mice (obtained from Jackson Labs of Bar Harborb, Me.) were housed in a fixed 12–12-hr artificial light-dark cycle, and maintained on a standard rodent diet provided ad libitum. Animals were allowed two days to acclimate in this experimental environment prior to the initiation of the study.

Prior to initiation of treatment with the compounds of the invention, the animals were bled from the tail vein (100–200 µL of whole blood) and serum levels of glucose and triglycerides were measured in duplicate (Trinder kits; Sigma, St. Louis, Mo.). Based on these initial measures, animals were sorted into groups with approximately the same average serum glucose levels. Once sorted, the animals were housed one per cage and provided rodent diet ad libitum. Unless otherwise indicated, compounds were suspended in sesame oil, and administered by oral gavage once daily to animals in a volume of 3 ml/kg/dose.

Treatment Group A (n=5/group): (See Results in FIG. 2a)
1) $KKA^y$ vehicle control (sesame oil)
2) Compound 1 (3 mg/kg)
3) Compound 1 (10 mg/kg)
4) Compound 2 (3 mg/kg)
5) Compound 2 (10 mg/kg)

Treatment Group B (n=6/group): (See Results in FIG. 2b)
1) $KKA^y$ vehicle control (sesame oil)
2) Compound 11 (15 mg/kg)

Treatment Group C (n=6/group): (See Results in FIG. 2c)
1) $KKA^y$ vehicle control (sesame oil)
2) Compound 13 (15 mg/kg)

Treatment Group D (n=6/group): (See Results in FIG. 2d)
1) $KKA^y$ vehicle control (CMC)
2) Compound 25 (3 mg/kg, CMC)

Compound 25 was suspended in a solution of carboxymethyl cellulose (CMC; 1% carboxy methyl cellulose in $H_2O$, with 10% polyethelene glycol 400), and administered to animals in a volume of 5 ml/kg/dose.

Treatment Group E (n=5/group): (See Results in FIG. 2e)
1) $KKA^y$ vehicle control (10% HPβCD)
2) Compound 25 (1 mg/kg)
3) Compound 25 (3 mg/kg)
4) Compound 25 (10 mg/kg)

Compound 25 was dissolved in a 10% hydroxy propyl beta cyclodextrin solution, and administered to animals in a volume of 10 ml/kg/dose.

Figure 2A:
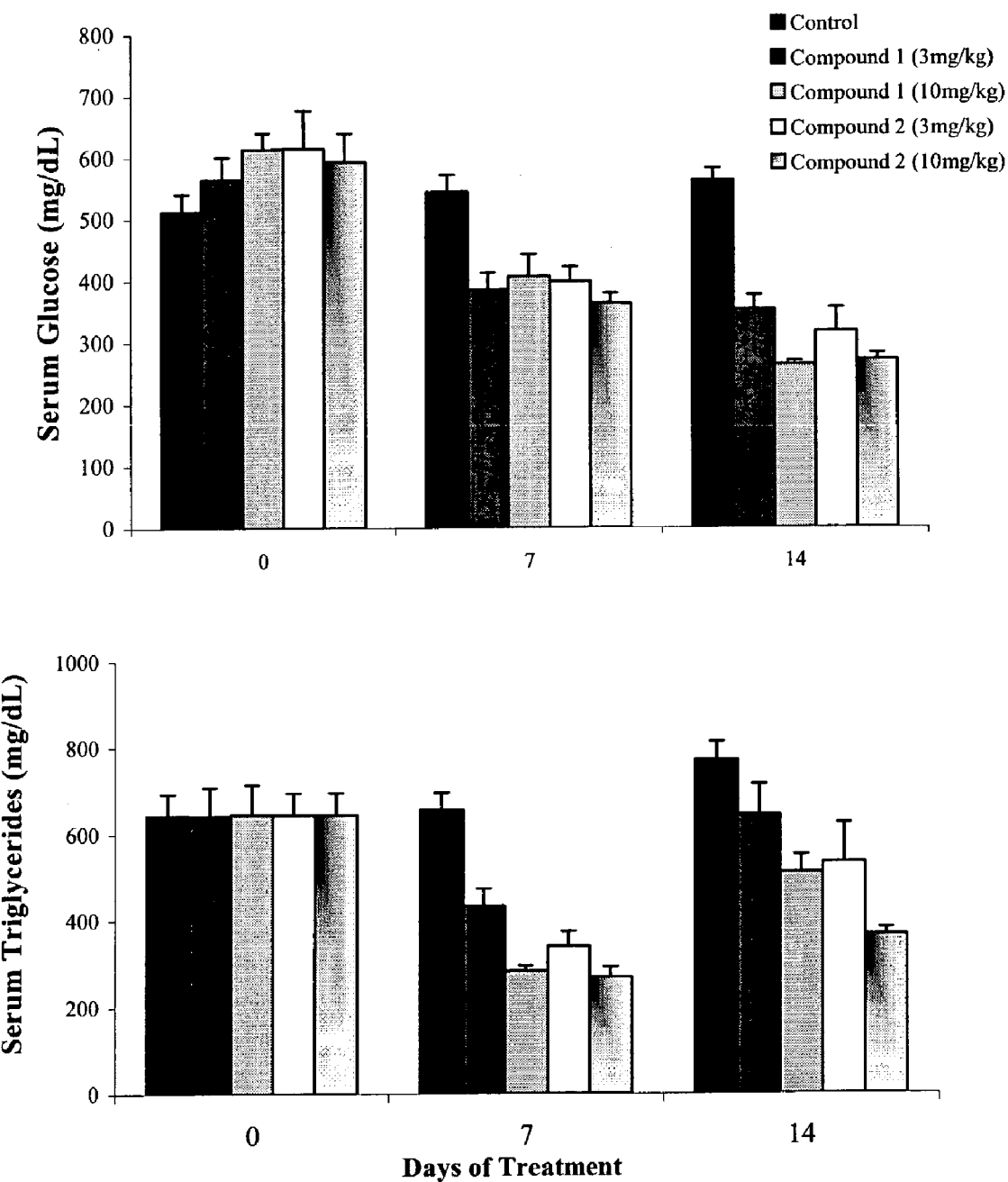
FIGS. 2a–d show the ability of certain compounds 1, 2, 11, 13, and 25, when orally administered, to simultaneously decrease the serum glucose and triglyceride levels of $KKA^y$ mice, as compared to control $KKA^y$ mice that do not receive the compounds.
Figure 2B:
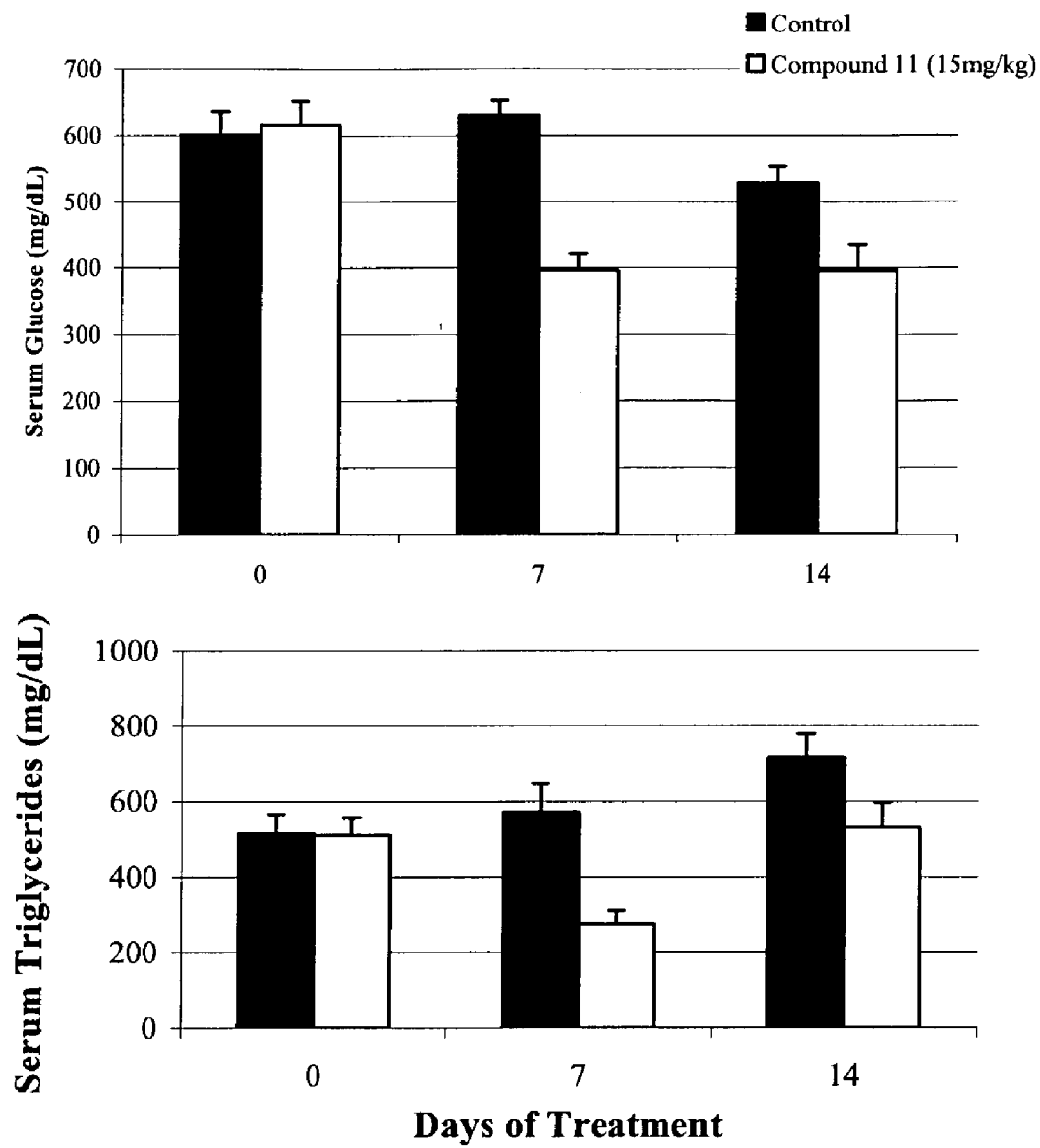
Figure 2C:
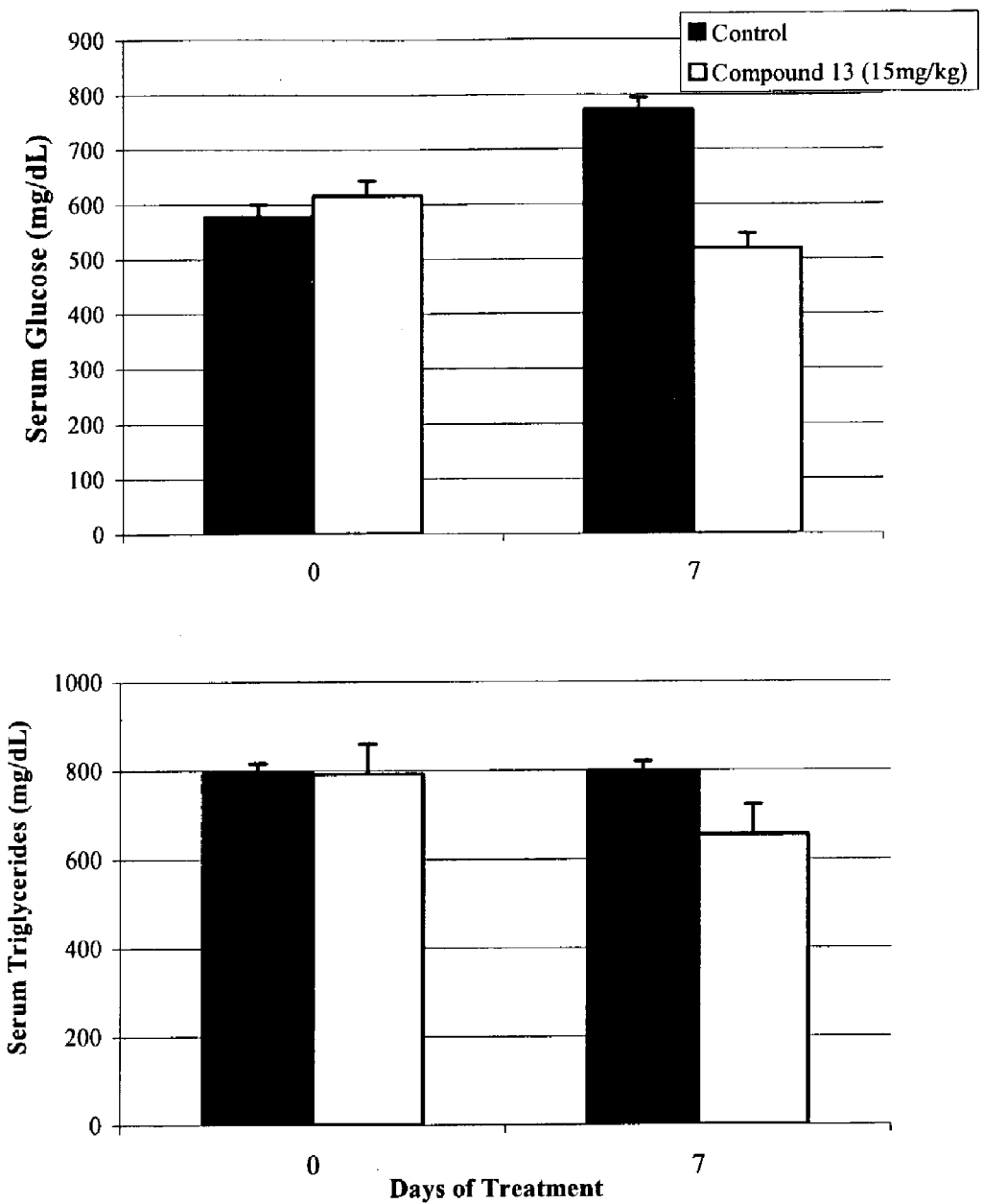
Figure 2D:
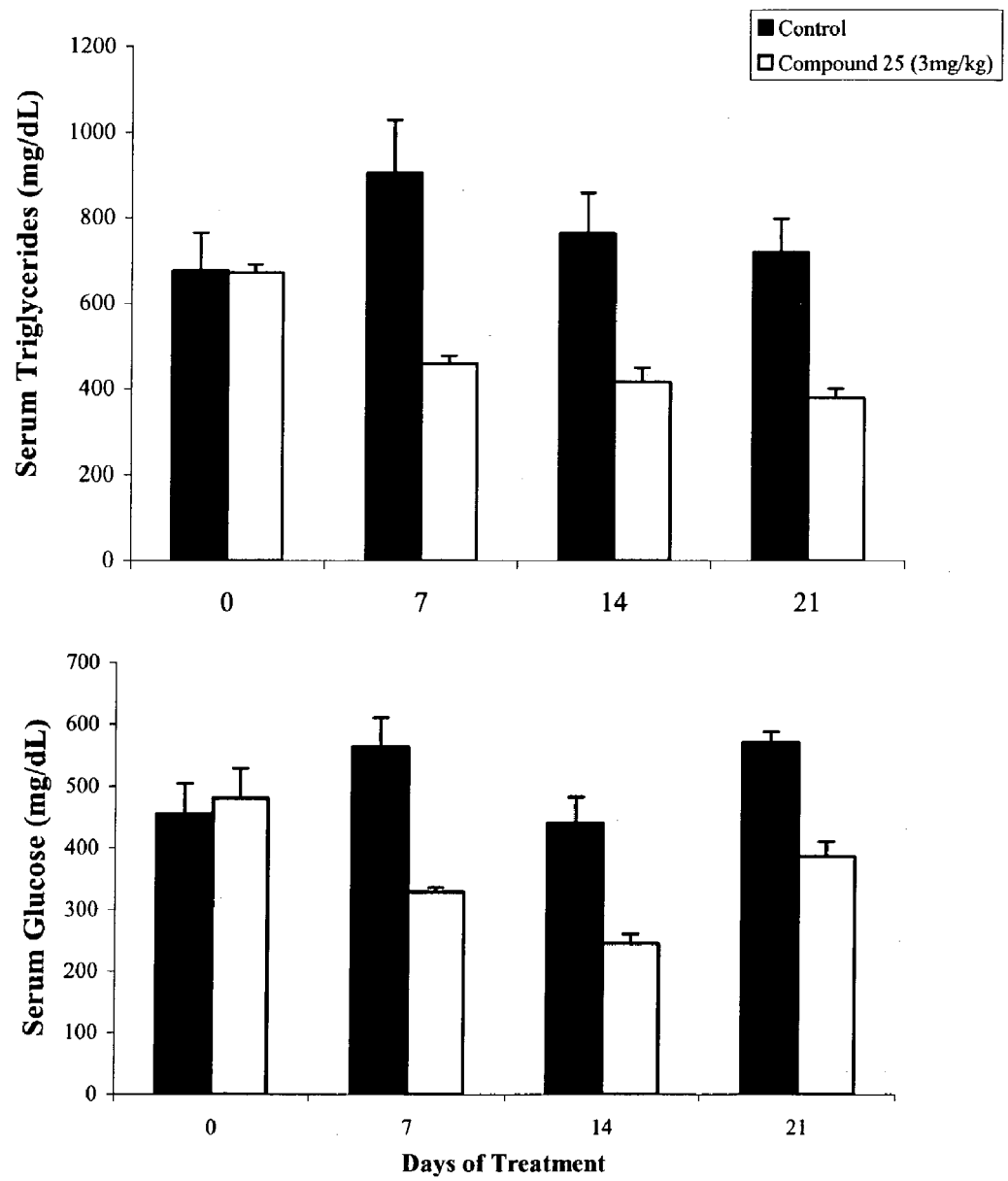
Figure 2E:
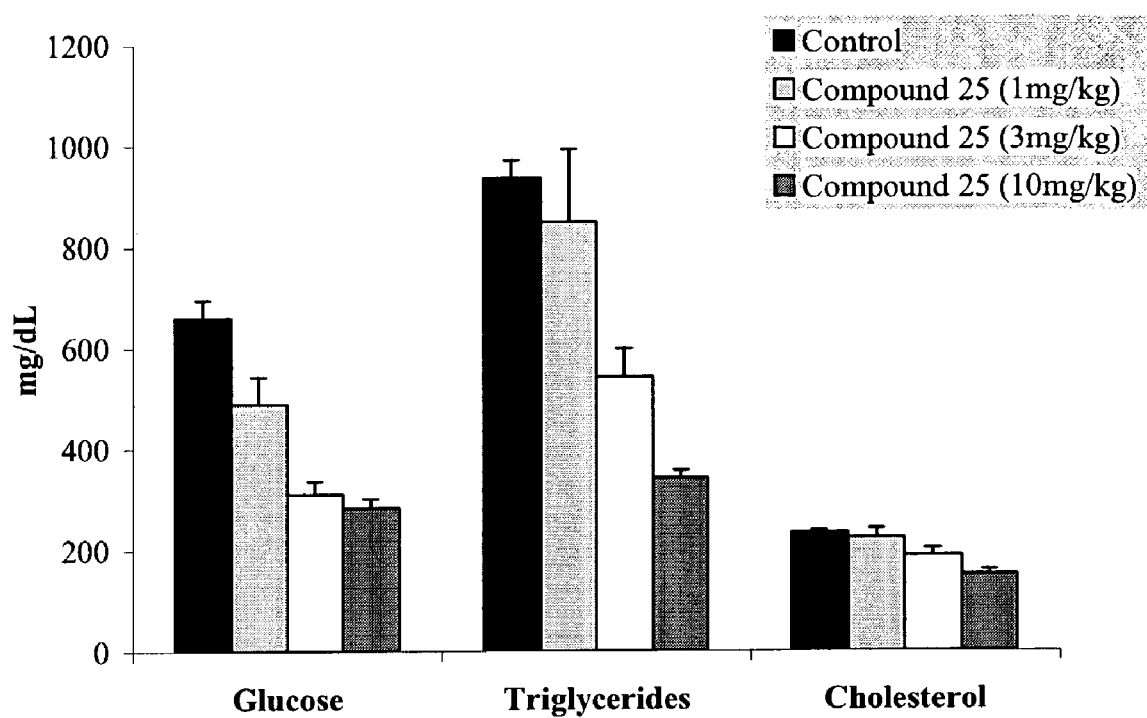
FIG. 2e shows the ability of compound 25, when orally administered, to simultaneously decrease the serum glucose, serum triglyceride, and serum cholesterol levels of $KKA^y$ mice at various dosage levels, as compared to control $KKA^y$ mice that do not receive the compound.

To monitor the effect of the tested compounds, animals were bled at the end of the dark cycle on days 7, 14, and/or 21 of the treatment period. Serum glucose, triglyceride and/or cholesterol levels were measured in duplicate. The blood is kept at room temperature to allow coagulation, after which the serum is separated and assayed for glucose, triglyceride and/or cholesterol levels. As shown in FIGS. 2a–2d all of the compounds tested reduced serum glucose and triglyceride levels, some with doses as low as 3 mg/kg when administered once a day. Also, as shown in FIG. 2e compound 25 causes an unexpectedly strong and simultaneous reduction in serum glucose, triglyceride and total cholesterol levels of type 2 diabetic $KKA^y$ mice following 4 weeks of treatment.

Example 28

Oral Administration of Selected Compounds in the Treatment of Type 2 Diabetes in db/db Mutant Mice (See Results in FIG. 3)

Experimental Procedure: Seven week-old female db/db mutant mice (C57BL/KsJ-db +/+m; Jackson Labs, Bar Harbour, Me.) were housed in a fixed 12—12-hr artificial light-dark cycle, and maintained on a standard high fat diet (containing at least 11% crude fat) provided ad libitum (Teklad S-2335). Animals were allowed two days to acclimate in this experimental environment prior to the initiation of the study. Prior to initiation of treatment, the animals were bled from the tail vein (100–200 µL of whole blood) and serum levels of glucose and triglycerides were measured in duplicate (Trinder kits; Sigma, St. Louis, Mo.). Based on these initial measures, animals were sorted into treatment groups with approximately the same average serum glucose levels. Once sorted, the animals were housed five per cage and provided high fat rodent diet ad libitum.

Treatment Groups (n=5/group):
1) db/db control (CMC)
2) Compound 25 (0.1 mg/kg, in CMC)
3) Compound 25 (0.3 mg/kg, in CMC)
4) Compound 25 (1 mg/kg, in CMC)

Compound 25 was suspended in a solution of carboxymethyl cellulose (CMC; 1% carboxy methyl cellulose in $H_2O$, with 10% polyethelene glycol 400), and administered to animals in a volume of 5 ml/kg/dose. The drug is administered by oral gavage once daily at the beginning of the artificial light cycle.

To monitor the effect of the tested compounds, animals were bled following a three-hour fast at the end of the dark cycle on days 0, 7, 14 of the treatment period. Fasting serum glucose and triglyceride levels were measured in duplicate. The blood is kept at room temperature to allow coagulation, after which the serum is separated and. assayed for glucose and triglyceride levels. As shown in FIG. 3, compound 25 ameliorate the symptoms of diabetes in with doses as low as 0.3 mg/kg when administered once daily. Both serum glucose and triglyceride were reduced compared to control animals, which showed the typical hyperglycemia and hypertriglyceridemia associated with type 2 diabetes.

Example 29

Cholesterol Efflux Assay from Macrophage Foam Cells as Induced by Compound 2. (See Results in FIG. 4)

Cholesterol efflux from macrophage foam cells was assayed as described by Sparrow. et al, J. Biol. Chem.,2002, 277, 10021–10027, which is encorporated herein in its entirety by this reference. THP-1 cells obtained from ATCC (Manassas, VI), were cultured in RPMI medium (Sigma, St-Louis, Mo.), containing 10% fetal calf serum (Sigma, St-Louis, Mo.), 0.05 µM 2-mercaptoethanol, 1 mM sodium pyruvate, 2 mM L-glutamine, 100 units/ml penicillin, 0.1 µg/ml streptomycin and 0.25 µg/ml amphotericin B obtained from Sigma (St-Louis, Mo.). The THP-1 cells were differentiated into macrophages in 24 well tissue culture dishes at a density of 0.5 million cells/well by incubation in the same medium plus 100 nM tetradecanoyl phorbol acetate (Sigma, St-Louis, Mo.), for 3 days.

After differentiation into macrophages, the cells were tested for cholesterol efflux as induced by compound 2 of the invention. Cells were labeled by incubation for 24 hr in fresh growth medium containing [3 H]-cholesterol (10 µCi/ml) (PerkinElmer, Boston, Mass.), and 50 µg/ml acetylated-LDL (Frederick, Md.) and 1% Fetal bovine serum (Sigma, St-Louis, Mo.). Following labeling with [3 H]-cholesterol, cells were washed, and incubated for an additional 24 hr in serum-free media containing 1 mg/ml bovine serum albumin (Sigma, St-Louis, Mo.), to allow for equilibration of [3 H]-cholesterol with intracellular cholesterol. Cholesterol efflux was initiated by adding the 10 µg/ml ApoA-I (Cal-Biochem, La Jolla, Calif.), with or without Compound 2 (1 µM final concentration) in serum free media. Compound 2 was added to cultured cells from stock solution, and control cells received an equivalent amount of vehicle. After 24 hr, media were harvested and cells were dissolved in 1 mM HEPES, pH 7.5 containing 0.5% of a detergent Triton X-100 (Sigma, St-Louis, Mo.). Media were briefly centrifuged to remove non-adherent cells, and then aliquots of both the supernatant and the dissolved cells were counted by liquid scintillation spectrometry to determine radioactivity.

Cholesterol efflux is expressed as a percentage, calculated as ([3 H]Cholesterol in medium)/([3 H]Cholesterol in medium+[3 H]cholesterol in cells)×100

As shown in FIG. 4, compound 2 increases cholesterol efflux from THP-1 cells as compared to non treated cells.

Example 30

Oral Administration of Selected Compounds in the Treatment of Diet-Induced Hypercholesterolemia in Wild Type Sprague Dawley Rats (See Results in FIGS. 5a–c)

Experimental Procedure: Six week-old male Sprague Dawley rats (obtained from Harlan of San Diego, Calif.) were housed in a fixed 12—12-hr artificial light-dark cycle, and maintained on a high cholesterol atherogenic diet (Paigen's Diet, obtained from Research Diet Inc. of New Brounswick, N.J.) was provided ad libitum. Animals were allowed six days to acclimate in this experimental environment prior to the initiation of the study.

Prior to initiation of treatment, the animals were bled from the tail vein (100–200 µL of whole blood) and serum levels of cholesterol were measured in duplicate (Cholesterol Infinity kits; Sigma, St. Louis, Mo.). Based on these initial measures, animals were sorted into groups with approximately the same average total cholesterol levels. Once sorted, the animals were housed three per cage and maintained on Paigen's diet ad libitum. All compounds to be tested were suspended in sesame oil and administered in a final volume of 3 ml/kg. Drug is administered by oral gavage once daily at the beginning of the artificial light cycle. To obtain a base line for lipid measurement, a control group maintained on standart rodent diet is included (lean control).

Treatment Group A (n=6/group): (See Results in FIG. 5a)
1) Lean control (Sesame Oil)
2) Control
3) Compound 2 (0.3 mg/kg)
4) Compound 2 (1 mg/kg)
5) Compound 2 (3 mg/kg)

Treatment Group B (n=6/group): (See Results in FIG. 5b)
1) Lean control (Sesame Oil)
2) Control
3) Compound 6 (3 mg/kg)

Treatment Group C (n=6/group): (See Results in FIG. 5c)
1) Lean control (10% HPβCD)
2) Control
3) Compound 25 (1 mg/kg)
4) Compound 25 (3 mg/kg)
5) Compound 25 (10 mg/kg)
6) Compound 25 (15 mg/kg)

The compounds were dissolved in a 10% hydroxy propyl beta cyclodextrin solution, and administered to animals in a volume of 10 ml/kg/dose.

To monitor the effect of the tested compounds, animals were bled from the tail vein at the end of the dark cycle on days 0 (for sorting) and day 5 of the treatment period. Fed serum cholesterol levels were measured in duplicate. The blood is kept at room temperature to allow coagulation, after which the serum is separated and assayed for total cholesterol (Infinity reagent, Sigma), HDL cholesterol (using HDL precipitating reagent and infinity reagent, Sigma) and LDL cholesterol (EzLDL kit, Sigma). As shown in FIGS. 5a–c, all compounds tested show significant reduction in total and LDL cholesterol levels and a significant increase in HDL cholesterol levels compared to high fat fed control animals.

Example 31

Oral Administration of Selected Compounds Slows the Progression of Mammary Tumors in Sprague Dawley Rats (See Results in FIG. 6)

Procedure: Five week-old female Sprague Dawley rats (Harlan) were housed in a fixed 12–12-hr artificial light-dark cycle, and maintained on a standard rodent diet provided ad libitum. Animals were allowed two days to acclimate in this experimental environment prior to the initiation of the study.

To induce mammary tumors, the female mice were injected intraperitoneally with the carcinogen n-nitroso-n-methylurea, in a single dose of 50 mg/kg in acidified normal saline (pH 4 w/acetic acid) at a final volume of 10 mg/ml (5 ml/kg). After eight weeks, mammary tumors are detected, and the tumor bearing females are sorted into treatment groups. Once sorted, the animals were housed four per cage and provided rodent diet ad libitum. All animals are treated with compound 1 or a vehicle for four weeks, during which time changes in tumor size are monitored. Tumors were classified as regressing, static or progressing.

Treatment groups (n=8/group):
1) Control (sesame oil)
2) Compound 6 (20 mg/kg)
3) Compound 11 (100 mg/kg)
4) Compound 13 (50 mg/kg)
5) Compound 24 (50 mg/kg)
6) Compound 25 (20 mg/kg)
7) Compound 25 (100 mg/kg)

All of the compounds tested were suspended in sesame oil, and administered to animals in a volume of 3 ml/kg/dose, except compound 25 which was dissolved in a 10% hydroxy propyl beta cyclodextrin solution, and administered to animals in a volume of 10 ml/kg/dose. All treatments were administered by oral gavage once daily for four weeks.

To monitor the effect of the tested compound, animals were examined for mammary tumors once every week. Tumors were classified into one of three categories, progressing, static or regressing. All of the compounds tested slowed the progression of mammary tumors compared to vehicle treated controls as shown in FIG. 6. Nevertheless, some of the compounds showed greater efficacy in this model. For example, Compound 25 caused the regression of tumors at doses as low as 20 mg/kg, whereas, compounds 11 and 13 only increase the number of static tumors (tumors that do not change in volume over the course of the study) compared to control animals without causing any regressions.

Example 32

A Comparison of Oral Bioavailability between Compound 24 and Compound 25 (See Results in FIG. 7)

Six to eight week-old male Sprague Dawley rats (Harlan) were housed in a fixed 12–12- hr artificial light-dark cycle, and maintained on a standard rodent diet provided ad libitum. Animals were allowed two days to acclimate in this experimental environment prior to the initiation of the study. Compounds 24 and 25 were dissolved in a 10% hydroxypropyl beta cyclodextrin solution and administered by oral gavage in a final dose of 10 mg/kg in a volume of 5 ml/kg. Treatment groups were divided as follows:

Treatment groups(n=3/group):
1) Compound 24 (10 mg/kg)
2) Compound 25 (10 mg/kg)

Each animal received a single treatment, after which, the animal was bled from the tail vein at the following time points: 0.5, 1, 2, 4, 6, 9, 12, and 26 hours after treatment. To measure the concentration of each compound in plasma, blood samples were collected in heparin-coated tubes, and the plasma was isolated and analyzed by HPLC. Compound 25 was present at a significantly higher concentration as compared to compound 24, which was only detected as being present at near the limit of detection in the plasma samples (FIG. 7). This highlights the improved bioavailability and pharmaceutical properties of Compound 25 over Compound 24.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:
1. A compound having the structure

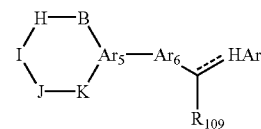

wherein
a) $Ar_5$ is an aryl, substituted aryl, heteroaryl, or substituted heteroaryl;
b) B, H, I, J and K are independently selected from —C(O)—, —C(S)—, —O—, —S—, —N($R_{101}$)—, —N($R_{102}$)—, —C($R_{103}$)($R_{104}$)—, —C($R_{105}$)($R_{106}$)—, or —C($R_{107}$)($R_{108}$)—, wherein one, or two of B, H, I, J or K can optionally be absent; and
  i) $R_{101}$, $R_{102}$, $R_{103}$, $R_{104}$, $R_{105}$, $R_{106}$, $R_{107}$ and $R_{108}$ are independently selected from hydrogen, hydroxyl, a halogen, amino, or an organic radical comprising 1 to 12 carbon atoms;
  ii) two of B, H, I, J and K form at least one radical having the structure

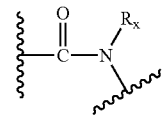

wherein $R_x$ is a $R_{101}$ or $R_{102}$ radical;
  iii) $Ar_5$ together with B, H, I, J and K comprise from 2 to 24 carbon atoms;
c) $Ar_6$ is an aryl, substituted aryl, heteroaryl, or substituted heteroaryl comprising from 2 to 18 carbon atoms;
d) $R_{109}$ is hydrogen, hydroxy, or an organic radical comprising 1 to 10 carbon atoms;
e) ----- is either present or absent;

f) HAr is a heterocycle having the structure

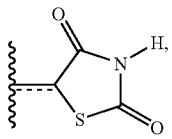
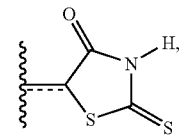

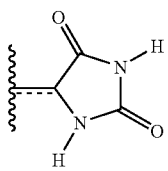
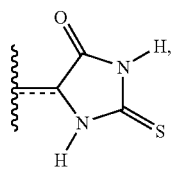

or a pharmaceutically acceptable salt thereof.

2. The compound of claim 1 wherein Ar$_5$ comprises a benzene, pyridine, pyrimidine, or pyrazine ring.

3. The compound of claim 2 wherein the Ar$_5$ ring is substituted with one or two additional substitutents independently selected from a halogen, an amino, or a radical comprising 1 to 4 carbon atoms selected from an ailcyl, a monosubstituted amino, a disubstituted amino, an alkoxy, or a haloalkoxy.

4. The compound of claim 1 wherein Ar$_5$ is a benzene ring, optionally substituted with one additional substitutent selected from a halogen, an amino, or a radical comprising 1 to 4 carbon atoms selected from an alkyl, a monosubstituted amino, a disubstituted amino, an alkoxy, or a haloalkoxy.

5. The compound of claim 1 wherein the radical

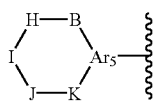

has the structure

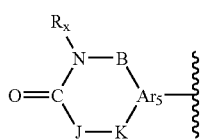

wherein R$_x$ is a R$_{101}$ or R$_{102}$ radical, and B and/or K can be present or absent.

6. The compound of claim 5 wherein B is absent.

7. The compound of claim 1 wherein the radical

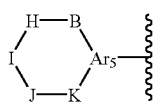

has the structure

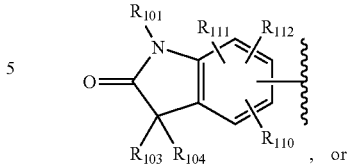, or

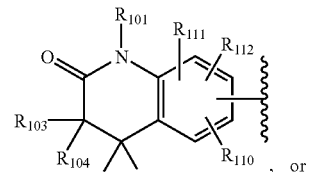, or

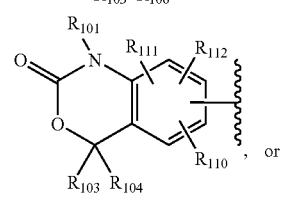, or

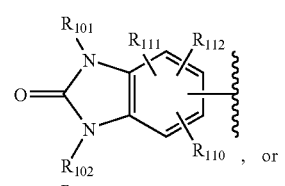, or

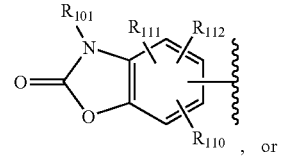, or

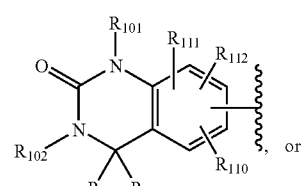, or

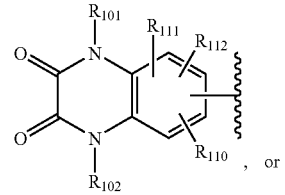, or

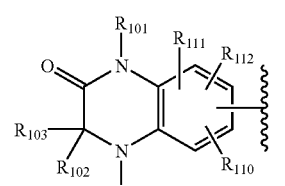

wherein R$_{110}$, R$_{111}$ or R$_{112}$ are independently selected from hydrogen, hydroxyl, a halogen, amino, or an organic residue comprising 1 to 12 carbon atoms.

8. The compound of claim 1 wherein the radical

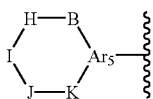

has the structure

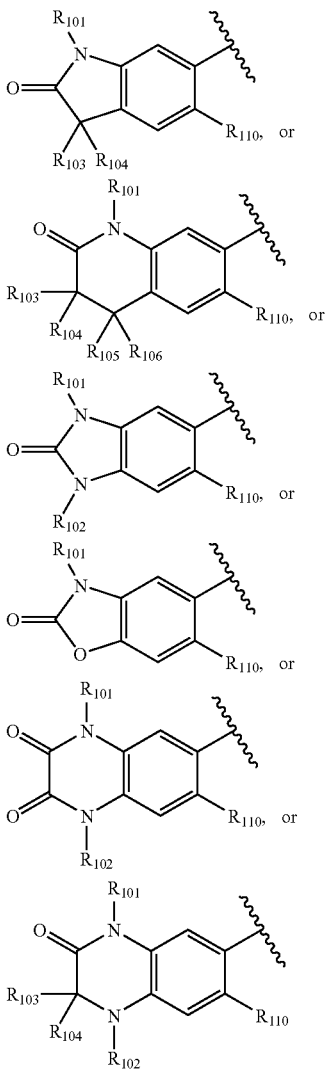

wherein $R_{101}$ and $R_{102}$, are independently selected from hydrogen, or an organic residue comprising 1 to 8 carbon atoms, and $R_{103}$, $R_{104}$, $R_{105}$, $R_{106}$ and $R_{110}$ are independently selected from hydrogen, hydroxyl, a halogen, amino, or an alkyl comprising 1 to 4 carbon atoms.

9. The compound of claim 1 wherein the radical

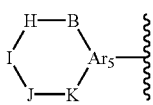

has the structure

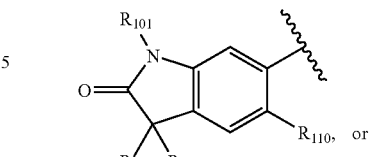

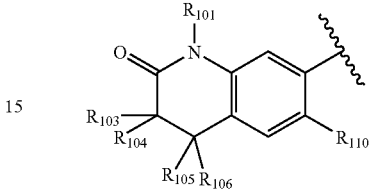

wherein $R_{101}$ is selected from hydrogen or an organic radical comprising 1 to 12 carbon atoms, and wherein $R_{103}$, $R_{104}$, $R_{105}$, $R_{106}$, and $R_{110}$ are independently selected from hydrogen or alkyls comprising 1 to 4 carbon atoms.

10. The compound of claim 1 wherein the radical

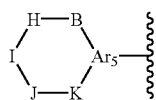

has the structure

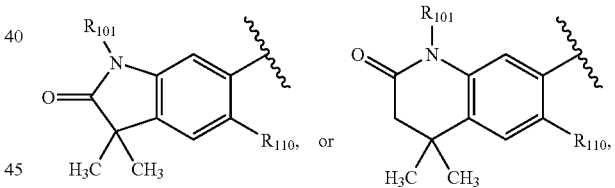

wherein $R_{101}$ and $R_{110}$ are an alkyl comprising 1 to 4 carbon atoms.

11. The compound of claim 1 wherein $R_{103}$ and $R_{104}$, or $R_{105}$ and $R_{106}$, or $R_{107}$ and $R_{108}$ are connected together to form a ring comprising 3 to 6 ring carbon atoms and from 0 to 3 optional ring heteroatoms selected from O, S, or N.

12. The compounds of claim 1 wherein $R_{103}$ and $R_{104}$, or $R_{105}$ and $R_{106}$, or $R_{107}$ and $R_{108}$ are connected together to form a cycloalkyl comprising 3 to 6 carbon atoms.

13. The compound of claim 1 wherein the radical

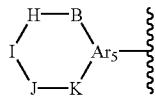

has the structure

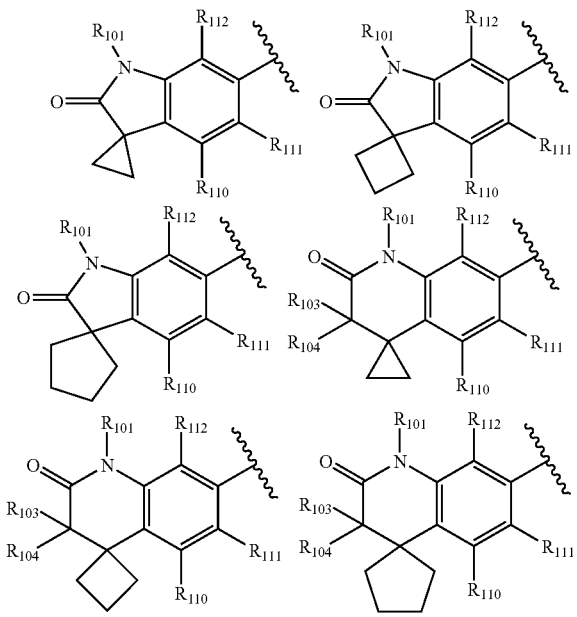

wherein $R_{110}$, $R_{111}$, and $R_{112}$ are independently selected from hydrogen or alkyls comprising 1 to 4 carbon atoms.

14. The compound of claim 1 wherein $Ar_6$ comprises a benzene, pyridine, pyrimidine, or pyrazine ring.

15. The compound of claim 14 wherein the $Ar_6$ ring is additionally substituted with one, two or three substituents independently selected from halogens or a radical comprising 1 to 4 carbon atoms selected from an alkyl, a haloalkyl, an amino, a mono-substituted amino, a di-substituted amino, an alkoxy, or a haloalkoxy.

16. The compound of claim 1 wherein $Ar_6$ has the structure

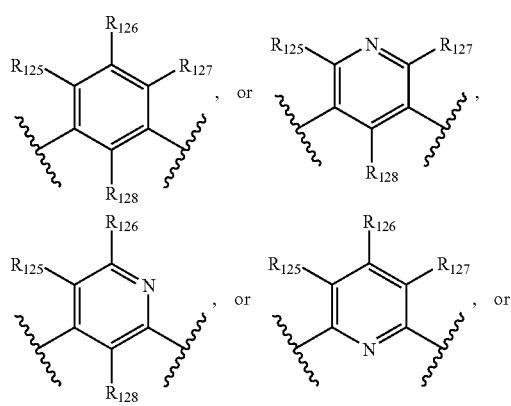

wherein $R_{125}$, $R_{126}$, $R_{127}$ and $R_{128}$ are substituents independently selected from hydrogen, halogen, intro, hydroxyl, amino, or a radical comprising 1 to 4 carbon atoms selected from alkyl, haloalkyl, cyano, acyloxy, mono-substituted amino, di-substituted amino, alkoxy, or haloalkoxy.

17. The compounds of claim 16 wherein $R_{125}$ is not hydrogen.

18. The compound of claim 1 wherein $Ar_6$ has the structure

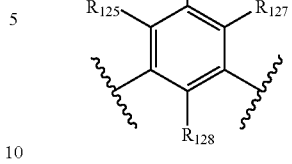

wherein $R_{125}$, $R_{126}$, $R_{127}$ and $R_{128}$ are substituents independently selected from hydrogen, halogen, nitro, hydroxyl, amino, or a radical comprising 1 to 4 carbon atoms selected from alkyl, haloalkyl, cyano, acyloxy, mono-substituted amino, di-substituted amino, alkoxy, or haloalkoxy, with the proviso that $R_{125}$ is not hydrogen.

19. The compound of claim 1 wherein $Ar_6$ has the structure

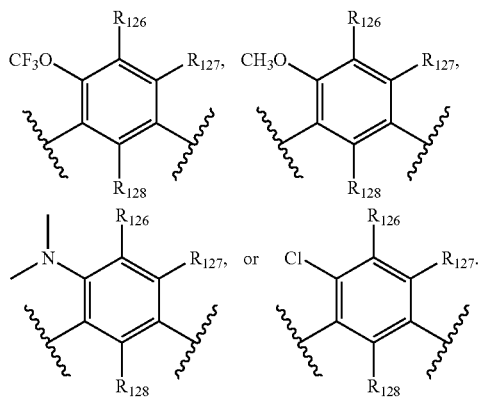

wherein $R_{126}$, $R_{127}$ and $R_{128}$ are independently or together hydrogen or halogen.

20. The compound of claim 19 wherein ----- is present.

21. The compound of claim 1 wherein HAr has the structure

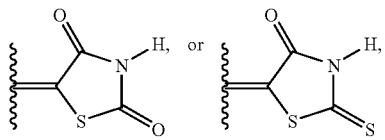

22. The compound of claim 1 wherein $R_{109}$ is hydrogen or an alkyl having 1 to 4 carbon atoms.

23. The compound of claim 1 wherein $R_{109}$ is hydrogen.

24. The compound of claim 8 wherein $R_{109}$ is hydrogen.

25. The compound of claim 24 wherein $Ar_6$ has the structure

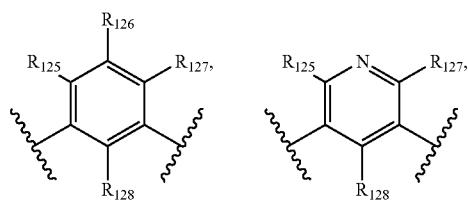

-continued

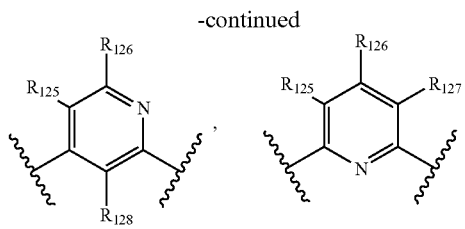

wherein $R_{125}$ is a halogen or an organic substituent comprising 1 to 4 carbon atoms selected from alkyl, haloalkyl, cyano, mono-substituted amino, di-substituted amino, alkoxy, or haloalkoxy; and $R_{126}$, $R_{127}$ and $R_{128}$ are independently selected from hydrogen, halogen, amino, and/or (b) organic substituents comprising 1 to 4 carbon atoms selected from alkyl, haloalkyl, cyano, mono-substituted amino, di-substituted amino, alkoxy, or haloalkoxy.

26. The compound of claim 25 wherein HAr has the structure

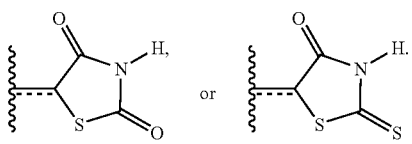

27. The compound of claim 25 wherein HAr has the structure

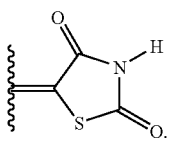

28. The compound of claim 27 in the form of a salt wherein HAr forms an anion having the structure

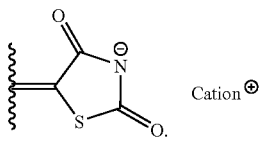

29. The compound of claim 28 wherein the cation is a pharmaceutically acceptable cation selected from metallic cations of aluminum, calcium, lithium, magnesium, potassium, sodium, or zinc, or an ammonium cations comprising a benzathine, chloroprocaine, choline, diethanolamine, ethylenediamine, meglumine, procaine, t-butylamine, or tris (hydroxymethyl)aminomethane radical.

30. The compounds of claim 1 that are effective to lower serum glucose levels of $KKA^y$ or db/db mice maintained on a high fat diet by at least about 5% when orally administered to the mice at a concentration of about 0.3 mg/kg for 7 days, as compared to control mice that do not receive the compounds.

31. The compounds of claim 1 that are effective to lower serum triglyceride levels of $KKA^y$ or db/db mice maintained on a high fat diet by at least about 5% when orally administered to the mice at a concentration of about 0.3 mg/kg for 7 days, as compared to control mice that do not receive the compounds.

32. A compound of claim 1 that is effective, when applied at a concentration of about $1\times10^{-6}$ M for a period of about 7 days, to induce sufficient differentiation of the mouse preadipocyte 3T3-L1 cells so as to increase the lipid content of the culture by at least about 20% of the lipid accumulation induced by 5-[3-(3,5,5,8,8-Pentamethyl-5,6,7,8-tetrahydro-naphthalen-2-yl)-4-trifluoromethoxy-benzylidene]-thiazolidine-2,4-dione when it is applied to control cultures of mouse preadipocyte 3T3-L1 cells at a concentration of about $1\times10^{-7}$ M.

33. A pharmaceutical composition comprising one or more pharmaceutically acceptable carriers and one or more compounds of claim 1, or a pharmaceutically acceptable salt thereof, in an amount effective for treating diabetes, cancer, or atherosclerosis, or modulating lipid metabolism, carbohydrate metabolism, lipid and carbohydrate metabolism, or adipocyte differentiation, in a mammal.

34. A method of modulating lipid metabolism, carbohydrate metabolism, lipid and carbohydrate metabolism, or adipocyte differentiation comprising administering to a mammal diagnosed as needing such modulation the compound of claim 1.

35. A method of modulating lipid metabolism, carbohydrate metabolism, lipid and carbohydrate metabolism, or adipocyte differentiation comprising administering to a mammal diagnosed as needing such modulation one or more compounds of claim 1, or a pharmaceutically acceptable salt thereof.

36. A method of making the compound of claim 1 comprising a) coupling i) an $Ar_5$ precursor compound having the structure

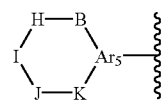

ii) with an $Ar_6$ precursor compound having the structure

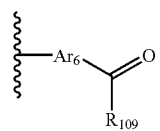

iii) to form a carbonyl containing precursor compound having the structure

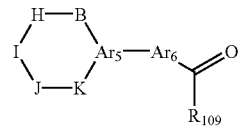

b) further reacting the carbonyl containing precursor compound so as to connect to the carbonyl of the carbonyl containing precursor an HAr heterocycle.

37. The method of claim 36 wherein the further reacting comprises condensing the carbonyl containing precursor compound with a compound having the structure

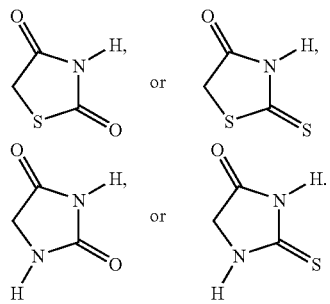

38. The method of claim 37 further comprising reacting the compound of claim 1 with a base to form a pharmaceutically acceptable salt.

39. A compound having the structure

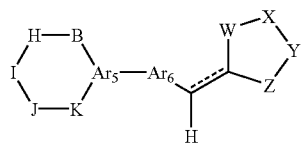

wherein a) the residue

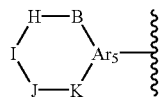

has the structure

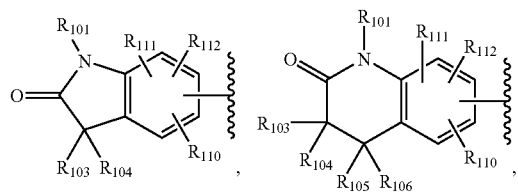

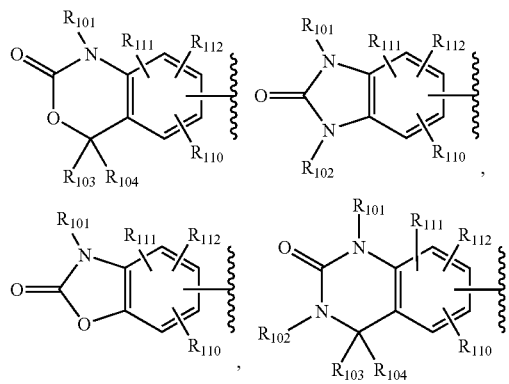

-continued

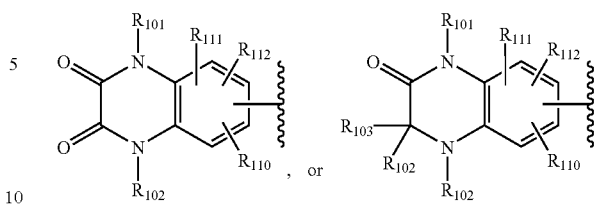

wherein $R_{101}$, $R_{102}$, $R_{103}$, $R_{104}$, $R_{105}$, $R_{106}$, $R_{110}$, $R_{111}$ and $R_{112}$ are independently selected from hydrogen, hydroxyl, a halogen, amino, or an organic residue comprising 1 to 6 carbon atoms;

b) $Ar_6$ has the structure

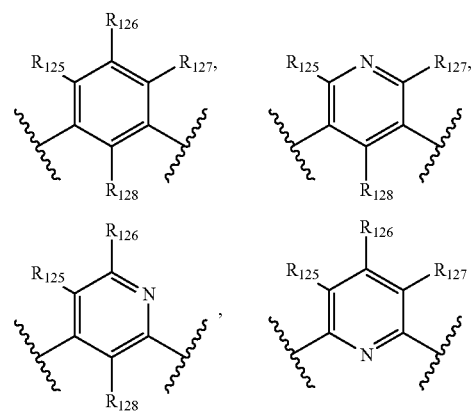

wherein $R_{125}$ is halogen, or an organic substituent residue comprising 1 to 4 carbon atoms selected from alkyl, haloalkyl, cyano, amino, mono-substituted amino, di-substituted amino, alkoxy, or haloalkoxy; and $R_{126}$, $R_{127}$ and $R_{128}$ are independently selected from hydrogen, halogen, amino, and/or organic substituents comprising 1 to 4 carbon atoms selected from alkyl, haloalkyl, cyano, acyloxy, mono-substituted amino, di-substituted amino, alkoxy, or haloalkoxy;

c) ----- is either present or absent; and d) W, X, Y and Z together form a heterocyclic radical having the structure

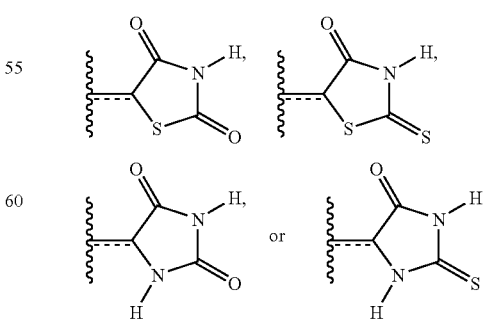

or a pharmaceutically acceptable salt thereof.

40. The compound of claim 39 wherein the residue

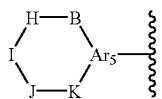

has the structure

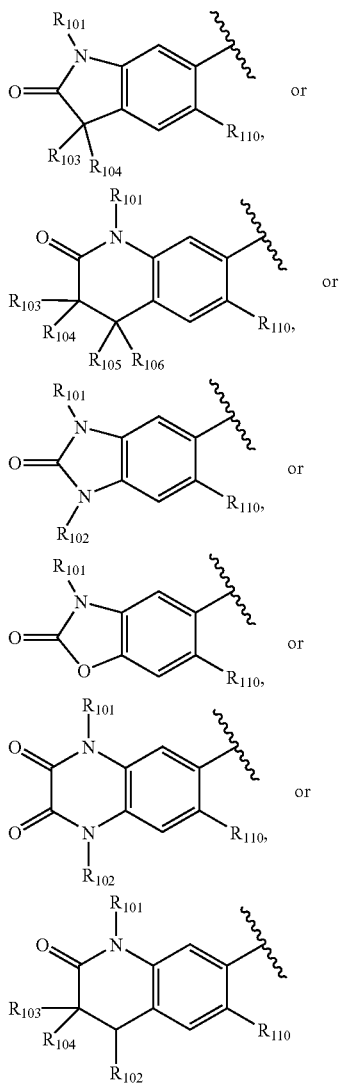

wherein $R_{101}$ and $R_{102}$, are independently selected from hydrogen, or an organic residue comprising 1 to 4 carbon atoms, and $R_{103}$, $R_{104}$, $R_{105}$, $R_{106}$ and $R_{110}$ are independently selected from hydrogen, hydroxyl, a halogen, amino, or an alkyl comprising 1 to 4 carbon atoms.

41. The compound of claim 39 wherein the residue

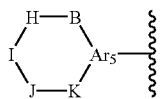

has the structure

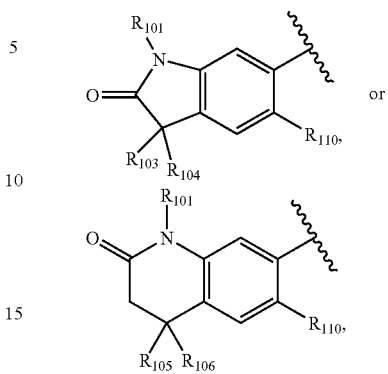

wherein $R_{103}$, $R_{104}$, $R_{105}$ and $R_{106}$ are independently selected from hydrogen, or an organic residue comprising 1 to 4 carbon atoms, and $R_{110}$ is selected from hydrogen, hydroxyl, a halogen, amino, or an alkyl or alkoxide comprising 1 to 4 carbon atoms.

42. A compound having the structure

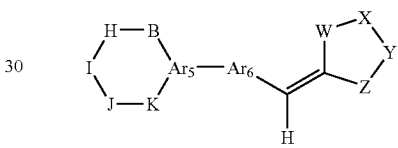

wherein a) the residue

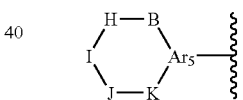

has the structure

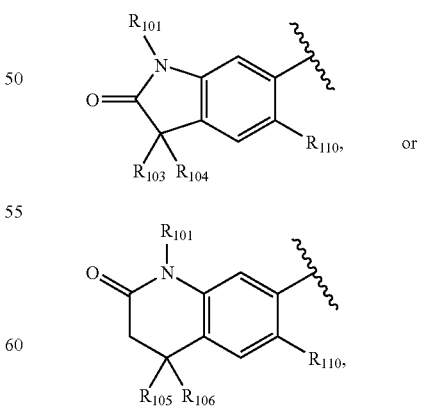

wherein $R_{101}$, $R_{103}$, $R_{104}$, $R_{105}$, $R_{106}$ and $R_{110}$ are independently selected from hydrogen, or an alkyl comprising 1 to 4 carbon atoms b) Ar$_6$ has the structure

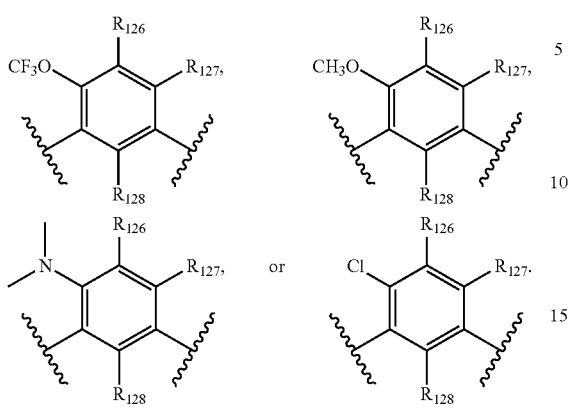

wherein R$_{126}$, R$_{127}$ and R$_{128}$ are independently selected from hydrogen or a halogen; and c) W, X, Y and Z together form a heterocyclic radical having the structure

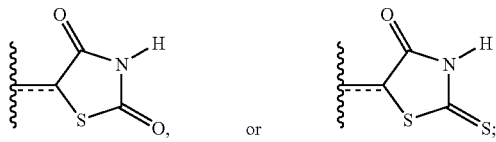

or a pharmaceutically acceptable salt thereof.

43. A compound of Formula (200):

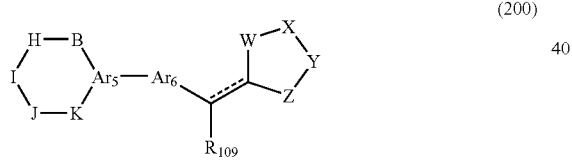

wherein:

a) the B, H, I, J and K residues are independently selected from —C(O)—, —C(S)—, —O—, —S—, —N(R$_{101}$)—, —N(R$_{102}$)—, —C(R$_{103}$)(R$_{104}$)—, —C(R$_{105}$)(R$_{106}$)—, or —C(R$_{107}$)(R$_{108}$)— residues, and from zero to two of the B, H, I, J or K residues can be absent; wherein:

i) R$_{101}$, R$_{102}$, R$_{103}$, R$_{104}$, R$_{105}$, R$_{106}$, R$_{107}$ and R$_{108}$ are independently selected from hydrogen, hydroxyl, a halogen, amino, or an organic residue comprising 1 to 12 carbon atoms; or two of the R$_{101}$, R$_{102}$, R$_{103}$, R$_{104}$, R$_{105}$, R$_{106}$, R$_{107}$ and R$_{108}$ residues can be connected together to form an exocyclic substituent residue comprising 1 to 6 ring carbon atoms and from 0 to 3 optional ring heteroatoms selected from O, S, or N; and ii) B, H, I, J and K together with the Ar$_5$ form a ring containing at least one amide residue having the formula

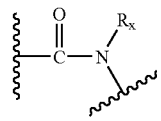

wherein R$_x$ is a R$_{101}$ or R$_{102}$ residue;

b) Ar$_5$ is an aryl, substituted aryl, heteroaryl, or substituted heteroaryl residue comprising from 3 to 6 ring carbon atoms and from 0 to 3 optional ring heteroatoms selected from O, S, or N;

c) Ar$_6$ is an aryl, substituted aryl, heteroaryl, or substituted heteroaryl residue comprising from 2 to 6 ring carbon atoms and from 0 to 3 optional ring heteroatoms selected from O, S, or N;

d) R$_{109}$ is hydrogen, hydroxy, or an organic residue comprising 1 to 10 carbon atoms;

e) ----- is either present or absent;

f) W, X, Y and Z are independently or together —C(O)—, —C(S)—, —S—, —O— or —NH—, to form a 2,4-thiazolidinedione, 2-thioxo-thiazolidine-4-one, 2,4-imidazolidinedione or 2-thioxo-imidazolidine-4-one residue; or a pharmaceutically acceptable salt thereof.

44. A compound having the formula:
5-[3-(1-Ethyl-4,4,6-trimethyl-2-oxo-1,2,3,4-tetrahydro-quinolin-7-yl)-4-trifluoromethoxy-benzylidene]-thiazolidine-2,4-dione, or a pharmaceutically acceptable salt thereof.

45. A compound having the formula:
5-[3-(1,4,4,6-Tetramethyl-2-oxo-1,2,3,4-tetrahydro-quinolin-7-yl)-4-trifluoromethoxy-benzylidene]-thiazolidine-2,4-dione, 5-[4-Dimethylamino-3-(1,4,4,6-tetramethyl-2-oxo-1,2,3,4-tetrahydro-quinolin-7-yl)-benzylidene]-thiazolidine-2,4-dione, 5-[4-Dimethylamino-3-(1-ethyl-4,4,6-trimethyl-2-oxo-1,2,3,4-tetrahydro-quinolin-7-yl)-benzylidene]-thiazolidine-2,4-dione, 5-[3-(1,4,4,6-Tetramethyl-2-oxo-1,2,3,4-tetrahydro-quinolin-7-yl)-4-chloro-benzylidene]-thiazolidine-2,4-dione, 5-[3-(1-Ethyl-4,4,6-trimethyl-2-oxo-1,2,3,4-tetrahydro-quinolin-7-yl)-4-chloro-benzylidene]-thiazolidine-2,4-dione, 5-[2-Fluoro-4-methoxy-3-(1,4,4,6-tetramethyl-2-oxo-1,2,3,4-tetrahydro-quinolin-7-yl)-benzylidene]-thiazolidine-2,4-dione, 5-[3-(1-Propyl-4,4,6-trimethyl-2-oxo-1,2,3,4-tetrahydro-quinolin-7-yl)-4-trifluoromethoxy-benzylidene]-thiazolidine-2,4-dione, 5-[4-Dimethylamino-3-(1-propyl-4,4,6-trimethyl-2-oxo-1,2,3,4-tetrahydro-quinolin-7-yl)-benzylidene]-thiazolidine-2,4-dione, 5-[3-(1-Ethyl-4,4,6-trimethyl-2-oxo-1,2,3,4-tetrahydro-quinolin-7-yl)-2-fluoro-4-methoxy-benzylidene]-thiazolidine-2,4-dione, 5-[3-(1-Isopropyl-4,4,6-trimethyl-2-oxo-1,2,3,4-tetrahydro-quinolin-7-yl)-4-trifluoromethoxy-benzylidene]-thiazolidine-2,4-dione, 5-[4-Dimethylamino-3-(1-isopropyl-4,4,6-trimethyl-2-oxo-1,2,3,4-tetrahydro-quinolin-7-yl)-benzylidene]-thiazolidine-2,4-dione, 5-[3-(1-Ethyl-4,4,6-trimethyl-2-oxo-1,2,3,4-tetrahydro-quinolin-7-yl)-2,5-difluoro-4-methoxy-benzylidene]-thiazolidine-2,4-dione, 5-[4-Ethylamino-3-(1-ethyl-4,4,6-trimethyl-2-oxo-1,2,3,4-tetrahydro-quinolin-7-yl)-benzylidene]-thiazolidine-2,4-dione, 6-[2-Dimethylamino-5-(2,4-dioxo-thiazolidin-5-ylidenemethyl)-phenyl]-1,4,7-trimethyl-1,4-dihydro-quinoxaline-2,3-dione, 5-[3-(1-Benzyl-3,3,5-trimethyl-2-oxo-2,3-dihydro-1H-indol-6-yl)-4-trifluoromethoxy-benzylidene]-thiazolidine-2,4-dione, 5-[3-(1-Ethyl-4,4,6-trimethyl-2-oxo-1,2,3,4-tetrahydro-quinolin-7-yl)-5-fluoro-4-methoxy-benzylidene]-thiazolidine-2,4-dione, 5-(1'-Ethyl-4',4',6'-trimethyl-2'-oxo-1',2',3',4'-tetrahydro-[4,7']biquinolinyl-2-ylmethylene)-thiazolidine-2,4-dione, 5-[2,5-Difluoro-4-methoxy-3-(1,4,4,6-tetramethyl-2-oxo-1,2,3,4-tetrahydro-quinolin-7-yl)-benzylidene]-thiazolidine-2,4-dione, 5-[4-Trifluoromethoxy-3-(4,4,6-trimethyl-2-oxo-1,2,3,4-tetrahydro-quinolin-7-yl)-benzylidene]-thiazolidine-2,4-dione, 5-[3-(1-Ethyl-3,3,5-trimethyl-2-oxo-2,3-dihydro-1H-indol-6-yl)-4-trifluoromethoxy-benzylidene]-thiazolidine-2,4-dione, 5-[4-Trifluoromethoxy-3-(3,3,5-trimethyl-2-oxo-2,3-dihydro-1H-indol-6-yl)-benzylidene]-thiazolidine-2,4-dione, 5-[4-Trifluoromethoxy-3-(3,3,5-trimethyl-2-oxo-1-propyl-2,3-dihydro-1H-indol-6-yl)-benzylidene]-thiazolidine-2,4-dione;

or a pharmaceutically acceptable salt thereof.

46. The compound of claim 43 wherein $Ar_5$ comprises a phenyl ring optionally substituted with 1, 2, or 3 substitutent groups independently selected from inorganic groups or organic substituent groups comprising 1 to 12 carbon atoms.

47. The compound of claim 43 wherein $Ar_5$ is a phenyl ring, optionally substituted with one additional substitutent selected from a halogen, an amino, or a radical comprising 1 to 4 carbon atoms selected from an alkyl, a monosubstituted amino, a disubstituted amino, an alkoxy, or a haloalkoxy.

48. The compound of claim 43 wherein the radical

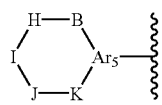

has the structure aryl:

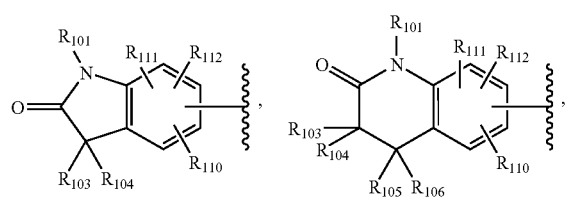

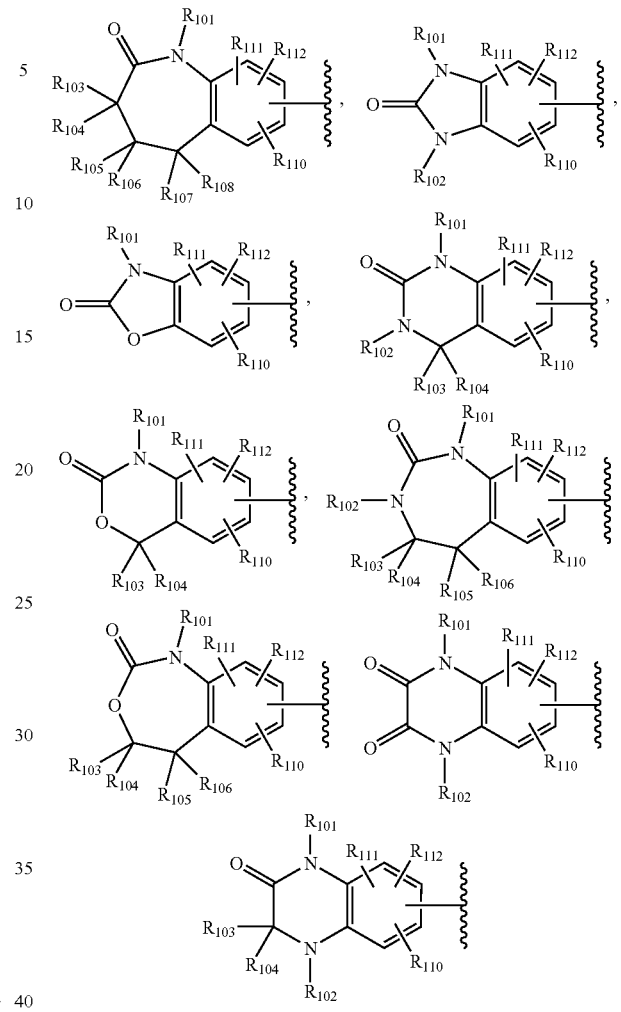

wherein $R_{101}$, $R_{102}$, $R_{103}$, $R_{104}$, $R_{105}$, $R_{106}$, $R_{107}$, $R_{108}$, $R_{110}$, $R_{111}$ or $R_{112}$ are independently selected from inorganic substitutents selected from hydrogen, halogen, cyano, nitro, hydroxyl, or amino, and organic residues comprising 1 to 4 carbon atoms selected from an alkyl, substituted alkyl, haloalkyl, alkenyl, substituted alkenyl, alkynyl, substituted alkynyl, acyloxy, amino, mono-substituted amino, di-substituted amino, alkylsulfonamide, arylsulfonamide, alkylurea, arylurea, alkylcarbamate, arylcarbamate, aryl, heteroaryl, alkoxy, substituted alkoxy, haloalkoxy, thioalkyl, thiohaloalkyl, carboxy, carboalkoxy, alkylcarboxamide, substituted alkylcarboxamide, dialkylcarboxamide or substituted dialkylcarboxamide residue.

49. The compound of claim 48 wherein the organic residues are independently selected from an alkyl, substituted alkyl, haloalkyl, alkoxy, substituted alkoxy, or haloalkoxy residues comprising from 1 to 4 carbon atoms.

50. The compound of claim 43 wherein the radical

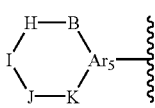

has the structure

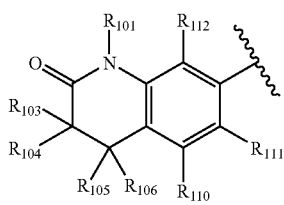
(207)

wherein $R_{101}$, $R_{103}$, $R_{104}$, $R_{105}$, $R_{106}$, $R_{110}$, $R_{111}$ and $R_{112}$ are independently selected from inorganic substitutents selected from hydrogen, halogen, cyano, nitro, hydroxyl, or amino, and organic residues comprising 1 to 4 carbon atoms selected from an alkyl, substituted alkyl, haloatkyl, alkenyl, substituted alkenyl, ailcynyl, substituted alkynyl, acyloxy, amino, mono-substituted amino, di-substituted amino, alkylsulfonamide, arylsulfonamide, alkylurea, arylurca, alkylcarbamate, arylcarbamate, aryl, heteroaryl, alkoxy, substituted alkoxy, haloalkoxy, thioalkyl, thiohaloalkyl, carboxy, carboalkoxy, alkylcarboxamide, substituted alkylcarboxamide, dialkylcarboxamide or substituted dialkylcarboxamide residue.

51. The compound of claim 43 wherein $R_{101}$ is hydrogen, alkyl or substituted alkyl.

52. The compound of claim 43 wherein $R_{101}$ is a straight or branched alkyl of $C_1$–$C_4$.

53. The compound of claim 43 wherein the radical

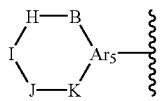

has the structure

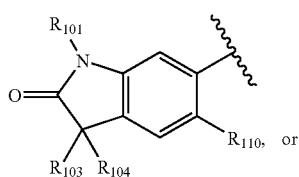

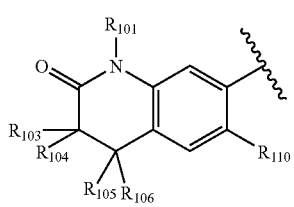

wherein $R_{101}$ is selected from hydrogen or an organic radical comprising 1 to 12 carbon atoms, and wherein $R_{103}$, $R_{104}$, $R_{105}$, $R_{106}$, and $R_{110}$ are independently selected from hydrogen or alkyls comprising 1 to 4 carbon atoms.

54. The compound of claim 43 wherein the radical

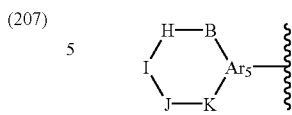

has the structure

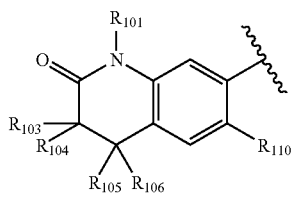

wherein $R_{101}$, $R_{103}$, $R_{104}$, $R_{105}$, $R_{106}$, and $R_{110}$ are independently selected from hydrogen or alkyls comprising 1 to 4 carbon atoms.

55. The compound of claim 43 wherein the radical

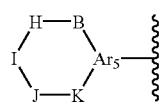

has the structure

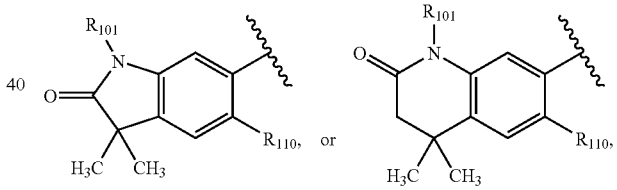

wherein $R_{101}$ and $R_{110}$ are an alkyl comprising 1 to 4 carbon atoms.

56. The compound of claim 43 wherein $Ar_6$ comprises a phenyl ring.

57. The compound of claim 56 wherein the $Ar_6$ ring is additionally substituted with one, two or three substituents independently selected from halogens or a radical comprising 1 to 4 carbon atoms selected from an alkyl, a haloalkyl, an amino, a mono-substituted amino, a di-substituted amino, an alkoxy, or a haloalkoxy.

58. The compound of claim 43 wherein $Ar_6$ comprises a pyridyl ring.

59. The compound of claim 58 wherein the $Ar_6$ ring is substituted with one, two or three substituents independently selected from halogens or a radical comprising 1 to 4 carbon atoms selected from an alkyl, a haloalkyl, an amino, a mono-substituted amino, a di-substituted amino, an alkoxy, or a haloalkoxy.

60. The compound of claim 43 wherein $Ar_6$ has the structure

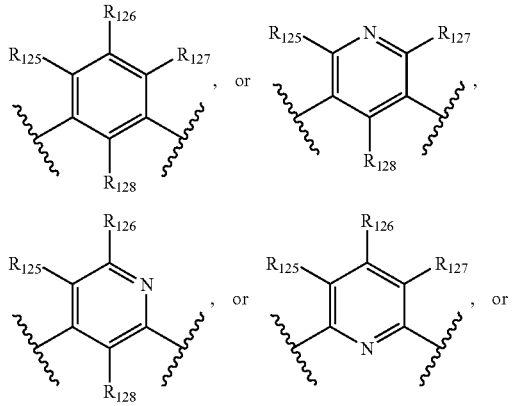

wherein $R_{125}$, $R_{126}$, $R_{127}$ and $R_{128}$ are substituents independently selected from hydrogen, halogen, nitro, hydroxyl, amino, or an organic radical comprising 1 to 4 carbon atoms.

61. The compounds of claim 60 wherein $R_{125}$ is not hydrogen.

62. The compounds of claim 60 wherein $R_{125}$ is an alkyl, substituted alkyl, haloalkyl, alkoxy, substituted alkoxy, haloalkoxy, halogen, amino, mono-substituted amino, or disubstituted amino radical comprising 1 to four carbons.

63. The compound of claim 43 wherein $Ar_6$ has the structure

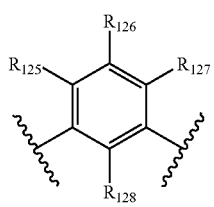

wherein $R_{125}$, $R_{126}$, $R_{127}$ and $R_{128}$ are substituents independently selected from hydrogen, halogen, nitro, hydroxyl, amino, or a radical comprising 1 to 4 carbon atoms selected from alkyl, haloalkyl, cyano, acyloxy, mono-substituted amino, di-substituted amino, alkoxy, or haloalkoxy, with the proviso that $R_{125}$ is not hydrogen.

64. The compound of claim 43 wherein $Ar_6$ has the structure

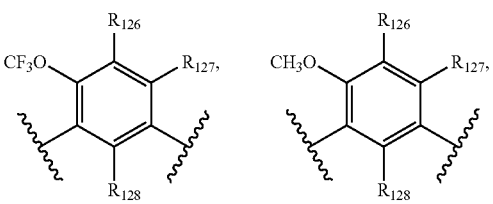

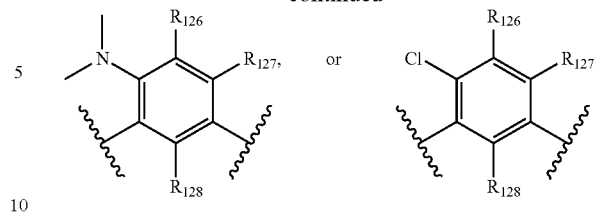

wherein $R_{126}$, $R_{127}$ and $R_{128}$ are independently or together hydrogen or halogen.

65. The compound of claim 43 wherein ----- is present.

66. The compound of claim 43 wherein $R_{109}$ is hydrogen.

67. The compound of claim 55 wherein $Ar_6$ has the structure

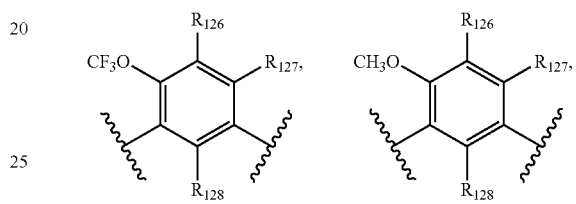

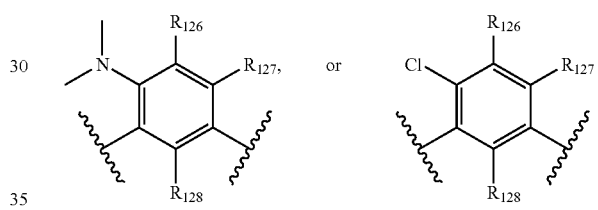

wherein $R_{126}$, $R_{127}$ and $R_{128}$ are independently or together hydrogen or halogen.

68. The compound of claim 67 wherein ----- is present.

69. The compound of claim 68 wherein $R_{109}$ is hydrogen.

70. The compound of claim 69 wherein the heterocycle comprising W, X, Y and Z has the structure

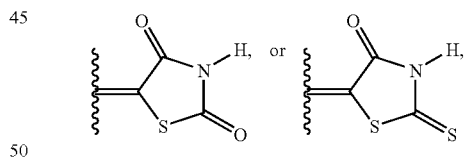

71. The compound of claim 69 wherein the heterocycle comprising W, X, Y and Z has the structure

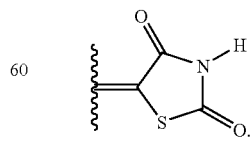

72. The compound of claim 71 in the form of a salt wherein the heterocycle comprising W, X, Y and Z forms an anion having the structure

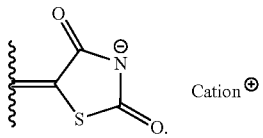

73. The compound of claim 72 wherein the cation is a pharmaceutically acceptable cation selected from metallic cations of aluminum, calcium, lithium, magnesium, potassium, sodium, or zinc, or an animonium cations comprising a benzathine, chloroprocaine, choline, diethanolamine, ethylenediamine, meglumine, procaine, t-butylamine, or tris (hydroxymethyl)aminomethane radical.

74. The compounds of claim 43 that are effective to lower serum glucose levels of KKA$^y$ or db/db mice maintained on a high fat diet by at least about 5% when orally administered to the mice at a concentration of about 0.3 mg/kg for 7 days, as compared to control mice that do not receive the compounds.

75. The compounds of claim 43 that are effective to lower serum triglyceride levels of KKA$^y$ or db/db mice maintained on a high fat diet by at least about 5% when orally administered to the mice at a concentration of about 0.3 mg/kg for 7 days, as compared to control mice that do not receive the compounds.

76. A compound of claim 43 that is effective, when applied at a concentration of about $1\times10^{-6}$ M for a period of about 7 days, to induce sufficient differentiation of the mouse preadipocyte 3T3-L1 cells so as to increase the lipid content of the culture by at least about 20% of the lipid accumulation induced by 5-[3-(3,5,5,8,8-Pentamethyl-5,6,7,8-tetrahydro-naphthalen-2-yl)-4-trifluoromethoxy-benzylidene]-thiazolidine-2,4-dione when it is applied to control cultures of mouse preadipocyte 3T3-L1 cells at a concentration of about $1\times10^{-7}$ M.

77. A pharmaceutical composition comprising one or more pharmaceutically acceptable carriers and one or more compounds of claim 43, or a pharmaceutically acceptable salt thereof.

* * * * *